(12) United States Patent
Porat et al.

(10) Patent No.: US 9,234,173 B2
(45) Date of Patent: *Jan. 12, 2016

(54) REGULATING STEM CELLS

(71) Applicant: KWALATA TRADING LIMITED, Nicosia (CY)

(72) Inventors: Yael Porat, Hod Hasharon (IL); Valentin Fulga, Toronto (CA); Svetlana Porozov, Rehovot (IL); Adina Belleli, Gan-yavne (IL)

(73) Assignee: Kwalata Trading Ltd., Nicosia (CY)

( * ) Notice: Subject to any disclaimer, the term of this patent is extended or adjusted under 35 U.S.C. 154(b) by 0 days.

This patent is subject to a terminal disclaimer.

(21) Appl. No.: 13/970,807

(22) Filed: Aug. 20, 2013

(65) Prior Publication Data

US 2013/0345083 A1  Dec. 26, 2013

Related U.S. Application Data

(63) Continuation of application No. 12/224,913, filed as application No. PCT/IL2007/000308 on Mar. 8, 2007, now Pat. No. 8,541,232.

(60) Provisional application No. 60/780,781, filed on Mar. 8, 2006.

(51) Int. Cl.
```
C12N 5/074     (2010.01)
C12N 5/078     (2010.01)
C12N 5/0781    (2010.01)
C12N 5/0797    (2010.01)
C12N 5/071     (2010.01)
C12Q 1/02      (2006.01)
A61C 13/08     (2006.01)
C12N 5/00      (2006.01)
A61K 35/12     (2015.01)
```

(52) U.S. Cl.
CPC ............ *C12N 5/0634* (2013.01); *C12N 5/0607* (2013.01); *C12N 5/0692* (2013.01); *A61K 2035/124* (2013.01); *C12N 2501/14* (2013.01); *C12N 2501/165* (2013.01); *C12N 2501/23* (2013.01); *C12N 2501/33* (2013.01); *C12N 2501/39* (2013.01); *C12N 2501/392* (2013.01); *C12N 2501/599* (2013.01); *C12N 2501/91* (2013.01); *C12N 2510/00* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | |
|---|---|---|
| 3,411,507 A | 11/1968 | Wingrove |
| 3,774,243 A | 11/1973 | Ng et al. |
| 3,837,339 A | 9/1974 | Aizenbreg et al. |
| 3,837,922 A | 9/1974 | Ng et al. |
| 3,861,397 A | 1/1975 | Rao et al. |
| 4,019,518 A | 4/1977 | Maurer et al. |
| 4,090,921 A | 5/1978 | Sawamura et al. |
| 4,140,963 A | 2/1979 | Rao et al. |
| 4,161,952 A | 7/1979 | Kinney et al. |
| 4,338,945 A | 7/1982 | Kosugi et al. |
| 4,344,438 A | 8/1982 | Schultz |
| 4,352,883 A | 10/1982 | Lim |
| 4,392,496 A | 7/1983 | Stanton |
| 4,402,694 A | 9/1983 | Ash et al. |
| 4,535,785 A | 8/1985 | van den Honert et al. |
| 4,559,948 A | 12/1985 | Liss et al. |
| 4,573,481 A | 3/1986 | Bullara |
| 4,578,323 A | 3/1986 | Hersl et al. |
| 4,585,005 A | 4/1986 | Lue et al. |
| 4,602,624 A | 7/1986 | Naples et al. |
| 4,608,985 A | 9/1986 | Chrish et al. |
| 4,628,942 A | 12/1986 | Sweeney et al. |
| 4,632,116 A | 12/1986 | Rosen |
| 4,640,785 A | 2/1987 | Carroll et al. |
| 4,649,936 A | 3/1987 | Ungar et al. |
| 4,663,102 A | 5/1987 | Brenman et al. |
| 4,696,902 A | 9/1987 | Bisconte |
| 4,702,254 A | 10/1987 | Zabara |
| 4,721,677 A | 1/1988 | Clark, Jr. |
| 4,739,764 A | 4/1988 | Lue et al. |
| 4,867,164 A | 9/1989 | Zabara |
| 4,883,755 A | 11/1989 | Carabasi et al. |
| 4,926,865 A | 5/1990 | Oman |
| 4,962,751 A | 10/1990 | Krauter |
| 4,966,853 A | 10/1990 | Matsuda et al. |

(Continued)

FOREIGN PATENT DOCUMENTS

| | | |
|---|---|---|
| CA | 2632834 | 6/2006 |
| WF | WO 90/15526 A1 | 12/1990 |

(Continued)

OTHER PUBLICATIONS

Kim et al., Neural differentiation potential of peripheral blood- and bone-marrow-derived precursor cells Brainresearc H1123 (2006) pp. 27-33.

An Office Action dated Feb. 19, 2014, which issued during the prosecution of Canadian Patent Application No. 2,567,578.

(Continued)

*Primary Examiner* — Debbie K Ware
*Assistant Examiner* — Kailash C Srivastava
(74) *Attorney, Agent, or Firm* — Nixon Peabody LLP; David S. Resnick; Leena H. Karttunen Contarino

(57) ABSTRACT

Provided are methods for producing progenitor/precursor cells from a population of initiating cells (ICP) that have a density of less than 1.072 g/ml and at least 25% of which are CD31Bright by in vitro stimulating the ICP with different factors.

18 Claims, 12 Drawing Sheets

(56) References Cited

U.S. PATENT DOCUMENTS

| | | |
|---|---|---|
| 4,981,779 A | 1/1991 | Wagner |
| 5,001,054 A | 3/1991 | Wagner |
| 5,011,472 A | 4/1991 | Aebischer et al. |
| 5,025,807 A | 6/1991 | Zabara |
| 5,042,497 A | 8/1991 | Shapland |
| 5,069,680 A | 12/1991 | Grandjean |
| 5,089,697 A | 2/1992 | Prohaska |
| 5,101,814 A | 4/1992 | Palti |
| 5,116,494 A | 5/1992 | Chick et al. |
| 5,170,802 A | 12/1992 | Mehra |
| 5,178,161 A | 1/1993 | Kovacs |
| 5,188,104 A | 2/1993 | Wernicke et al. |
| 5,199,428 A | 4/1993 | Obel et al. |
| 5,199,430 A | 4/1993 | Fang et al. |
| 5,203,326 A | 4/1993 | Collins |
| 5,205,285 A | 4/1993 | Baker |
| 5,209,231 A | 5/1993 | Cote et al. |
| 5,215,086 A | 6/1993 | Terry et al. |
| 5,224,491 A | 7/1993 | Mehra |
| 5,243,980 A | 9/1993 | Mehra |
| 5,246,867 A | 9/1993 | Lakowicz et al. |
| 5,263,480 A | 11/1993 | Wernicke et al. |
| 5,282,468 A | 2/1994 | Klepinski |
| 5,292,344 A | 3/1994 | Douglas |
| 5,299,569 A | 4/1994 | Wernicke et al. |
| 5,314,495 A | 5/1994 | Kovacs |
| 5,330,507 A | 7/1994 | Schwartz |
| 5,334,221 A | 8/1994 | Bardy |
| 5,335,657 A | 8/1994 | Terry et al. |
| 5,356,425 A | 10/1994 | Bardy et al. |
| 5,368,028 A | 11/1994 | Palti |
| 5,381,075 A | 1/1995 | Jordan |
| 5,411,531 A | 5/1995 | Hill et al. |
| 5,423,872 A | 6/1995 | Cigaina |
| 5,424,209 A | 6/1995 | Kearney |
| 5,427,935 A | 6/1995 | Wang et al. |
| 5,437,285 A | 8/1995 | Verrier et al. |
| 5,439,938 A | 8/1995 | Snyder et al. |
| 5,443,508 A | 8/1995 | Giampapa |
| 5,454,840 A | 10/1995 | Krakovsky et al. |
| 5,473,706 A | 12/1995 | Bac et al. |
| 5,487,756 A | 1/1996 | Kallesoe et al. |
| 5,507,748 A | 4/1996 | Sheehan et al. |
| 5,522,854 A | 6/1996 | Ideker et al. |
| 5,529,066 A | 6/1996 | Palti |
| 5,540,730 A | 7/1996 | Terry et al. |
| 5,540,734 A | 7/1996 | Zabara |
| 5,562,718 A | 10/1996 | Palermo |
| 5,571,150 A | 11/1996 | Wernicke et al. |
| 5,578,061 A | 11/1996 | Stroetmann et al. |
| 5,614,378 A | 3/1997 | Yang et al. |
| 5,626,134 A | 5/1997 | Zuckerman |
| 5,634,462 A | 6/1997 | Tyler et al. |
| 5,645,570 A | 7/1997 | Corbucci |
| 5,658,318 A | 8/1997 | Stroetmann et al. |
| 5,660,940 A | 8/1997 | Larsson et al. |
| 5,690,681 A | 11/1997 | Geddes et al. |
| 5,690,691 A | 11/1997 | Chen |
| 5,700,282 A | 12/1997 | Zabara |
| 5,702,444 A | 12/1997 | Struthers et al. |
| 5,707,400 A | 1/1998 | Terry et al. |
| 5,711,316 A | 1/1998 | Elsberry et al. |
| 5,716,385 A | 2/1998 | Mittal et al. |
| 5,741,334 A | 4/1998 | Mullon et al. |
| 5,755,750 A | 5/1998 | Pertuska et al. |
| 5,770,454 A | 6/1998 | Essenpreis et al. |
| 5,824,027 A | 10/1998 | Hoffer et al. |
| 5,832,932 A | 11/1998 | Elsberry et al. |
| 5,833,709 A | 11/1998 | Rise et al. |
| 5,834,005 A | 11/1998 | Usala |
| 5,836,994 A | 11/1998 | Bourgeois |
| 5,840,502 A | 11/1998 | Vlasselaer |
| 5,855,613 A | 1/1999 | Antanavich et al. |
| 5,879,709 A | 3/1999 | Soon-Shiong et al. |
| 5,902,745 A | 5/1999 | Butler et al. |
| 5,912,005 A | 6/1999 | Lanza et al. |
| 5,916,239 A | 6/1999 | Geddes et al. |
| 5,938,584 A | 8/1999 | Ardito et al. |
| 5,980,887 A | 11/1999 | Isner et al. |
| 5,985,653 A | 11/1999 | Armstrong et al. |
| 5,998,204 A | 12/1999 | Tsien et al. |
| 6,006,134 A | 12/1999 | Hill et al. |
| 6,026,326 A | 2/2000 | Bardy |
| 6,048,721 A | 4/2000 | Armstrong et al. |
| 6,049,727 A | 4/2000 | Crothall |
| 6,058,331 A | 5/2000 | King et al. |
| 6,061,582 A | 5/2000 | Small et al. |
| 6,066,163 A | 5/2000 | John |
| 6,066,497 A | 5/2000 | Powell |
| 6,073,048 A | 6/2000 | Kieval et al. |
| 6,086,525 A | 7/2000 | Davey et al. |
| 6,091,974 A | 7/2000 | Palti |
| 6,091,977 A | 7/2000 | Tarjan et al. |
| 6,091,992 A | 7/2000 | Bourgeois et al. |
| 6,093,531 A | 7/2000 | Bjornson et al. |
| 6,094,598 A | 7/2000 | Elsberry et al. |
| 6,096,532 A | 8/2000 | Armstrong et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| H1905 H | 10/2000 | Hill |
| 6,127,141 A | 10/2000 | Kopf |
| 6,134,470 A | 10/2000 | Hartlaub |
| 6,146,335 A | 11/2000 | Gozani |
| 6,161,029 A | 12/2000 | Spreigl et al. |
| 6,163,714 A | 12/2000 | Stanley et al. |
| 6,167,304 A | 12/2000 | Loos |
| 6,169,924 B1 | 1/2001 | Meloy et al. |
| 6,188,477 B1 | 2/2001 | Pu et al. |
| 6,197,534 B1 | 3/2001 | Lakowicz et al. |
| 6,205,359 B1 | 3/2001 | Boveja |
| 6,228,635 B1 | 5/2001 | Armstrong et al. |
| 6,230,061 B1 | 5/2001 | Hartung |
| 6,238,908 B1 | 5/2001 | Armstrong et al. |
| 6,240,314 B1 | 5/2001 | Plicci et al. |
| 6,254,601 B1 | 7/2001 | Burbank et al. |
| 6,261,832 B1 | 7/2001 | Law |
| 6,266,564 B1 | 7/2001 | Hill |
| 6,272,377 B1 | 8/2001 | Sweeney et al. |
| 6,292,695 B1 | 9/2001 | Webster, Jr. et al. |
| 6,294,281 B1 | 9/2001 | Heller |
| 6,319,241 B1 | 11/2001 | King et al. |
| 6,341,236 B1 | 1/2002 | Osorio et al. |
| 6,352,555 B1 | 3/2002 | Dzau et al. |
| 6,356,784 B1 | 3/2002 | Lozano et al. |
| 6,366,813 B1 | 4/2002 | DiLorenzo |
| 6,368,592 B1 | 4/2002 | Colton et al. |
| 6,381,499 B1 | 4/2002 | Taylor et al. |
| 6,400,974 B1 | 6/2002 | Lesho |
| 6,400,982 B2 | 6/2002 | Sweeney et al. |
| 6,405,079 B1 | 6/2002 | Ansarinia |
| 6,434,424 B1 | 8/2002 | Igel et al. |
| 6,449,507 B1 | 9/2002 | Hill et al. |
| 6,456,866 B1 | 9/2002 | Tyler et al. |
| 6,463,328 B1 | 10/2002 | John |
| 6,473,644 B1 | 10/2002 | Terry et al. |
| 6,493,585 B2 | 12/2002 | Plicci et al. |
| 6,511,500 B1 | 1/2003 | Rahme |
| 6,521,446 B2 | 2/2003 | Hellinga |
| 6,542,774 B2 | 4/2003 | Hill et al. |
| 6,564,096 B2 | 5/2003 | Mest |
| 6,569,428 B1 | 5/2003 | Isner et al. |
| 6,577,393 B1 | 6/2003 | Potzschke et al. |
| 6,587,704 B1 | 7/2003 | Fine et al. |
| 6,587,727 B2 | 7/2003 | Osorio et al. |
| 6,588,520 B1 | 7/2003 | Hauptmann |
| 6,600,956 B2 | 7/2003 | Maschino et al. |
| 6,602,251 B2 | 8/2003 | Burbank et al. |
| 6,605,039 B2 | 8/2003 | Houben et al. |
| 6,610,713 B2 | 8/2003 | Tracey |
| 6,625,479 B1 | 9/2003 | Weber et al. |
| 6,628,987 B1 | 9/2003 | Hill et al. |
| 6,630,154 B1 | 10/2003 | Fraker et al. |

(56) References Cited

U.S. PATENT DOCUMENTS

| | | |
|---|---|---|
| 6,650,919 B2 | 11/2003 | Edelberg et al. |
| 6,668,191 B1 | 12/2003 | Boveja |
| 6,671,556 B2 | 12/2003 | Osorio et al. |
| 6,673,595 B2 | 1/2004 | Barbera-Guillem |
| 6,676,937 B1 | 1/2004 | Isner et al. |
| 6,684,105 B2 | 1/2004 | Cohen et al. |
| RE38,525 E | 6/2004 | Stanley et al. |
| 6,764,488 B1 | 7/2004 | Burbank et al. |
| 6,767,737 B1 | 7/2004 | Wilson et al. |
| 6,780,617 B2 | 8/2004 | Chen |
| 6,790,654 B2 | 9/2004 | Malinge |
| 6,810,286 B2 | 10/2004 | Donovan et al. |
| 6,846,288 B2 | 1/2005 | Nagar et al. |
| RE38,705 E | 2/2005 | Hill et al. |
| 6,865,416 B2 | 3/2005 | Dev et al. |
| 6,895,280 B2 | 5/2005 | Meadows et al. |
| 6,907,295 B2 | 6/2005 | Gross et al. |
| 6,928,320 B2 | 8/2005 | King |
| 6,934,583 B2 | 8/2005 | Weinberg et al. |
| 6,985,774 B2 | 1/2006 | Kieval et al. |
| 7,015,037 B1 | 3/2006 | Furcht et al. |
| 7,050,846 B2 | 5/2006 | Sweeney et al. |
| 7,068,867 B2 | 6/2006 | Adoram et al. |
| 7,076,299 B2 | 7/2006 | Thong |
| 7,184,810 B2 | 2/2007 | Caduff et al. |
| 8,541,232 B2 | 9/2013 | Porat |
| 2002/0025469 A1 | 2/2002 | Heller |
| 2002/0035335 A1 | 3/2002 | Schauerte |
| 2002/0038083 A1 | 3/2002 | Houben et al. |
| 2002/0107553 A1 | 8/2002 | Hill et al. |
| 2002/0120304 A1 | 8/2002 | Mest |
| 2002/0151056 A1 | 10/2002 | Sasai et al. |
| 2003/0018367 A1 | 1/2003 | DiLorenzo |
| 2003/0040774 A1 | 2/2003 | Terry et al. |
| 2003/0044977 A1 | 3/2003 | Sakuragawa et al. |
| 2003/0045909 A1 | 3/2003 | Gross et al. |
| 2003/0050677 A1 | 3/2003 | Gross et al. |
| 2003/0078623 A1 | 4/2003 | Weinberg et al. |
| 2003/0087427 A1 | 5/2003 | Colton et al. |
| 2003/0100924 A1 | 5/2003 | Foreman et al. |
| 2003/0134346 A1 | 7/2003 | Amiss et al. |
| 2003/0148512 A1 | 8/2003 | Fanslow et al. |
| 2003/0166271 A1 | 9/2003 | Chen-Bettecken |
| 2003/0195574 A1 | 10/2003 | Osorio et al. |
| 2003/0216759 A1 | 11/2003 | Burbank et al. |
| 2003/0216775 A1 | 11/2003 | Hill et al. |
| 2003/0229380 A1 | 12/2003 | Adams et al. |
| 2003/0232370 A1 | 12/2003 | Trifiro |
| 2003/0233129 A1 | 12/2003 | Matos |
| 2003/0236558 A1 | 12/2003 | Whitehurst et al. |
| 2004/0001807 A1 | 1/2004 | Edelberg et al. |
| 2004/0048375 A1 | 3/2004 | Alt |
| 2004/0048795 A1 | 3/2004 | Ivanova et al. |
| 2004/0059392 A1 | 3/2004 | Parramon et al. |
| 2004/0091757 A1 | 5/2004 | Wang et al. |
| 2004/0097788 A1 | 5/2004 | Mourlas et al. |
| 2004/0109302 A1 | 6/2004 | Yoneda et al. |
| 2004/0126879 A1 | 7/2004 | Schneider et al. |
| 2004/0136973 A1 | 7/2004 | Huberman et al. |
| 2004/0138721 A1 | 7/2004 | Osorio et al. |
| 2004/0138822 A1 | 7/2004 | Rambau |
| 2004/0152958 A1 | 8/2004 | Frei et al. |
| 2004/0158119 A1 | 8/2004 | Osorio et al. |
| 2004/0162594 A1 | 8/2004 | King |
| 2004/0172075 A1 | 9/2004 | Shafer et al. |
| 2004/0199210 A1 | 10/2004 | Shelchuk |
| 2004/0215289 A1 | 10/2004 | Fukui et al. |
| 2004/0228847 A1 | 11/2004 | Goldschmidt et al. |
| 2004/0228897 A1 | 11/2004 | Zhang et al. |
| 2004/0243182 A1 | 12/2004 | Cohen et al. |
| 2004/0249416 A1 | 12/2004 | Yun et al. |
| 2005/0003534 A1 | 1/2005 | Huberman et al. |
| 2005/0113852 A1 | 5/2005 | Burbank et al. |
| 2005/0118726 A1 | 6/2005 | Schultz et al. |
| 2005/0131467 A1 | 6/2005 | Boveja |
| 2005/0187584 A1 | 8/2005 | Denker et al. |
| 2005/0209556 A1 | 9/2005 | Tresco et al. |
| 2005/0222644 A1 | 10/2005 | Killian et al. |
| 2005/0260158 A1 | 11/2005 | Huberman et al. |
| 2005/0272152 A1 | 12/2005 | Xu et al. |
| 2006/0000479 A9 | 1/2006 | Burbank et al. |
| 2006/0015153 A1 | 1/2006 | Gliner et al. |
| 2006/0052831 A1 | 3/2006 | Fukui |
| 2006/0074450 A1 | 4/2006 | Boveja |
| 2006/0110374 A1 | 5/2006 | Czeiger |
| 2006/0129205 A1 | 6/2006 | Boveja et al. |
| 2007/0004974 A1 | 1/2007 | Nagar et al. |
| 2007/0066877 A1 | 3/2007 | Arnold et al. |
| 2008/0220466 A1 | 9/2008 | Fulga |
| 2008/0317719 A1 | 12/2008 | Fulga |
| 2008/0318314 A1 | 12/2008 | Fulga |
| 2010/0291610 A1 | 11/2010 | Porat |

FOREIGN PATENT DOCUMENTS

| | | |
|---|---|---|
| WO | WO 87/06233 | 10/1987 |
| WO | WO 87/06233 A1 | 10/1987 |
| WO | WO 91/09312 A1 | 6/1991 |
| WO | WO 98/19712 | 5/1998 |
| WO | WO 01/50983 A1 | 1/2001 |
| WO | 01/30981 | 5/2001 |
| WO | WO 01/94420 | 12/2001 |
| WO | WO 03/010303 | 2/2003 |
| WO | WO 03/011445 A2 | 2/2003 |
| WO | WO 03/016507 | 2/2003 |
| WO | WO 03/018760 | 3/2003 |
| WO | WO 03/023022 | 3/2003 |
| WO | WO 03/055989 | 7/2003 |
| WO | WO 03/078610 | 9/2003 |
| WO | WO 03/090512 | 11/2003 |
| WO | WO 2004/028358 A1 | 4/2004 |
| WO | WO 2004/051774 A2 | 6/2004 |
| WO | WO 2004/055989 | 7/2004 |
| WO | WO 2004/089465 A1 | 7/2004 |
| WO | WO 2005/053523 A1 | 6/2005 |
| WO | WO 2005/078073 A2 | 8/2005 |
| WO | WO 2005/120090 | 12/2005 |
| WO | WO 2005/120090 A2 | 12/2005 |
| WO | WO 2006/006166 A2 | 1/2006 |
| WO | 2006/064501 | 6/2006 |
| WO | WO 2006/064504 | 6/2006 |
| WO | WO 2006/097933 A2 | 9/2006 |
| WO | WO 2007/102162 A2 | 9/2007 |
| WO | WO 2008/018079 A2 | 2/2008 |

OTHER PUBLICATIONS

An Office Action dated Dec. 19, 2013, which issued during the prosecution of U.S. Appl. No. 11/820,991.

Canadian Office Action issued Mar. 31, 2014 in CA application No. 2,632,834.

An Office Action dated Jul. 15, 2011, which issued during the prosecution of U.S. Appl. No. 11/628,488.

Dooley et al. "Granulocyte—Monocyte progenitor cells from human peripheral blood: modulation of growth in vitro by T lymphocytes and monocytes", International Journal of Cell Cloning; 1988, 6:45-59.

Graziani-Bowering et al, Journal of Immunological Methods, 207, pp. 157-168, 1997.

Chau et al. "Effect of L-phenylalanine methyl ester on the colony formation of hematopoietic progenitor cells from human bone marrow", International Journal of Cells Cloning, 1991, 9:211-219.

Ficoll definition: 2 pages. Download 2011.

An Office Action dated Feb. 12, 2011, which issued during the prosecution of European Patent Application No. 07 713 328.8.

Andrews et al. "Enrichment of fetal nucleated cells from maternal blood: model test system using cord blood", Prenatal Diagnosis, 1995, 15:913-919.

BD technical Data Sheet (2003) pp. 1-4.

An Office Action dated Nov. 21, 2011, which issued during the prosecution of U.S. Appl. No. 11/628,488.

(56) References Cited

OTHER PUBLICATIONS

An Advisory Action dated Feb. 28, 2012, which issued during the prosecution of U.S. Appl. No. 11/628,488.
Pertoft "Fractionation of cells and subcellular particles with Percoll", Journal of Biochem and Biophy. Methods, 2000, 44:1:-30.
An Office Action dated Sep. 26, 2013, which issued during the prosecution of European Patent Application No. 07 713 328.8.
De Almeida M C et al:"A simple method for Human Peripheral Blood Monocyte Isolation", Memorias Do Instituto Oswaldo Cruz, Rio De Janeiro, BR, vol. 95, No. 2,Jan. 1, 2000, pp. 221-223, XP003023526.
An Office Action dated Nov. 4, 2013, which issued during the prosecution of Canadian Patent Application No. 2,632,836.
An Office Action dated Jul. 26, 2013, which issued during the prosecution of European Patent Application No. 10190450.6.
An Office Action dated Jul. 31, 2013, which issued during the prosecution of Canadian Patent Application No. 2,645,142.
An Examination Report dated Nov. 3, 2008, which issued during the prosecution of Applicant's European Patent Application No. 05 81 7653.
An Office Action dated Jan. 22, 2013, which issued during the prosecution of U.S. Appl. No. 11/820,975.
An Office Action dated Oct. 18, 2012, which issued during the prosecution of Canadian Patent Application No. 2,632,836.
An Office Action dated Nov. 6, 2012, which issued during the prosecution of U.S. Appl. No. 12/224,913.
Response to an Office Action filed on Jan. 31, 2013, which issued during the prosecution of U.S. Appl. No. 12/224,913 with Exhibits A-D.
An Office Action dated Apr. 19, 2013, which issued during the prosecution of Canadian Patent Application No. 2,632,834.
An English Translation of an Office Action dated Jul. 26, 2012 which issued during the prosecution of Korean Patent Application No. 10-2007-7000060.
An Office Action dated Feb. 8, 2012, which issued during the prosecution of Canadian Patent Application No. 2,567,578.
An English translation of Office Action dated Aug. 30, 2011, which issued during the prosecution of Japanese Patent Application No. 2007-514327.
Repnik, et al. Journal of Immunological Methods, vol. 278,pp. 283-292, 2003.
Urbich, et al., Circulation, vol. 108,pp. 2511-2516,2003.
Challen, et al., Plos One, vol. 3, Issue 6:1-9(2008)."Promiscuous Expression of H2B-GFT Transgene in Hematopoietic Stem Cells".
Steidl, et al. Blood, 104:81-88 (2004). "Primary human CD34+ hematopoietic stem and progenitor cells express functionally active receptors of neuromediators".
Supplementary Search Report issued Aug. 1, 2008 in connection with the European Patent Application No. 05745232.8.
Examination Report issued Nov. 19, 2010 in connection with European Patent Application No. 05745232.8.
An International Search Report and a Written Opinion both dated Dec. 18, 2008, which issued during the prosecution of Applicant's PCT/IL2007/000308.
An International Preliminary Report on Patentability dated Mar. 10, 2009, which issued during the prosecution of Applicant's PCT/IL2007/000308.
An Examination Report dated Oct. 13, 2011, which issued during the prosecution of Applicant's European Patent Application No. 10190450.
An International Preliminary Report on Patentability dated Jun. 19, 2007, which issued during the prosecution of Applicant's PCT/IL2005/001348.
An International Search Report dated May 15, 2007, which issued during the prosecution of Applicant's PCT/IL2005/001348.
Written Opinion dated May 15, 2007, which issued during the prosecution of Applicant's PCT/IL2005/001348.
An Office Action dated May 17, 2010, which issued during the prosecution of U.S. Appl. No. 11/820,991.
Restriction Requirement dated Sep. 4, 2009, which issued during the prosecution of U.S. Appl. No. 11/820,991.
Restriction Requirement dated Nov. 23, 2010, which issued during the prosecution of U.S. Appl. No. 11/820,991.
An Office Action dated Mar. 2, 2011, which issued during the prosecution of U.S. Appl. No. 11/820,991.
An Office Action dated Sep. 15, 2010, which issued during the prosecution of U.S. Appl. No. 11/820,975.
An Office Action dated Feb. 21, 2013, which issued during the prosecution of Canadian Patent Application No. 2,567,578.
Kalka et al, Proceedings of the National Academy of Sciences, 97(7), pp. 3422-3427, Mar. 28, 2000.
An Office Action dated Jul. 27, 2011, which issued during the prosecution of U.S. Appl. No. 12/224,913.
Restriction Requirement dated Jan. 5, 2012, which issued during the prosecution of U.S. Appl. No. 12/224,913.
Notice of Allowance dated May 23, 2013, which issued during the prosecution of U.S. Appl. No. 12/224,913.
An Examination Report dated Mar. 31, 2011, which issued during the prosecution of Applicant's European Patent Application No. 10 19 2785.3.
Office Action dated Jun. 8, 2011, which issued during the prosecution of Applicant's European Patent Application No. 10 19 2785.3.
Office Action dated Mar. 25, 2013, which issued during the prosecution of Applicant's European Patent Application No. 10 19 2785.3.
Bernhard et al., FASEB Journal, 19:1096-110 (2005). "Cigarette smoke metal-catalyzed protein oxidation leads to vascular endothelial cell contraction by depolymerization of microtubules."
Bagley, et al, "Endothelial Precursor Cells as a Model of Turmor", Cancer Research, vol. 63, pp. 5866-5873, 2003.
Bompais, et al, "Human endothelial cells derived from circulating progenitors display specific functional properties compared with mature vessel wall endothelial cells", Blood, vol. 103, pp. 2577-2584, 2004.
Finkenzeller, et al, "Impaired in vivo vasculogenic potential of endothelial progenitor cells in comparison to human umbilical vein endothelial cells in a spheroid-based implantation model", Cell Proliferation, vol. 42, pp. 498-505, 2009.
Hu, et al, "An agiogenin-binding protein from endothelial cells", Biochemistry, vol. 88, pp. 2227-2231, 1991.
Ingram, et al, "Vessel wall-derived endothelial cells rapidly proliferate because they contain a complete hierarchy of endothelial progenitor cells", vol. 105, pp. 2783-2786, 2005.
Shim, W.S N et al., Biochem. Biophys. Res. Comm. Nov. 2004, vol. 324, pp. 481-488.
An Office Action dated Jun. 4, 2012, which issued during the prosecution of Canadian Patent Application No. 2,632,834.
Graham J.M. et al., Peer Reviewed Protocol, vol. 2 pp. 1540-1543, 2002.
Aoki M et al., Stem Cells, vol. 22, pp. 994-1002, 2004.
An Examination Report dated Dec. 2, 2011, which issued during the prosecution of Applicant's European App No. 07713328.
Hur J. et al. "Characterization of two types of Endothelial progenitor cells and their different contribution to neovasculargenesis", Hypertension, 2004; 24:1-6.
Koch A E et al.. "Interleukin-B as a Macrophage-Derived mediator of Angiogenesis" Science, vol. 258, pp. 1798-1801, 1992.
Eggermann J et al. "Endothelial progenitor cell culture and differentiation in vitro: a methodological comparison using human umbilical cord blood" Cadiovascular Research, Oxford University Press, vol. 58 No. 2, pp. 478-486, 2003.
Extended European Search Report dated Jan. 12, 2010 which issued during the prosecution of Applicant's EP Application No. 07713328.8.
Communication pursuant to Article 94(3) EPC dated Nov. 15, 2010 which issued during the prosecution of Applicant's EP Application No. 07713328.8.
Office Action dated Jun. 16, 2011, which issued during the prosecution of Singapore Patent Application No. 200806543-5.
A Restriction Requirement dated May 4, 2011, which issued during the prosecution of Applicant's U.S. Appl. No. 11/628,488.
Martin, et al., "Gradient separation of granulocytic progenitor cells (CFUc) from human blood mononuclear leukocytes", Exp. Hematol. 1985. 13:79-86.

(56) References Cited

OTHER PUBLICATIONS

Schechner et al., FASEBJ, 17(15):2250-60 (2003). "Engraftment of a vascularized human Skin equivalent."
Schnurch et al., Development, 119:957 (1993). "Expression of Tie-2, a membrane of a novel family of receptor tyrosine kinases, in the endothelial cell lineage."
Seiler et al., Circulation, 104:2012 (2001). "Promotion of collateral growth by granulocyte-macrophage colony-stimulating factor in patients with coronary artery disease: a randomized, double-blind placebo-controlled study."
Shen et al., Science, 34 (2004). "Endothelial cells stimulate self-renewal and expand neurogenesis of neural stem cells."
Shim et al., Biochemical and Biophysical Research Communications, Academic Press Inc., 324(2):461-468 (2004). "Ex vivo differentiation of human adult bone marrow stem cells into cardiomyocyte-like cells."
Shintani et al., Circulation, 103(6):897-903 (2001). "Augmentation of postnatal neovascularization with autologous bone marrow transplantation."
Shintani et al., Circulation, 103:2776-79 (2001). "Mobilization of endothelial progenitor cells in patients with acute myocardial infarction."
Singleton, J.R., Diabetes, 52:2867-2873 (2003). "Microvascular complications of impaired glucose tolerance."
Stamm et al., Lancet, 361 (9351):45-6 (2003). "Autologous bone-marrow stem-cell transplantation for myocardial regeneration."
Strauer et al., Circulation, 106(15):1913-8 (2002). "Repair of infarcted myocardium by autologous intracoronary mononuclear bone marrow cell transplantation in humans."
European Search Report issued Jan. 11, 2011—European Patent Application No. 10 190450.
Takahashi et al., Nat Med, 5:434-38 (1999). "Ischemia- and cytokine-induced mobilization of bone marrow-derived endothelial progenitor cells for neovascularization."
Takeshita et al., J Clin Invest, 93:662 (1994). "Therapeutic angiogenesis."
Taylor et al., Nat Med, 4(8):929-33 (1998). "Regnerating functional myocardium: improved performance after skeletal myoblast transplantation."
Terman et al., Biochem Biophys Res Commun, 187:1579 (1992). "Identification of the KDR tyrosine kinase as receptor for vascular endothelial cell growth factor."
Thompson et al., J am Coll Cardiol, 41(11):1964-71 (2003). "Percutaneous transvenous cellular cardiomyoplasty, A novel nonsurgical approach for myocardial cell transplantation."
Toma et al., Circulation, 105:93 (2002). "Human mesenchymal stem cells differentiate to a cardiomyocyte phenotype in the adult murine heart."
Tomita et al., Circulation, 100 (19 Suppl):11247-56 (1999). "Autologous transplantation of bone marrow cells improves damaged heart function."
Tomita et al., J Thorac Cardiovasc Surg, 123(6):1132-40 (2002). "Improved heart function with myogenesis nd angiogenesis after autologous porcine bone marrow stromal cell transplantation."
Czeiger et al. U.S. Appl. No. 60/631,098, filed Nov. 24, 2004, published May 25, 2006.
Porat et al. U.S. Appl. No. 60/780,761, filed Mar. 8, 2006, published Sep. 13, 2007.
Zheng et al., Circ Res, 90:284-288 (2002) "Bone marrow-derived endothelial progenitor cells participate in cerebral neovascularization after focal cerebral ischemia in the adult mouse."
Urbich et al., Circulation Research, 95:343-353 (2004). Endothelial progenitor cells: characterization and role in vascular biology.
Verma et al., Circulation, 109(17):2058-67 (2004). "C-reactive protein attenuates endothelial progenitor cell survival, differentiation, and function: further evidence of a mechanistic link between c-reactive protein and cardiovascular disease."
Wagers et al., Science, 297(5590), (2002). "Little evidence for developmental plasticity of adult hematopoietic stem cells."

Wagers et al., Science, 297:2256-2259 (2002). "Little evidence for developmental plasticity of adult hematopoietic stem cells."
Wang et al., Am J Physiol Heart Circ Physiol, 286(5):H1985-93 (2004). "Mechanical, cellular, and molecular factors interact to modulate circulating endothelial cell progenitors."
Wang et al., Circulation, 109(11):1392-400 (2004). "Rosiglitazone facilitates angiogenic progenitor cell differentiation toward endothelial lineage: a new paradigm in glitazone pleiotropy."
Ward, Drug Discovery World, 33-38 (2003). "Automating cell culture to optimise cell line generation and selection."
Written Opinion of the International Searching Authority issued by the International Searching Authority (ISA/US) on May 15, 2007 in connection with International Application No. PCT/IL2005/001345.
Yeh et al., Circulation, 108(17):2070-2073 (2003). "Transdifferentiation of human peripheral blood CD34+ enriched cell population into cardiomyocytes, endothelial cells, and smooth muscle cells in vivo."
Zhang et al., Circ Res, 90:284-88 (2002). "Bone marrow-derived endothelial progenitor cells participate in cerebral neovascularization after focal cerebral ischemia in the adult mouse."
Zhao et al., Exp Neurol, 172:11-20 (2002). "Human bone marrow stem cells exhicit neural phenotypes and ameliorate neurological deficits grafting into the ischemic brain of rats."
Price, et al., "Multipotent Adult Progenitor Cell Lines Originating from the Peripheral Blood of Green Fluorescent Protein Transgenic Swine", Stem Cells and Development 15:507-522 (2006).
Heeschen et al., Blood, 102(4):1340-6 (2003), "Erythropoietin is a potent physiologic stimulus for endothelial progenitor cell mobilization."
Hao et al., Hematother Stem Cell Res, 12:23-32 (2003). "Fetal human hematopoietic stem cells can differentiate sequentially into neural stem cells and then astrocytes in vitro."
Harrison et al., Blood, 99:394 (2002). "Oxygen saturation in the bone marrow of healthy volunteers."
Grant et al., Nat Med, 8(6):607-12 (2002). "Adult hematopoietic stem cells provide functional hemangioblast activity during retinal neovascularization."
Goolsby et al., PNAS USA, 100(25):14926-14931 (2003). "Hematopoietic progenitors express neural genes."
Gojo et al., Exp Cell Res, 288:51 (2003). "In vivo cardiovasculogenesis by direct injection of isolated adult mesenchymal stem cells."
Fulga et al., 2004-006-01, U.S. Appl. No. 60/576,266, published Dec. 15, 2005.
Porat et al., Dec. 14, 2004, U.S. Appl. No. 60/636,391, published Jun. 22, 2006.
Belkin et al., Jun. 2, 2005, U.S. Appl. No. 60/685,115, published Jul. 12, 2006.
Porat, U.S. Appl. No. 60/668,739, published Jun. 22, 2006.
Fulga et al., U.S. Appl. No. 60/588,520, published Dec. 15, 2005.
Aicher et al., Circulation, 107:2134-2139 (2003). "Assessment of the tissue distribution of transplanted human endothelial progenitor cells by radioactive labeling."
Akita et al., Lab Invest, 83(1):65-73 (2003). "Hypoxic preconditioning augments efficacy of human endothelial progenitor cells for therapeutic neovascularization."
Akiyama et al., Neuroscience, 22:6623-6630 (2002). "Remyelination of the rat spinal cord by transplantation of identified bone marrow stromal cells."
Amann-Vesti et al., Dermatol Surg, 30(3):399 (2004). "Microangiopathy of split-skin grafts in venous ulcers."
Andrews et al., Blood, 67:842 (1986). "Monoclonal antibody 12-8 recognizes a 115-kd molecule present on both unipotent and multipotent hematopoietic colony-forming cells and their precursors."
Asahara et al., Circ Res, 85:221-28 (1999). "Bone marrow origin of endothelial progenitor cells responsible for postnatal vasculogenesis in physiological and pathological neovascularization."
Asahara et al., EMBO J, 18:3964-72, Circulation 107:3059-65 (1999). "VEGF contributes to postnatal neovascularization by mobilizing bone marrow-derived endothelial progenitor cells."

(56) References Cited

OTHER PUBLICATIONS

Badorff et al., Circulation, 107(7):1024-32 (2003). "Transdifferentiation of blood-derived human adult endothelial progentiro cells into functionally active cardiomyocytes."
Baffour et al., J Vasc Surg. 16:181 (1992). "Enhanced angiogenesis and growth of collaterals by in vivo administration of recombinant basic fibroblast growth factor in a rabbit model of acute lower limb ischemia dose-response effect of fibroblast growth factor."
Bahlmann et al., Kidney Int. 64(5):1648-52 (2003). "Endothelial progenitor cell proliferation and differentiation is regulated by erythropoietin."
Bahlmann, Blood, 103(3):921-6 (2004). "Erythropoietin regulates endothelial progenitor cells."
Bhattacharya et al., Blood, 95(2):581-5 (2000). "Enhanced endothelialization and microvessel formation in polyester grafts seeded with CD34+ bone marrow cells."
Biernaskie et al., Nature Protocols, 1(6) (2006). "Isolation of skin-derived precursors (SKPs) and differentiation and enrichment of their schwann cell progency."
Bonilla et al., Eur J Neurosci, 15:575-582 (2002). "Haematopoietic progenitor cells from adult bone marrow differentiate into cells that express oligodendroglial antigens in the neonatal mouse brain," (Abstract only).
Cao et al., Cancer, 91(12):2205-2213 (2001). "Rapid engraftment after allogenetic transplantation of density-enriched peripheral blood CD34+ cells in patients with advanced ehmatologic malignncies."
Castro et al., Science, 297(5585):1299 (2002). "Failure of bone marrow cells to transdifferentiate into neural cells in vivo."
Ceradini et al., Nature Med, 10:858-864 (2004). "Progenitor cell trafficking is regulated by hypoxic gradients through Hef-1 induction of Sdf-1."
Chen et al., J Trauma, 31(9):1286-93 (1991). "Four types of venous flaps for wound coverage: a clinical appraisal."
Chen et al., Stroke, 32:1005-1011 (2001). "Therapeutic benefit of intravenous administration of bone marrow stromal cells after cerebral ischemia in rats."
Condorelli et al., PNAS, 98(19):10733-10738 (2001). "Cardiomyocytes induce endothelial cells to trans-differentiate into cardiac muscle: implications for myocardium regeneration."
Corti et al., Exp Neurol, 177:443-452 (2002). "Modulated generation of neuronal cells from bone marrow by expansion and mobilization of circulating stem cells with in vivo cytokine treatment." (Abstract only).
Davani et al., Circulation, 108:II253 (2003). "Mesenchymal progenitor cells differentiate into an endothelial phenotype, enhance vascular density, and improve heart function in a rat cellular cardiomyoplasty model."
Di Stefano et al., Cardiovasc Radiat Med, 3(3-4):172-5 (2002). "Different growth conditions for peripheral blood endothelial progenitors."
Dimmeler et al., J Clin Invest, 108:391-397 (2001). "HMG-Coa reducatse inhibitors (statins) increase endothelial progenitor cells via the PI 3-kinase/Akt pathway."
Eglitis et al., Neuroreport, 10:1289-1292 (1999). "Targeting of marrow-derived astrocytes to the ischemic brain." (Abstract only).
Eglitis,M.A. and Mezey, E., PNAS USA, 94:4080-4085 (1997). "Hematopoietic cells differentiation into both microglia and macroglia in the brains of adult mice."
European Examination Report issued Dec. 21, 2009—European Patent Application No. 05817711.
European Examination Report issued Nov. 18, 2008—European Patent Application No. 05817711.
European Search Report issued Aug. 4, 2008—European Patent Application No. 05817711.
Gill et al., Circ Res. 68:167-74 (2001). "Vascular trauma induces rapid but transient mobilization of VEGF2+AC133+ endothelial precursor cells."
Examination Report dated Nov. 30, 2009—European Patent Application No. 05 81 7653.
Examination Report issued Sep. 30, 2010—European Patent Application No. 05 817 653.8.
Examiner's first report on Australian Patent Application No. 2006253728, dated Sep. 22, 2010.
Extended European Search Report dated Jul. 30, 2008, which issued during prosecution of European Patent Application No. 05 81 7653.
Ferrero et al., p. 123b (2001). "Mobilised peripheral blood progenitor cells give rise in vitro to cells expressing neuronal phenotype." (Abstract only).
Ferretti et al., Life Sci, 73:1985-94 (2003). "Angiogenesis and nerve regeneration in a model of human skin equivalent transplant."
Flammer et al., Progress in Retinal and Eye Research, 21:359-393 (2002). "The impact of ocular blood flow in glaucoma."
Folkman et al., J Biol Chem, 267:10931 (1992). "Angiogenesis."
Forbes et al., Clinical Science, 103:355-369 (2002). "Adult stem cell plasticity: new pathways of tissue regeneration become visible."
Frank, R.N., N Engl J Med, 350:48-58 (2004). "Diabetic retinopathy."
Franz et al., The Lancet, 362:675-676 (2003). "Stem-cell homing and tissue regeneration in ischaemic cardiomyopathy."
Gazitt et al., Stem Cells, 19(2):134-143 (2001). "Expression of adhesion molecules on CD34+ cells in peripheral blood of non-Hodgkin's lymphoma patients mobilized with different growth factors."
Hershfinkel et al., PNAS USA, 98:1749-1754 (2001). "A zinc-sensing receptor triggers the release of intracellular Ca2+ and regulates ion transport."
Hess et al., Stroke, 33:1362-1368 (2002). "Bone marrow as a source of endothelial cells and neuN-expressing cells after stroke."
Hirata et al., Am J Physiol Heart Circ Physiol, 284(1):H66-70 (2003). "Autologous bone marrow cell implantation as therapeutic angiogenesis for ischemic hindlimb in diabetic rat model."
Hofstetter et al., PNAS USA, 99:2199-2204 (2002). "Marrow stromal cells from guiding strands in the injured spinal cord and promote recovery."
Hristov et al., Blood, first edition paper, DOI 10.1182/blood-2003-10-3614 (2004). "Adoptotic bodies from endothelial cells enhance the number and initiate the differentiation of human endothelial progenitor cells in vitro."
Hunt et al., Current Opinion in Biotechnology, 20:522-530 (2009). "Multipotent skin-derived precursors: from biology to clinical translation."
Ikenaga et al., J Surg Res, 96(2):277-83 (2001). "Autologous bone marrow implnatation induced angiogenesis and improved deteriorated exercise capacity in a rat ischemic hindlimb model."
International Preliminary Report on Patentability issued by the International Bureau of WIPO dated Jun. 19, 2007 in connection with International Application No. PCT/IL2005/001345.
International Search Report issued by the International Searching Authority (ISA/US) on May 15, 2007 in connection with International Application No. PCT/IL2005/001345.
Isner et al., Lancet, 348:370 (1996). "Clinical evidence of angiogenesis after arterial gene transfer of phVEGF in patient with ischaemic limb."
Kalka et al., Ann Thorac Surg, 70:829-34 (2000). VEGF gene transfer mobilizes endothelial progenitor cells in patients with inoperable coronary disease.
Kalka et al., Circ Res, 86(12):1198-202 (2000). "Vascular endothelial growth factor (165) gene transfer augments circulating endothelial progenitor cells in human subjects,".
Kamihata et al., Circulation, 104(9):1046-52 (2001). "Implantation of bone marrow mononuclear cells into ischemic myocardium enhances collateral perfusion and regional function via side supply of angioblasts, angiogenic ligands, and cytokines."
Kang et al., The Lancet, 363:751-756 (2003). "Effects of intracoronary infusion of peripheral blood stem-cells mobilized with granulocyte-colony stimulating factor on left ventricular systolic function and restenosis after coronary stenting in myocardial infraction: the Magic cell randomized clinical trial."
Katz et al., Leuk Res, 9:191 (1985). "Identification of a membrane glycoprotein assoicated with haemopoietic progenitor cells."
Kaushal et al., Na Med, 7(9):1035-40 (2001). "Functional small-diameterneovessels created using endothelial progenitor cells expanded ex vivo."

(56) References Cited

OTHER PUBLICATIONS

Kawamoto et al., Circulation, 103(5):634-7 (2001). "Therapeutic potential of ex vivo expanded endothelial progenitor cells for myocardial ischemia."
Kocher et al., Nat Med, 7:430-36 (2001). "Neovascularization of ischemic myocardium by human bone marrow-derived angioblasts prevents cardiomyocyte apoptosis, reduces remodeling and improves cardiac function."
Kornowski et al., J Am Coll Cardiol, 35(4):1031-9 (2000). "Electromagnetic guidance for catheter-based transendocardial injection: a platform for intramyocardial angiogenesis therapy. Results in normal and ischemic procine models."
Kouwenhoven et al., Transplant Internat, 13(6):385-401 (2000). "Etiology and pathophysiology of chronic transplant dysfunction."
Li et al., Ann Thorac Surg, 62(3):654-60 (1996). "Cardiomyocyte transplantation improves heart function."
Li et al., J Cereb Blood Flow Melab, 20:1311-1319 (2000). "Intrastriatal transplantation of bone marrow nonhematopoietic cells improves functional recovery after stroke in adult mice."
Li et al., Neurology, 56:1666-1672 (2001a). "Treatment of stroke in rat with intracarotid administration of marrow stromal cells." (Abstract only).
Li et al., Neurosci Lett. 316:67-69 (2001b). "Intracerebral transplantation of bone marrow stromal cells in a 1-methyl-4-phenyl-1-,2,3,6-tetrahydropyridine mouse model of Parkinson's Disease." (Abstract only).
Liesveld et al., Leukemia, 8:2111 (1994). "Characterization of the adherence of normal and leukemic CD34+ cells to endothelial monolayers."
Liouterman et al., p. 632 (2001). "Transplantation of human hematopoietic stem cells in rat brain: analysis of cell survival and differentiation."
Mahmood et al., Neurosurgery, 49:1196-1203 (2001). "Treatment of traumatic brain injury in female rats with intravenous administration of bone marrow stromal cells." (Abstract only).
Millauer et al., Cell, 72:835 (1993). "High affinity VEGF binding and developmental expression suggest Flk-1 as a major regulator of vasculogenesis and angiogenesis."
Newman et al., Science, 247:1219 (1990). PECAM-1 (CD31) cloning and relation to adhesion molecules of the immunoglobulin gene superfamily>.
Nishida et al., N Engl J Med, 351:1187-1196 (2004). "Corneal reconstruction with tissue-engineered cell sheets composed of autologous oral mucosal epithelium."
Norol et al., Blood, 102:4361 (2003). "Influence of mobilized stem cells on myocardial in farctrepair in a nonhuman primate model."
Nygren et al., Nature Medicine, 10(5):494-501 (2004). "Bone marrow-derived hematopoietic cells generate cardiomyocytes at a low frequency through cell fusion but not transdifferentiation."
Orlic et al., PNAS USA, 98: 10344 (2001), "Mobilized bone marrow cells repair the infarcted heart, improving function and surivival."
Ortiz-Gonzalez et al., Current Neurovascular Research, 1(3):207-213 (2004). "Neural induction of adult bone marrow and umbilical cord stem cells."
Patel, A., University of Pittsburgh, Abstract from American Association for Thoracic Surgery, Toronto, May 2004.
Payne, A.G., Medical Hypotheses, 62:718-720 (2004). "Using immunomagnetic technology and other means to facilitate stem cell homing."
Penn et al., International Journal of Cardiology, 95 Suppl. 1:S23-S25 (2004). "Role of stem cell homing in myocardial regeneration."
Perin et al., Circulation, 107(18):2294-302 (2003). "Transendocardial, autologous bone marrow cell transplanation for severe, chronic ischemic heart failure."
Porat et al., British Journal of Haematology, 135:703-714 (2006). "Isolation of an adult blood-derived progenitor cell population capable of differentiation into angiogenic, myocardial and neural lineages."

Priller et al., J Cell Biol, 155:733-738 (2001b). "Neogenesis of cerebellar purkinje neurons from gene-marked bone marrow cells in vivo."
Priller et al., Nat Med, 7:1356-1361 (2001a). "Targeting gene-modified hematopoietic cells to the central nervous system: Use of green fluorescent protein uncovers microglial engraftment."
Quesenberry et al., Blood Cells, Mulecules and Diseases, 32:1-4 (2004), "Stem cell plasticity: an overview."
Quirici et al., Br J Haematol, 115(1):186-94 (2001). "Differentiation and expansion of endothelial cells from human bone marrow CD133+ cells."
Rafii et al., Nat Med. 9(6):702-12 (2003). "Therapeutic stem and progenitor cell transplantation for organ vascularization and regeneration."
Rajnoch et al., J Thorac Cardiovasc Surg. 121(5):871-8 (2001). "Cellular therapy reverses myocardial dysfunction."
Schatteman et al., J Clin Invest. 106(4):571-8 (2000). "Blood-derived angloblasts accelerate blood-flow restoration in diabetic mice."
Rupp et al., Basic Res Cardiol, 99(1):61-8 (2004). "Statin therapy in patients with coronary artery disease improves the impaired endothelial progenitor cell differentiation into cardiomyogenic cells."
Sato et al., Exp Cell Res, 204:223 (1993). "Indispensable role of tissue-type plasminogen activator in growth factor-dependent tube formation of human microvasular endothelial cells in vitro."
Sato et al., Nature, 376:70 (1995). "Distinct roles of the receptor tyrosine kinases Tie-1 and Tie-2 in blood vessel formation."
Rehman, et al. "Exercise Acutely Increases Circulating Endothelial Progenitor Cells and Monocyte- /Macrophage-Derived Angiogenic Cells" *Journal of the American College of Cardiology*, vol. 43, Issue 12, Jun. 16, 2004, pp. 2314-2318.
Reinecke, et al. "Skeletal Muscle Stem Cells Do Not Transdifferentiate Into Cardiomyocytes After Cardiac Grafting", *J. Cell Mol Cell Cardiology*, 24, 2002, 241-249.
Murry, et al. "Haematopoietic Stem Cells Do Not Transdifferentiate Into Cardiac Myocytes in Myocardial Infarcts", *Nature*, vol. 428, 2004, 664-668.
Office Action issued Mar. 30, 2010 in connection with U.S. Appl. No. 11/820,975, filed Jun. 20, 2007.
Office Action issued Sep. 15, 2010 in connection with U.S. Appl. No. 11/820,975, filed Jun. 20, 2007.
Office Action issued May 17, 2010 in connection with U.S. Appl. No. 11/820,991, filed Jun. 20, 2007.
Examination Report issued Oct. 8, 2010 in connection with European Patent Application No. 05 817 711.4.
Examination Report issued Dec. 8, 2008 in connection with European Patent Application No. 05 745 232.8.
Examination Report issued Nov. 6, 2009 in connection with European Patent Application No. 05 745 232.8.
Leblond, C.P. (1964) "Classification of Cell Populations on the Basis of Their Proliferative Behavior" Natl. Cancer Inst. Monogr. 14:119-150.
Kocher, et al. "Myocardial Homing and Neovascularization by Human Bone Marrow Angioblasts Is Regulated by IL-8/Gro CXC Chemokines", J Mol Cell Cardiol. Epub Jan. 24, 2006 vol. 40 No. 4 p. 455-64. Abstract only.
Hur, et al.,"Characterization of Two Types of Endothelial Progenitor Cells and Their Different Contributions to Neovasculogenes", Arterioscler Thromb Vasc. Biol. Feb. 2004, vol. 24 No. 2 p. 288-293.
Evans MJ. and Kaufman M.H. (1981), "Establishment in Culture of Pluripotential Cells From Mouse Embryos", Nature 292: 154-156.
Donovan PJ. and Gearhart J. (2001) "The End of the Beginning for Pluripotent Stem Cells" Nature 414:92-97.
Leah Tolosa, et al.,"Optical Assay for Glucose Based on the Luminescnence Decay Time of the Long Wavelength Dye Cy5", Sensors and Acutators B 45 (1997) 93-99.
Spralding A. et al.,"Stem Cells Find Their Niche", Nature 414: 98-104.
Weissman I.L. et al.,"Stem and Progenitor Cells: Origins, Phenotypes, Lineage Commitments, and Transdifferentiations", Annu. Rev. Cell. Dev. Biol. 17:387-403.
Weissman L.L.,(2000)"Stem, Cells: Unit of Development, Units of Regeneration, and Units in Evolution", Cell 100: 157-68.

(56) References Cited

OTHER PUBLICATIONS

Cheng A., Wang. S., Cai J., Rao MS, Mattson MP, (2003),"Nitric Oxide Acts in a Positive Feedback Loop With BDNF to Regulate Neural Progenitor Cell Proliferation and Differentiation in the Mammalian Brain," Dev Biol. 258(2):319-33.
Cousin B, Andre M, Arnaud E, Penicaud L, Casteilla L (2003),"Reconstitution of lethally Irradiated Mice by Cells Isolated From Adipose Tissue" Biochem Biophys Res Cornmun. 301(4): 1016-22.
Anderson DJ., Gage, F.H., and Weissman, LL. (2001)."Can Stem Cells Cross Lineage Boundaries?" Nat. Med. 7:393-395.
Robey P.G. (2000),"Stem Cells Near the Century Mark" J. Clin. Invest. 105:1489-1491.
Eisenberg LM, Burns L, Eisenberg CA (2003),"Hematopoietic Cells From Bone Marrow Have the Potential to Differentiate Into Cardiomyocytes In Vitro". Anat Rec. 274A(1):870-882.
Karl J.L., Fernandes Ian A., McKenzie, Pleasantine Mill et al. (2004),"A Dermal Niche for Multipotent Adult Skin-Derived Precursor Cells," Nature Cell Biology Published online: Nov. 1, 2004, DOI: 10.1038/ncbl 181.
Jackson KA, Mi T, Goodell MA (1999),"Hematopoietic Potential of Stem Cells Isolated From Murine Skeletal Muscle." Pro Natl Acad Sci USA 96(25):14482-14486.
Brazelton TR, Rossi FM, Keshet GI, Blau HM (2000),"From Marrow to Brain: Expression of Neuronal Phenotypes in Adult Mice," Science 290(5497): 1775-1779.
Bjornson CR, Rietze RL, Reynolds BA, Magli MC, Veseovi AL (1999),"Turning Brain Into Blood: A Hematopoietic Fate Adopted by Adult Neural Stem Cells In Vivo,", Science 283(S401):534-537.
Slack, J.M. (2000)"Stem Cells in Epithelial Tissues," Science 287: 1431-1433.
Ferrari G., Cusella-De Angelis G., Coletta M., Paolucci E., Stornaiuolo A., Cossu G., and Mavilio F. (1998),"Muscle Regeneration by Bone Marrow-Derived Myogenic Progenitors", Science 279: 1528-1530.
Lagasse E, Connors H, Al-Dhalimy M, Retisma M, Osborne L, Wang X, Finegold M, Weissman IL, Grompe M (2000),"Purified Hematopoietic Stem Cells Can Differentiate Into Hepatocytes In Vivo" Nat Med. 6:1229-1234.
Hirschi K.K., and Goodell, M.A. (2002),"Hematopoietic, Vascular and Cardiac Fates of Bone Marrow-Derived Stem Cells," Gene Therap. 9:648-652.
Theise N.D., et al. (2000) "Liver From Bone Marrow in Humans" Hepatology 32:11-16.
Kleeberger W. et al.,"High Frequency of Epithelial Chimerism in Liver Transplants Demonstrated by Microdissection and STR-Analysis," Hepatology 35:110-116.
Weimann J.M. et al. (2003), "Contribution of Transplanted Bone Marrow Cells to Purkinje Neurons in Human Adult Brains," Proc. Natl. Acad. Sci. USA 100: 2088-2093.
Blau H.M. et al. (2001),"The Evolving Concept of a Stem Cell : Entity or Function?," Cell 105: 829-841.
Krause D.S. (2002),"Plasticity of Marrow-Derived Stem Cells" Gene Ther. 9:754-758.
Wulf G.G. et al. (2001),"Somatic Stem Cell Plasticity" Exp Hematol. 29: 1361-1370.
Pittenger M.F. et al. (1999),"Multilineage Potential of Adult Human Mesenchymal Stem Cells" Science 284:143-147.
Liechty K.W. et al. (2000),"Human Mesenchymal Stem Cells Engraft and Demonstrate Site-Specific Differentiation After in Utero Transplantation in Sheep," Nature Med. 6:1282-1286 XIII.
Laterveer L. et al. (1995),"Interleukin-8 Induces Rapid Mobilization of Hematopoietic Stem Cells With Radioprotective Capacity and Long-Term Myelolymphoid Repopulating Ability" Blood 85: 2269-2275.
Schömig K. Et al., (2006) "Interleukin-8 is Associated With Circulating CD133+ Progenitor Cells in Acute Myocardial Infarction," European Heart Journal 27:1032-1037.

Jang YY et al.,"Hematopoietic Stem Cells Convert Into Liver Cells Within Days Without Fusion," Nat Cell Biol. 6(6):532-539. Epub May 9, 2004.
Bittner R.E., et al. (1999),"Recruitment of Bone-Marrow-Derived Cells by Skeletal and Cardiac Muscle in Adult Dystrophic MDX Mice," Anat. Embryol. (Berl) 199:391-396.
Mezey E, et al. (200),"Turning Blood Into Brain: Cells Bearing Neuronal Antigens Generated In Vivo From Bone Marrow" Science. 290(5497):1779-1782.
Douglas W.L., Dimmeler S. (2004),"Therapeutic Angiogenesis and Vasculogenesis for Ischemic Diseases. Part I: Angiogenic Cytokines" Circulation 109:2487-2491.
Douglas W.L., Dimmeler S. (2004),"Therapeutic Angiogenesis and Vasculogenesis for Ischemic Diseases. Part II, Cell-Based Therapy" Circulation 109:2692-2697.
Amit M. et al.,"Clonally Derived Human Emryonic Stem Cell Lines Maintain Pluripotency and Proliferative Potential for Prolonged Periods of Culture," Dev Biol. 227(2):271-278.
Aoki S, Toda S, Sakemi T, Sugihara H (2003),"Culture of Endothelial Cells and Mature Adipocytes Actively Promotes Immature Preadipocyte Development In Vitro," Cell Struct Funct. 28(1):55-60.
Badorff C, et al.,"Transdifferentiation of Blood-Derived Human Adult Endothelial Progenitor Cells Into Functionally Active Cardiomyocytes," Circulation 107(7):1024-1032.
Bianco, P. and Robey P.G. (2001),"Stem Cells in Tissue Engineering" Nature 414:118-121.
Lagasse E, et al. (2001), "Toward Regenerative Medicine," Immunity 14:425-436.
Stock U.A., Vacanti J.P. (2001), "Tissue Engineering: Current State and Prospects," Ann. Rev. Med 52:443-451.
Kim W.S. et al. (1994), "Bone Defect Repair With Tissue-Engineered Cartilage," Plast. Recontr. Surg. 94:580-584.
Petite H. et al. (2000), "Tissue-Engineered Bone Regeneration" Nature Biotechnol. 18:959-963.
Ramiya V.K. et al. (2000), "Reversal of Insulin-Dependent Diabetes Using Islets Generated In Vitro From Pancreatic Stem Cells," Nature Medicine 6:278-282.
Raffi S., Lyden D.(2003), "Therapeutic Stem and Progenitor Cell Transplantation for Organ Vascularization and Regeneration," Nature Medicine 9:702-712.
Gussoni E., Soneoka Y., Strickland C., Buzney E., Khan M., Flint A., Kunkel L., and Mulligan R. (1999),"Dystrophin Expression in the MDX Mouse Restored by Stem Cell Transplantation," Nature 401390-394.
Zhao Y. et al. (2003) "A Human Peripheral Blood Monocyte-Derived Subset Acts as Pluripotent Stem Cells," Proc. Natl. Acad. Sci. USA 100:2426-2431.
Kayisli U.A., et al., "Regulation of Angiogenic Activity of Human Endometrial Endothelial Cells in Culture by Ovarian Steroids", J Clin Endocrinol Metab 89:5794-5802.
Dimmeler S. (2005), "Circulating Endothelial Precursors: Identification of Functional Subpopulations," Blood 106(7):2231-2232.
Urbich C. et al. (2004), "Endothelial Progenitor Cells: Characterization and Role in Vascular Biology," Circulation Research 95:343-353.
A. Asahara T, Murohara T, Sullivan A, et al. (1997), "Isolation of Putative Progenitor Endothelial Cells for Angiogenesis," Science 275:964-967.
B. Kalka C, Masuda H, Takahashi T et al. (2000), "Transplantation of Ex Vivo Expanded Endothelial Progenitor Cells for Therapeutic Neovascularization," Proc Natl Acad Sci USA. 97:3422-3427.
C. Assmus B, Schachinger V, Teupe C, et al. (2002), "Transplantation of Progenitor cells and Regeneration Enhancement in Acute Myocardial Infarction (TOPCARE-AMI)," Circulation. 106:3009-3017.
D. Yoon CH, Hur J., Park KW, et al. (2005), "Synergistic Neovascularization by Mixed Transplantation of Early Endothelial Progenitor Cells and Late Outgrowth Endothelial Cells," Circulation. 112:1618-1627.
E. DeLisser, H.M.,Christofidou-Solomidou, R.M. Strieter, M.D. et al. (1997), "Involvement of Endothelial PECAM-1/CD31 in Angiogenesis," Am J Pathol. 151: 671-677.

(56) References Cited

OTHER PUBLICATIONS

F. Kuwamoto A., Tkebuchava T., Yamaguchi J.I., et al. (2003),"Intramyocardial Transplantation of Autologous Endothelial Progenitor Cells for Therapeutic Neovascularization of Myocardial Ischemia," Circulation. 107:461-468.

HI. Kanayasu-Toyoda T., Yamaguchi T., Oshizawa T., et al. (2003),"CD31 (PECAM-1)-Bright Cells Derived From AC133-Positive Cells in Human Peripheral Blood as Endothelial-Precursor Cells," Journal of Cell Physiol. 195:119-129.

I. Yamamoto K. Takahashi T., Asahara T., et al. (2003), "Proliferation Differentiation and Tube Formation by Endothelial Progenitor Cells in Response to Shear Stress," J Appl Physiol. 95: 2081-2088.

Quaini F. et al. (2002), "Chimerism of the Transplanted Heart," N. Engl. Med 346:5-15.

Goodell M.A. et al. (2001), "Stem Cell Plasticity in Muscle and Bone Marrow," Ann. NY Acad. Sci. 938:208-220—an abstract.

Li A. et al. (2003), "IL-8 Directly Enhanced Endothelial Cell Survival, Proliferation, and Matrix Metalloproteinases Production and Regulated Angiogenesis", Journal of Immunol. 170:3389-3376.

Rodda SJ, Kavanagh SJ, Rathjen J, Rathgen PD (2002), "Emrbyonic Stem Cell Differentiation and the Analysis of Mammalian Development," Int J Dev Biol. 46(4):449-458—an abstract.

Wan H., An Y., Zhang Y, Wang Z (2003), "Differentiation of Rat Embryonic Neural Stem Cells Promoted by Co-Cultured Schwann Cells," Chin Med J (Engl). 116(3):428-431 39.

Kollet O, Shivtel S, Chen YQ. et al. (2003), "HGF, SDF-1, and MMP-9 Are Involved in Stress-Induced Human CD34+ Stem Cell Recruitment to the Liver" J Clin Invest. 112(2):160-169—an abstract.

Jackson KA, Majka SM, Wang H, Pocius J, Hartley CJ, Majesky MW, Entman ML, Michael LH, Hirschi KK, Goodell MA (2001). "Regeneration of Ischemic Cardiac Muscle and Vascular Endothelium by Adult Stem Cells," J Clin Invest. 107(11)1395-1402.

Kohji N, Masayuki Y, Yasutaka H. Et al. (2004)."Corneal Reconstruction With Tissue-Engineered Cell Sheets Composed of Autologous Oral Mucosal Epithelium," N Engl J Med 351:1187-1196.

G. Newman PJ. (1997), "The Biology of PECAM-1," J Clinn Invest. 99:3-8.

A.Vecchi, A., C. Garlanda, M.G. Lampugnani, M. Resnati, et al. (1994), "Monoclonal Antibodies Specific for Endothelial Cells of Mouse Blood Vessels. Their Application in the Identification of Adult and Embryonic Endothelium," Eur J Cell Biol. 63:247-254—an abstract.

J. Cohen S., and Leor J. (2004), "Rebuilding Broken Hearts," Scientific American, November: 45-51—an abstract.

Metcalf D et al., "Adherence Column and Buoyant Density Separation of Bone Marrow Stem Cells and More Differentiated Cells", Journal of Cellular Physiology, Liss, New York, vol. 78, No. 3, Jan. 1, 1971, pp. 441-450.

Asahara T et al., "Isolation of Putative Progenitor Endothelial Cells for Angiogenesis" Science, Washington DC, vol. 275. No. 5302, Feb. 14, 1997, pp. 964-967.

Kubota Yoshiaki, et al., "Transplanted Endothelial Progenitor Cells Augment the Survival Areas of Rat Dorsal Flaps", Cell Transplantation, Elsevier Science, US vol. 12, No. 6, Jan. 1, 2003, pp. 647-657.

Anonymous: "OptiPrep? Compared to Other Density Gradient Media" OptiPrep Reports, [Online] No. 3, 2000, http://www.axis-shield.com/densityhome/density/opti_prep.pdf.

B.E. Jarrell, et al., "Use of an Endothelial Monolayer on a Vascular Graft Prior to Implantation," 97th Annual Meeting of the Southern Surgical Association, Hot Springs, Virginia, Dec. 1-4, 1985.

S.K. Williams, et al.,"Adult Human Endothelial Cell Compatibility With Prosthetic Graft Material", Journal of Surgical Research 38, 618-629, 1985.

An Office Action dated Jul. 23, 2014 which issued during the prosecution of U.S. Appl. No. 11/820,991.

FIG. 8
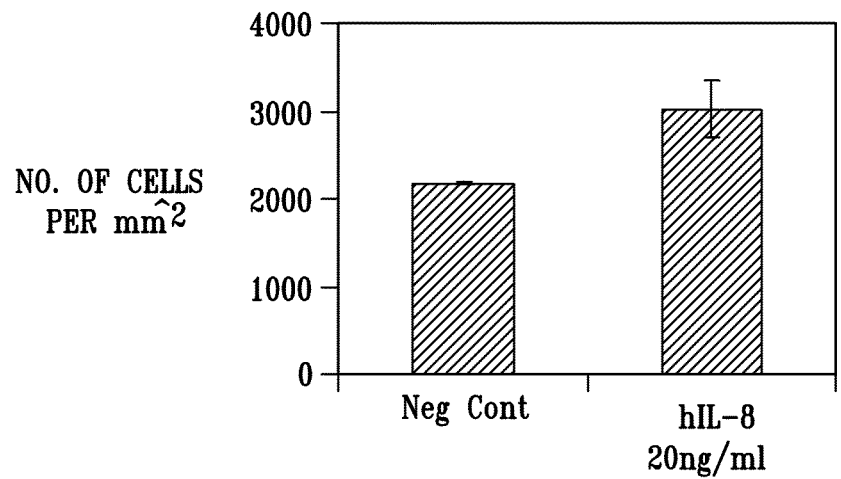
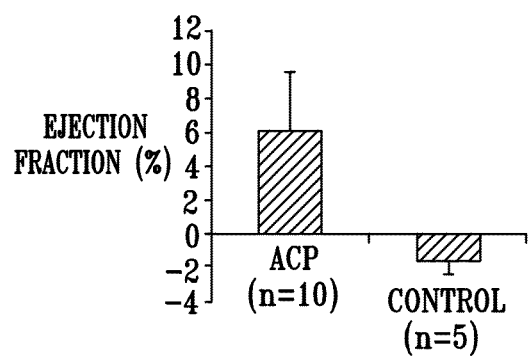
FIG. 9A
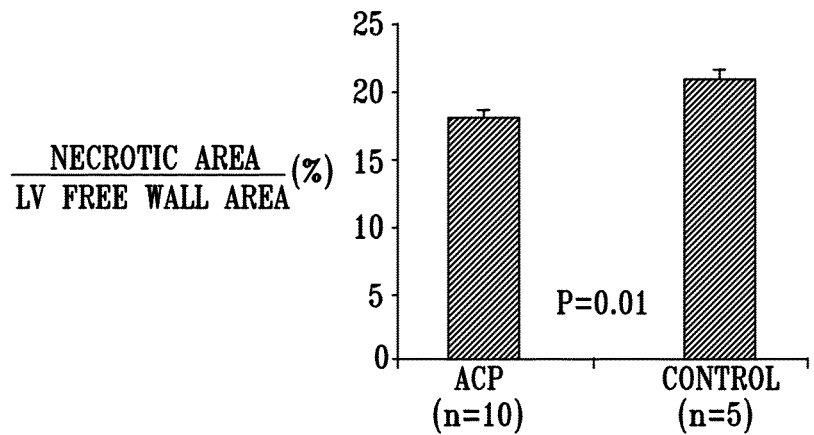
FIG. 9B

REGULATING STEM CELLS

CROSS-REFERENCE TO RELATED APPLICATIONS

This application is a continuation of co-pending U.S. patent application Ser. No. 12/224,913 filed on Feb. 22, 2010, which issued on Sep. 24, 2013 as U.S. Pat. No. 8,541,232, and which is a 35 U.S.C. §371 U.S. National Entry of PCT/IL2007/000308 filed on Mar. 8, 2007, which designated the United States, and which claims benefit under 35 U.S.C. §119(e) of U.S. Provisional Patent Application 60/780,781 filed on Mar. 8, 2006, the contents of each of which are incorporated herein by reference in their entireties.

FIELD OF THE INVENTION

The present invention generally relates to regulating stem cells. Specifically, the present invention relates to the induction of migration and differentiation of stem cells.

BACKGROUND OF THE INVENTION

Since the discovery of stem cells, it has been understood that they have significant potential to effectively treat many diseases [1]. Pluripotent stem cells derived from embryos and fetal tissue have the potential to produce more than 200 different known cell types, and thus can potentially replace dying or damaged cells of any specific tissue [2, 3]. Stem cells differ from other types of cells in the body, and, regardless of their source, have three general properties: (a) they are capable of dividing and renewing themselves for long periods, (b) they are undifferentiated, and (c) they can give rise to specialized cell types.

Stem cells have been identified in most organs and tissues, and can be found in adult animals and humans. Committed adult stem cells (also referred as somatic stem cells) were identified long ago in bone marrow. In the past decade, committed adult stem cells have also been identified in tissues that were previously not thought to contain them, such as brain tissue, skin tissue, and skeletal muscle tissue [8, 9, 10, 11, 12, 13]. It was initially believed that adult stem cells are tissue-committed cells that can only differentiate into cells of the same tissue and thus regenerate the damaged tissue [1, 4, 5, 6, 7]. However, recent work suggests that adult organ-specific stem cells are capable of differentiating into cells of different tissues [8, 9, 10, 11, 14, 16]. Transplantation of cells derived from brain, muscle, skin and fat tissue has been shown to result in a detectable contribution in several lineages distinct from their tissue of origin [8, 9, 10, 11]. For example, recent reports support the view that cells derived from hematopoietic stem cells (HSCs) can differentiate into cells native to the adult brain [14], providing additional evidence for the plasticity of such stem cells.

The HSC is the best characterized stem cell. This cell, which originates in bone marrow, peripheral blood, cord blood, the fetal liver, and the yolk sac, generates blood cells and gives rise to multiple hematopoietic lineages. As early as 1998, researchers reported that pluripotent stem cells from bone marrow can, under certain conditions, develop into several cell types different from known hematopoietic cells [13, 17, 18, 19, 20, 21, 22, 23, 24, 25, 26, 27]. Such an ability to change lineage is referred to as cellular transdifferentiation or cell plasticity. Bone marrow-derived stem cells (BMSCs) have already been shown to have the ability to differentiate into adipocytes, chondrocytes, osteocytes, hepatocytes, endothelial cells, skeletal muscle cells, and neurons [28, 29, 30, 31, 32].

The process of stem cell differentiation is controlled by internal signals, which are activated by genes within the cell, and by external signals for cell differentiation that include chemicals secreted by other cells, physical contact with neighboring cells, and certain molecules in the microenvironment [33, 34]. For example, if embryonic stem cells are allowed to aggregate to form embryoid bodies, they begin to differentiate spontaneously. Embryonic cells of embryoid bodies can form muscle cells, nerve cells, and many other cell types [35, 36]. Although spontaneous differentiation is a good indication that a culture of embryonic stem cells is healthy, it is not an efficient way to produce cultures of specific cell types. In order to generate cultures of specific types of differentiated cells, e.g., myocytes, blood cells, or nerve cells, scientists must control the multiplication and the differentiation of stem cells by regulating the chemical composition of the culture medium, altering the surface of the culture dish, and/or by inserting specific genes.

Successful attempts have been made in vitro to induce differentiation of adult stem cells into other cells by co-culturing with other adult cells. For example, recent work has shown that co-culturing adult mouse BMSCs and embryonic heart tissue causes the BMSCs to both integrate into cardiac tissue and differentiate into cardiomyocytes (CMCs). Other work has shown that mesenchymal stem cells acquire characteristics of cells in the periodontal ligament when co-cultured with periodontal ligament tissue [37, 38].

Tissue injury may be one of the stimulants for the recruitment of stem cells to an injured site, by causing changes in the tissue environment, thereby drawing stem cells from peripheral blood, as well as triggering tissue replacement by locally resident stem cells. Some reports of elevated levels of chemokines and chemokine receptors such as CXCR4-SDF explain some of this in vivo stem cell recruitment [39]. Other reports suggest an important role of the chemokine CXCR8 (IL-8) as an anti-apoptotic agent which promotes tissue survival and induces recruitment of endogenous stem/progenitor cells [M, N, O]. An example of this mechanism can be seen in recent work showing that stem cells differentiate into liver cells when co-cultured with injured liver cells separated from the stem cells by a barrier [30].

CD31, the platelet endothelial cell adhesion molecule-1 (PECAM-1), is widely used as a marker during the development of endothelial cell progenitors, vasculogenesis and angiogenesis (A, B, C, D, E, F, HP. CD31 is constitutively expressed on the surface of adult and embryonic endothelial cells, is a major constituent of the endothelial cell intercellular junction (where up to $10^6$ PECAM-1 molecules are concentrated) and is weakly expressed on many peripheral leukocytes and platelets (E, G, H). With a few minor exceptions, CD31 is not present on fibroblasts, epithelium, muscle, or other nonvascular cells. Independently of CD31 expression, endothelial cells and their progenitors are typically characterized by binding of Ulex-lectin in combination with the ability to uptake Acetylated-Low Density Lipoprotein (Ac-LDL) (I).

Regenerative medicine is an emerging scientific field with implications for both basic and practical research. Stem and progenitor cells are applied in a form of cellular therapy for local tissue repair and regeneration [41, 42]. These treatments aim to treat disorders in practically all tissues and organs, such as the bladder, intestine, kidney, trachea, eye, heart valves, and bones [43, 44]. Intensive studies are being conducted worldwide in order to generate stem cell-based tissue engineering therapies. These studies include experiments for the regeneration of blood vessels [13], bone [35, 45], cartilage, cornea, dentin, heart muscle [46], liver, pancreas [47], nervous tissue, skeletal muscle, and skin [18, 34, 48, 49]. Stem cell-based therapies can use cells from various organs in order to generate different tissues. For example, epithelial surfaces (taken from various tissues such as the skin, cornea and mucosal membrane) may be used as a source for corneal and skeletal tissues [50, 51]. Additionally, in a more widespread application, blood marrow-derived stem cells are used for regeneration of several different tissues such as bone, cartilage, adipocytes, neurons, and cells of the hematopoietic system [33, 42].

Stem cells can be administrated systemically or locally using injections to the injured site. However, other potential administration routes and usage of different medical devices are being developed and tested. Different medical devices such as chemical, metal or biodegradable based devices have been described for the administration of stem cells into the heart and blood vessels (J, K).

US Patent Application Publication 2004/0228847 to Goldschmidt-Clermont et al., which is incorporated herein by reference, describes stem/progenitor cells and, in particular, therapeutic strategies based on the use of such cells to effect vascular rejuvenation and/or to serve as delivery vehicles.

PCT Patent Publication WO 2005/120090 to Fulga et al., which is assigned to the assignee of the present patent application and is incorporated herein by reference, describes a method for use with extracted blood, including (a) applying blood to a first gradient suitable for selecting first-pass cells having a density less than 1.077 g/ml; (b) applying the first-pass cells to a second gradient suitable for selecting second-pass cells having a density between 1.055 and 1.074 g/ml; (c) increasing the number of cells having a density between 1.055 and 1.074 g/ml, by culturing the second-pass cells for a period lasting between 3 and 30 days; and (d) identifying endothelial progenitor cells in the cultured cells. Other embodiments are also described.

United States Patent Application Publication 2004-0228897 to Zhang et al., which is incorporated herein by reference, describes a medical device for use to assist stem cell and/or stem cell derivatives in repopulating, repairing and/or replacing the heart tissue in a failing heart muscle, in order to restore the heart's ability to pump blood. The medical device is made of biocompatible materials. The specific design of the device is described as facilitating the stem cells coated in the device to repopulate heart muscles inside the heart. Stem cells are attached to the coated device, proliferated and/or differentiated on the device in a bioreactor before implantation. The device also contains bioactive components that diminish rejection by the host's immune system. The device may be directly implanted into the failing heart muscle area to assist stem cells to repair failing heart muscles via surgical and/or percutaneous catheter based procedures. In another embodiment, the device may be implanted to the surgical site where abnormal heart muscles are removed, to assist stem cells to repopulate heart muscles, to replace the failing heart muscles.

US Patent Application Publication 2005/0209556 to Tresco et al., which is incorporated herein by reference, describes a device and method for the delivery of cells, tissues, enzymes and/or pharmacological agents for the treatment or prevention of diseases, disorders or deficiencies. The device is placed intravascularly and includes a chamber that houses living cells delimited by a membrane on either side that physically separates the cells from the blood stream and the central lumen of the catheter. The device can be inserted over a guidewire and permits flushing and reloading of the central lumen with viability supporting factors that sustain the cells in the outer chamber for long indwelling times without removing it from the body. In addition, the central lumen can be used to deliver therapeutic substances or withdraw blood. The new intravascular catheter is described as being able to be used for the treatment or prevention of a variety of diseases and disorders, and may use the implantation of living cells, tissues, enzymes or pharmacological agents. The device is described as being used, for example, for non-therapeutic purposes that may involve sustained intravascular release of biological factors as, for example, in stimulating growth of farm animals to augment the production of meat. Placement of cells within the device for release of angiogenesis, cytokines, enzymes, and other factors is described. The use of stem cells within the device is also described.

U.S. Pat. No. 6,810,286 to Donovan et al., which is incorporated herein by reference, describes a stimulatory device for the controlled production of angiogenic growth factors. More specifically, a subthreshold pulse generator is used for the local production of vascular endothelial growth factor.

The following references, which are incorporated herein by reference, may be of interest:

1. Leblond C. P. (1964), "Classification of cell populations on the basis of their proliferative behaviour," Natl. Cancer Inst. Monogr. 14:119-150
2. Evans M. J. and Kaufman M. H. (1981), "Establishment in culture of pluripotential cells from mouse embryos," Nature 292:154-156
3. Donovan P. J. and Gearhart J. (2001), "The end of the beginning for pluripotent stem cells," Nature 414:92-97
4. Spradling A. et al. (2001), "Stem cells find their niche," Nature 414:98-104
5. Weissman I. L. et al. (2001), "Stem and progenitor cells: origins, phenotypes, lineage commitments, and transdifferentiations," Annu. Rev. Cell. Dev. Biol. 17:387-403
6. Weissman I. L. (2000), "Stem cells: units of development, units of regeneration, and units in evolution," Cell 100: 157-68
7. Cheng A, Wang S, Cai J, Rao M S, Mattson M P (2003), "Nitric oxide acts in a positive feedback loop with BDNF to regulate neural progenitor cell proliferation and differentiation in the mammalian brain," Dev Biol. 258(2):319-33
8. Cousin B, Andre M, Arnaud E, Penicaud L, Casteilla L (2003), "Reconstitution of lethally irradiated mice by cells isolated from adipose tissue," Biochem Biophys Res Commun. 301(4):1016-22
9. Anderson D. J., Gage, F. H., and Weissman, I. L. (2001), "Can stem cells cross lineage boundaries?" Nat. Med. 7:393-395
10. Robey P. G. (2000), "Stem cells near the century mark," J. Clin. Invest. 105:1489-1491
11. Eisenberg L M, Burns L, Eisenberg C A (2003), "Hematopoietic cells from bone marrow have the potential to differentiate into cardiomyocytes in vitro," Anat Rec. 274A (1):870-82
12. Karl J. L., Fernandes Ian A. McKenzie, Pleasantine Mill et al. (2004), "A dermal niche for multipotent adult skin-derived precursor cells," Nature Cell Biology Published online: 1 Nov. 2004, DOI: 10.1038/ncb1181
13. Jackson K A, Mi T, Goodell M A (1999), "Hematopoietic potential of stem cells isolated from murine skeletal muscle," Proc Natl Acad Sci USA 96(25):14482-6
14. Brazelton T R, Rossi F M, Keshet G I, Blau H M (2000), "From marrow to brain: expression of neuronal phenotypes in adult mice," Science 290(5497):1775-9

15. Bjornson C R, Rietze R L, Reynolds B A, Magli M C, Vescovi A L (1999), "Turning brain into blood: a hematopoietic fate adopted by adult neural stem cells in vivo," Science 283(5401):534-7
16. Slack, J. M. (2000), "Stem cells in epithelial tissues," Science 287:1431-1433
17. Ferrari G., Cusella-De Angelis G., Coletta M., Paolucci E., Stornaiuolo A., Cossu G., and Mavilio F. (1998), "Muscle regeneration by bone marrow-derived myogenic progenitors," Science 279:528-30
18. Lagasse E, Connors H, Al-Dhalimy M, Reitsma M, Dohse M, Osborne L, Wang X, Finegold M, Weissman I L, Grompe M (2000), "Purified hematopoietic stem cells can differentiate into hepatocytes in vivo," Nat Med. 6:1229-34
19. Hirschi, K. K., and Goodell, M. A. (2002), "Hematopoietic, vascular and cardiac fates of bone marrow-derived stem cells," Gene Ther. 9:648-652
20. Theise N. D. et al. (2000), "Liver from bone marrow in humans," Hepatology 32:11-16
21. Kleeberger W. et al. (2002), "High frequency of epithelial chimerism in liver transplants demonstrated by microdissection and STR-analysis," Hepatology 35:110-116
22. Weimann J. M. et al. (2003), "Contribution of transplanted bone marrow cells to Purkinje neurons in human adult brains," Proc. Natl. Acad. Sci. USA 100:2088-2093
23. Quaini F. et al. (2002), "Chimerism of the transplanted heart," N. Engl. Med 346:5-15
24. Blau H. M. et al. (2001), "The evolving concept of a stem cell: entity or function?" Cell 105:829-841
25. Goodell M. A. et al. (2001), "Stem cell plasticity in muscle and bone marrow," Ann. NY Acad. Sci. 938:208-218
26. Krause D. S. (2002), "Plasticity of marrow-derived stem cells," Gene Ther. 9:754-758
27. Wulf G. G. et al. (2001), "Somatic stem cell plasticity," Exp Hematol. 29:1361-1370
28. Pittenger M. F. et al. (1999), "Multilineage potential of adult human mesenchymal stem cells," Science 284:143-147
29. Liechty K. W. et al. (2000), "Human mesenchymal stem cells engraft and demonstrate site-specific differentiation after in utero transplantation in sheep," Nature Med. 6:1282-1286
30. Li A. et al. (2003), "IL-8 directly enhanced endothelial cell survival, proliferation, and matrix metalloproteinases production and regulated angiogenesis", Journal of immunol. 170:3369-3376.
31. Laterveer L. et al. (1995), "Interleukin-8 induces rapid mobilization of hematopoietic stem cells with radioprotective capacity and long-term myelolymphoid repopulating ability", Blood 85:2269-75.
32. Schömig K. et al. (2006), "Interleukin-8 is associated with circulating CD133+ progenitor cells in acute myocardial infarction", European Heart Journal 27: 1032-1037
33. Jang Y Y, Collector M I, Baylin S B, Diehl A M, Sharkis S J (2004), "Hematopoietic stem cells convert into liver cells within days without fusion," Nat Cell Biol. 6(6):532-9. Epub 2004 May 9
34. Bittner R. E., Schofer C., Weipoltshammer K., Ivanova S., Streubel B., Hauser E., Freilinger M., Hoger H., Elbe-Burger A., and Wachtler F. (1999), "Recruitment of bone-marrow-derived cells by skeletal and cardiac muscle in adult dystrophic mdx mice," Anat. Embryol. (Berl) 199: 391-396
35. Mezey E, Chandross K J, Harta G, Maki R A, McKercher S R (2000), "Turning blood into brain: cells bearing neuronal antigens generated in vivo from bone marrow," Science. 290(5497):1779-82
36. Douglas W. L., Dimmeler S. (2004), "Therapeutic angiogenesis and vasculogenesis for ischemic diseases. Part I: Angiogenic cytokines," Circulation 109:2487-2491
37. Douglas W. L., Dimmeler S. (2004), "Therapeutic angiogenesis and vasculogenesis for ischemic diseases. Part II: Cell-based therapy," Circulation 109:2692-2697
38. Rodda S J, Kavanagh S J, Rathjen J, Rathjen P D (2002), "Embryonic stem cell differentiation and the analysis of mammalian development," Int J Dev Biol. 46(4):449-58
39. Amit M., Carpenter M. K., Inokuma M. S., Chiu C. P., Harris C. P., Waknitz M. A., Itskovitz-Eldor J., and Thomson J. A. (2000), "Clonally derived human embryonic stem cell lines maintain pluripotency and proliferative potential for prolonged periods of culture," Dev Biol. 227(2):271-8
40. Aoki S, Toda S, Sakemi T, Sugihara H (2003), "Coculture of endothelial cells and mature adipocytes actively promotes immature preadipocyte development in vitro," Cell Struct Funct. 28(1):55-60
41. Wan H, An Y, Zhang Z, Zhang Y, Wang Z (2003), "Differentiation of rat embryonic neural stem cells promoted by co-cultured Schwann cells," Chin Med J (Engl). 116(3): 428-31
42. Kollet O, Shivtiel S, Chen Y Q. et al. (2003), "HGF, SDF-1, and MMP-9 are involved in stress-induced human CD34+ stem cell recruitment to the liver," J Clin Invest. 112(2):160-9
43. Badorff C, Brandes R P, Popp R, Rupp S, Urbich C, Aicher A, Fleming I, Busse R, Zeiher A M, Dimmeler S (2003), "Transdifferentiation of blood-derived human adult endothelial progenitor cells into functionally active cardiomyocytes," Circulation 107(7):1024-32
44. Bianco, P. and Robey P. G. (2001), "Stem cells in tissue engineering," Nature 414:118-121
45. Lagasse E. et al. (2001), "Toward regenerative medicine," Immunity 14:425-436
46. Stock U. A., Vacanti J. P. (2001), "Tissue engineering: current state and prospects," Ann. Rev. Med 52:443-451
47. Kim W. S. et al. (1994), "Bone defect repair with tissue-engineered cartilage," Plast. Recontr. Surg. 94:580-584
48. Petite H. et al. (2000), "Tissue-engineered bone regeneration," Nature Biotechnol. 18:959-963
49. Jackson K A, Majka S M, Wang H, Pocius J, Hartley C J, Majesky M W, Entman M L, Michael L H, Hirschi K K, Goodell M A (2001), "Regeneration of ischemic cardiac muscle and vascular endothelium by adult stem cells," J Clin Invest. 107(11):1395-402
50. Ramiya V. K. et al. (2000), "Reversal of insulin-dependent diabetes using islets generated in vitro from pancreatic stem cells," Nature Medicine 6:278-282
51. Rafii S., Lyden D. (2003), "Therapeutic stem and progenitor cell transplantation for organ vascularization and regeneration," Nature Medicine 9:702-712
52. Gussoni E., Soneoka Y., Strickland C., Buzney E., Khan M., Flint A., Kunkel L., and Mulligan R. (1999), "Dystrophin expression in the mdx mouse restored by stem cell transplantation," Nature 401:390-4
53. Zhao Y et al. (2003), "A human peripheral blood monocyte-derived subset acts as pluripotent stem cells," Proc. Natl. Acad. Sci. USA 100:2426-2431
54. Kohji N, Masayuki Y, Yasutaka H. et al. (2004), "Corneal reconstruction with tissue-engineered cell sheets composed of autologous oral mucosal epithelium," N Engl J Med 351:1187-96

55. Kayisli U. A., Luk J, Guzeloglu-Kayisli O. et al. (2005), "Regulation of angiogenic activity of human endometrial endothelial cells in culture by ovarian steroids," J Clin Endocrinol Metab 89:5794-5802
56. Dimmeler S. (2005), "Circulating endothelial precursors: Identification of functional subpopulations," Blood 106 (7):2231-2232
57. Urbich C. et al. (2004), "Endothelial progenitor cells: Characterization and role in vascular biology," Circulation Research 95:343-353
58. Asahara T, Murohara T, Sullivan A, et al. (1997), "Isolation of putative progenitor endothelial cells for angiogenesis," *Science* 275:964-967.
59. Kalka C, Masuda H, Takahashi T, et al. (2000), "Transplantation of ex vivo expanded endothelial progenitor cells for therapeutic neovascularization," *Proc Natl Acad Sci USA.* 97:3422-3427.
60. Assmus B, Schachinger V, Teupe C, et al. (2002), "Transplantation of Progenitor Cells and Regeneration Enhancement in Acute Myocardial Infarction (TOPCARE-AMI)," *Circulation.* 106:3009-3017.
61. Yoon C. H, Hur J., Park K W, et al. (2005), "Synergistic Neovascularization by Mixed Transplantation of Early Endothelial Progenitor Cells and Late Outgrowth Endothelial Cells," Circulation. 112:1618-1627.
62. DeLisser, H. M., Christofidou-Solomidou, R. M. Strieter, M. D. et al. (1997), "Involvement of endothelial PECAM-1/CD31 in angiogenesis," Am J. Pathol. 151: 671-677.
63. Kawamoto A., Tkebuchava T., Yamaguchi J. I., et al. (2003), "Intramyocardial Transplantation of Autologous Endothelial Progenitor Cells for Therapeutic Neovascularization of Myocardial Ischemia," Circulation. 107:461-468
64. Newman P. J. (1997), "The Biology of PECAM-1," J Clin Invest. 99:3-8.
65. Vecchi, A., C. Garlanda, M. G. Lampugnani, M. Resnati, et al. (1994), "Monoclonal antibodies specific for endothelial cells of mouse blood vessels. Their application in the identification of adult and embryonic endothelium," Eur J Cell Biol. 63: 247-254.
66. Kanayasu-Toyoda T., Yamaguchi T., Oshizawa T., et al. (2003), "CD31 (PECAM-1)-Bright Cells Derived From AC133-Positive Cells in Human Peripheral Blood as Endothelial-Precursor Cells," Journal of Cell. Physiol. 195:119-129.
67. Yamamoto K., Takahashi T., Asahara T., et al. (2003), "Proliferation, differentiation, and tube formation by endothelial progenitor cells in response to shear stress," J Appl Physiol. 95: 2081-2088.
68. Cohen S., and Leor J. (2004), "Rebuilding Broken Hearts," Scientific American, November: 45-51.
69. US Patent Application Publication 2004/0228897 to Zhang et al.
70. US Patent Application Publication 2005/0272152 to Xu et al.

SUMMARY OF THE INVENTION

In the context of the present patent application and in the claims, a "core cell population" (CCP) is a population of at least 5 million cells which have a density of less than 1.072 g/ml, and at least 1% of which are CD34+CD45−/Dim (i.e., at least 50,000 of the cells are both (a) CD34 positive and (b) CD45 negative or CD45 Dim).

A CCP is typically, but not necessarily, generated from a hematopoietic source.

For most applications, at least 40% of the CCP is CD31Bright (i.e., at least 2 million cells out of the 5 million cells are CD31Bright).

While not being limited to any method of detection, cells expressing increased amounts of CD31 relative to isotype control are termed "CD31Bright" cells, because these cells bear more CD31 molecules relative to other cells, and thus tend to fluoresce brightly when stained with fluorescently-labeled antibodies. In this context, in the specification and in the claims, "bright" means that the fluorescence intensity of the labeled cellular marker of interest is at least 50 times higher (if measured using flow cytometry) than the isotype control intensity.

In accordance with an embodiment of the present invention, a method for producing a progenitor/precursor cell population (PCP) is provided, comprising (a) processing cells extracted from a cell donor to yield a CCP, and (b) stimulating the CCP to differentiate into the progenitor/precursor cell population. In the context of the specification and in the claims, "progenitor/precursor" cells are partially differentiated cells that are able to divide and give rise to differentiated cells.

While for some applications described herein, the density of the cells in the CCP is typically less than 1.072 g/ml (as described), for some applications, the CCP has at least 5 million cells having a density of less than 1.062 g/ml.

In the context of the specification and in the claims, an "elemental cell population" (ECP) is a population of at least 5 million cells which have a density of less than 1.072 g/ml, at least 1.0% of which are CD34+CD45−/Dim, and at least 30% of which are CD31Bright. Typically, but not necessarily, at least 40% of the cells in the ECP are CD31Bright. Typically, but not necessarily, at least 30% of the cells in the ECP are CD14+. Typically, but not necessarily, at least 1.5% or at least 2% of the cells in the ECP are CD34+CD45−/Dim. For some applications, the ECP has at least 5 million cells having a density of less than 1.062 g/ml. It is typically but not necessarily the case that a CCP is also an ECP. It is noted that, although for simplicity, embodiments of the present invention are described herein with respect to procedures relating to a CCP, the scope of the present invention includes, in each instance, performing the same procedure in relation to an ECP.

An "initiating cell population" (ICP), in the context of the specification and in the claims, is a cell population that can differentiate into a PCP. CCPs and ECPs are both examples of an ICP. An ICP is typically but not necessarily created by a process that comprises separating lower density cells (that are included in the ICP) from higher density cells. Such a separation may be accomplished, for example, by use of one or more gradients.

For some applications, the CCP-derived progenitor cells are used as a therapeutic cell product (e.g., for cancer therapy, for tissue regeneration, for tissue engineering, and/or for tissue replacement), as a research tool (e.g., for research of signal transduction, or for screening of growth factors), and/or as a diagnostic tool. When the CCP-derived progenitor cells are used as a therapeutic cell product, they are typically administered to a patient, in whom the progenitor cells mature into the desired cells (e.g., endothelial cells, retinal cells, etc.).

In an embodiment, at least one result of at least one stage in a process described herein is used as a diagnostic indicator. For example, pathology of a patient may be indicated if an in vitro procedure performed on extracted blood of the patient does not produce a CCP, when the same procedure performed on cells extracted from a healthy volunteer would result in production of the CCP. Alternatively or additionally, a pathology of a patient may be indicated if an in vitro stimulation procedure performed on an autologous CCP does not produce a desired number of progenitor cells of a particular class, when the same procedure would produce the desired number of progenitor cells of a particular class from a CCP derived from cells of a healthy volunteer. Further alternatively or additionally, a pathology of a patient may be indicated if one or more in vitro protocols used to assess a PCP do not yield the same results as a PCP originated from a healthy volunteer. Still further alternatively or additionally, a pathology of a patient may be indicated if one or more protocols used to assess a PCP following implantation within a patient do not perform as expected (e.g., like a PCP implanted in a healthy animal or human volunteer, or in an animal model of a similar disease).

When hematopoietic stem cells are used as a source to create the CCP, the resultant CCP is typically but not necessarily characterized by at least 40% of the cells in the CCP being CD31Bright, and at least 2.2% or at least 2.5% of the cells being CD34+CD45−/Dim.

Typically, the process of stimulating the CCP takes between about 2 and about 15 days (e.g., between about 3 and about 15 days), or between about 15 and about 120 days (e.g., between about 15 and about 30 days). Alternatively, stimulating the CCP takes less than 2 days, or more than 120 days.

The mammalian cell donor may be human or non-human, as appropriate. For some applications, the mammalian cell donor ultimately receives an administration of a product derived from the CCP, while for other applications, the mammalian cell donor does not receive such a product. Stem cells that can be used to produce the CCP are typically but not necessarily derived from one or more of the following source tissues: embryonic tissue, umbilical cord blood or tissue, neonatal tissue, adult tissue, bone marrow, mobilized blood, peripheral blood, peripheral blood mononuclear cells, skin cells, and other stem-cell-containing tissue. It is noted that the stem cells may be obtained from fresh samples of these sources or from frozen and then thawed cells from these source tissues.

The CCP is typically prepared by generating or obtaining a single cell suspension from one of the abovementioned source tissues. For example, mobilized blood mononuclear cells may be extracted using a 1.077 g/ml density gradient, e.g., a Ficoll™ gradient, including copolymers of sucrose and epichlorohydrin. It is to be noted that such a gradient is not used for all applications, e.g., for applications in which a single cell suspension is generated from a non-hematopoietic source (e.g., mucosal or skin cells). The output of this gradient is then typically passed through a second gradient (e.g., a Percoll™ gradient, including polyvinylpyrrolidone-coated silica colloids), suitable for selecting cells having a density less than 1.072 g/ml or less than 1.062 g/ml. These selected cells then typically propagate, in vitro, until they become a CCP. As appropriate, other density gradients may be used, independently of or in combination with those cited above in order to enrich the designated cells of the CCP. For example, an OptiPrep™ gradient, including an aqueous solution of Iodixanol, and/or a Nycodenz™ gradient may also be used.

The CCP is typically stimulated to generate progenitor cells of one or more of the following cell classes:

Blood cells (e.g., red blood cells and/or white blood cells (such as T cells or B cells));

Neural lineage cells (e.g., CNS neurons, oligodendrocytes, astrocytes, peripheral nervous system (PNS) neurons, and retinal cells (including, but not limited to, photoreceptors, pigment epithelium cells or retinal ganglion cells).

Endothelial cells;
Pericytes;
Smooth muscle cells;
Cardiomyocytes;
Osteoblasts;
Pancreatic endocrine or exocrine cells (e.g., beta cells or alpha cells);
Hepatic tissue (e.g., hepatocytes); and
Kidney cells.

For some applications, the CCP is transfected with a gene prior to the stimulation of the CCP, whereupon the CCP differentiates into a population of desired progenitor cells containing the transfected gene. Typically, these progenitor cells are then administered to a patient. For some applications, the PCP is transfected with a gene. Typically, these PCP cells are then administered to a patient.

In order to stimulate the CCP to differentiate into a desired class of progenitor cells, or in association with stimulation of the CCP to differentiate into a desired class of progenitor cells, the CCP is typically directly or indirectly co-cultured with "target tissue." The "target tissue" typically but not necessarily includes tissue from an organ whose cells represent a desired final state of the progenitor cells. For example, the target tissue may include brain or similar tissue, or heart or similar tissue, if it is desired for the progenitor cells to differentiate into brain tissue or into heart tissue, respectively. Other examples include:

(a) co-culturing the CCP with peripheral nerves (and/or culturing the CCP in conditioned medium derived therefrom), to induce differentiation of the CCP into peripheral neurons;

(b) co-culturing the CCP with central nervous system (CNS) nerves (and/or culturing the CCP in conditioned medium derived therefrom), to induce differentiation of the CCP into CNS neurons;

(c) co-culturing the CCP with retinal tissue (and/or culturing the CCP in conditioned medium derived therefrom), to induce differentiation of the CCP into retinal tissue. The retinal tissue may include, for example, one or more of: pigment epithelium, or photoreceptors. As appropriate, the retinal tissue may comprise fetal retinal tissue, embryonic retinal tissue, or mature retinal tissue;

(d) co-culturing the CCP with blood vessel tissue (and/or culturing the CCP in conditioned medium derived therefrom), to induce differentiation of the CCP into angiogenic lineage tissue and/or cardiomyocytes (CMCs);

(e) co-culturing the CCP with cardiac tissue (and/or culturing the CCP in conditioned medium derived therefrom), to induce differentiation of the CCP into CMCs;

(f) co-culturing the CCP with pancreatic endocrine or exocrine tissue (and/or culturing the CCP in conditioned medium derived therefrom), to induce differentiation of the CCP into pancreatic endocrine or exocrine cells; and (g) co-culturing the CCP with smooth muscle tissue (and/or culturing the CCP in conditioned medium derived therefrom), to induce differentiation of the CCP into smooth muscle cells.

Techniques described herein with respect to use of a target tissue may be used with any "sample" tissue, regardless of whether it is desired for the CCP to differentiate into a PCP having cells like those in the sample tissue.

For some applications, slices or a homogenate of the target tissue are used for co-culturing, although other techniques for preparing the target tissue will be apparent to a person of ordinary skill in the art who has read the disclosure of the present patent application.

The target tissue may be in essentially direct contact with the CCP, or separated therefrom by a semi-permeable membrane. As appropriate, the target tissue may be autologous, syngeneic, allogeneic, or xenogeneic with respect to the source tissue from which the CCP was produced. Alternatively or additionally, the CCP is cultured in a conditioned medium made using target tissue (e.g., a target tissue described hereinabove), that is autologous, syngeneic, allogeneic, or xenogeneic with respect to the source tissue from which the CCP was produced. For some applications, the target tissue and the CCP are co-cultured in the conditioned medium. It is to be noted that the source of the target tissue may also be tissue from a cadaver, and/or may be lyophilized, fresh, or frozen.

Alternatively or additionally, for some applications, to produce a desired class of progenitor cells, cells from the CCP are cultured in the presence of stimulation caused by "stimulation factors," e.g., one or more antibodies, cytokines, growth factors, tissue-derived extra cellular matrix, and/or other molecules, such as: IL-8, anti-IL-8, anti-CD34, anti-Tie-2, anti-CD133, anti-CD117, LIF, EPO, IGF, b-FGF, M-CSF, GM-CSF, TGF alpha, TGF beta, VEGF, BHA, BDNF, NGF, NT3, NT4/5, GDNF, S-100, CNTF, EGF, NGF3, CFN, ADMIF, estrogen, cortisone, dexamethasone, or any other molecule from the steroid family, prolactin, an adrenocorticoid hormone, ACTH, glutamate, serotonin, acetylcholine, NO, retinoic acid (RA), heparin, insulin, forskolin, a statin, an anti-diabetic drug (e.g., a thiazolidinedione such as rosiglitazone), NO, MCDB-201, MCT-165, glatiramer acetate (L-glutamic acid, L-alanine, L-tyrosine, L-lysine), a glatiramer acetate-like molecule, IFN alpha, IFN beta, or any other immunoregulatory agent, sodium selenite, linoleic acid, ascorbic acid, transferrin, 5-azacytidine, PDGF, VEGF, cardiotrophin, and thrombin.

In the context of the specification and in the claims, a "glatiramer acetate-like molecule" means a copolymer comprising:

(a) the same four amino acids as in glatiramer acetate, but in different ratios, (e.g., within 5%, 10%, or 25% of their current values of L-glutamic acid:L-alanine:L-tyrosine:L-lysine=0.141:0.427:0.095:0.338);

(b) three of the four amino acids in glatiramer acetate, but the fourth amino acid is replaced by a different naturally-occurring or synthetic amino acid;

(c) four amino acids, in which at least one of the amino acids is an enantiomer of the corresponding amino acid in glatiramer acetate, and the remainder of the amino acids (if any) are the corresponding L-amino acids that are in glatiramer acetate; or (d) a combination one or more of (a), (b), and (c).

It is to be appreciated that the particular stimulation factors described herein are by way of illustration and not limitation, and the scope of the present invention includes the use of other stimulation factors. As appropriate, these may be utilized in a concentration of between about 100 pg/ml and about 100 μg/ml (or molar equivalents). Typically, particular stimulation factors are selected in accordance with the particular class of progenitor cells desired. For example, to induce neural progenitor cells, one or more of the following stimulation factors are used: BHA, BDNF, NGF, NT3, NT4/5, GDNF, MCT-165, glatiramer acetate, a glatiramer acetate-like molecule, IFN alpha, IFN beta or any other immunoregulatory agent, S-100, CNTF, EGF, NGF3, CFN, ADMIF, and acetylcholine. In another example, to induce CMC progenitors, one or more of the following stimulation factors are used: bFGF, cortisone, estrogen, progesterone, or any other molecule form the steroid family, NO, sodium selenite, linoleic acid, ascorbic acid, retinoic acid (RA) or any other derivative of vitamin D, transferrin, 5-azacytidine, MCT-165, glatiramer acetate, a glatiramer acetate-like molecule, IFN alpha, IFN beta, or any other immunoregulatory agent, TGF-beta, insulin, EGF, IGF, PDGF, VEGF, cardiotrophin, MCDB201, and thrombin.

For some applications, the stimulation factors are introduced to the CCP in a soluble form, and/or in an aggregated form, and/or attached to a surface of a culture dish. In an embodiment, the CCP is incubated on a surface comprising a growth-enhancing molecule other than collagen or fibronectin. The growth-enhancing molecule may comprise, for example, VEGF or another suitable antibody or factor described herein. As appropriate, the growth-enhancing molecule may be mixed with collagen or fibronectin or plasma, or may be coated on the surface in a layer separate from a layer on the surface that comprises collagen or fibronectin or plasma. Alternatively, the only growth-enhancing molecule(s) on the surface of the culture dish is collagen and/or fibronectin and/or plasma.

In the context of the present patent application and in the claims, a surface "comprising" or "including" a molecule means that the molecule is coated on the surface, attached to the surface, or otherwise integrated into the surface.

Following stimulation of the CCP, the resultant product is typically tested to verify that it has differentiated into a desired form. Characterization of the differentiated cells is performed according to the cells' phenotypical, genotypical and physiological features. In accordance with an embodiment of the present invention, the cells are characterized by assessing functional/physiological activity thereof, in combination with or in place of evaluating the presence or absence of certain cellular markers. Evaluating functional/physiological activity of the cells following the stimulation of the CCP helps increase the likelihood that the product obtained and designated for in vivo use will perform as expected.

For example, when angiogenic cell precursors (ACPs) (which also include endothelial progenitor cells (EPCs)) are the desired product, the product is typically positive for the generation and/or expression of one or more of: CD34, CD117, CD133, Tie-2, CD31, CD34+CD133+, KDR, CD34+KDR+, CD144, von Willebrand Factor, SH2 (CD105), SH3, fibronectin, collagen (types I, III and/or IV), ICAM (type 1 or 2), VCAM1, Vimentin, BMP-R IA, BMP-RII, CD44, integrin b1, aSM-actin, and MUC18, CXCR4. Additionally, the ACP product typically functionally demonstrates uptake of Acetylated-Low Density Lipoprotein (Ac-LDL) (i.e., the product is Ac-LDL+) and/or secretes one or more of the following molecules: Interleukin-8 (IL-8), VEGF, Angiogenin, Matrix metalloproteinase 2 (MMP-2), or Matrix metalloproteinase 9 (MMP-9). Alternatively or additionally, the ACP product generates tube-like structures on a semi-solid matrix, and/or migrates towards chemoattractants (such as SDF-1 or VEGF), and/or proliferates in response to cell activation, and/or generates typical cell colonies/clusters. For some applications, in order to further characterize the cells, CD31Bright cells that demonstrate uptake of Ac-LDL are examined.

Typically, greater than 1.5% of the core cell population that was stimulated demonstrates one or more of the abovementioned characteristics. Alternatively, if neural progenitor cells are the desired product, then the product is typically positive for the generation and/or the expression of one or more of: Nestin, NSE, Notch, numb, Musashi-1, presenilin, FGFR4, Fz9, SOX 2, CD133, CD15, GD2, rhodopsin, recoverin, calretinin, PAX6, RX, Chx10, O4, and GFAP. Further alternatively, if cardiomyocyte (CMC) progenitors are the desired product, then the product is typically positive for the generation and/or the expression of one or more of: CD31, CD117, sarcomeric alpha-actin, beta-actin, alpha-actinin, desmin, cardiac troponin T, connexin43, alpha/beta-MHC, sarcomeric alpha-tropomyosin, Troponin I, GATA-4, Nkx2.5/Csx, and MEF-2.

For some applications, the time duration between collecting cells from the cell donor and using the CCP-derived progenitor cells (e.g., for administration into a patient), is reduced in order to effect almost immediate use thereof. Alternatively, the cells are preserved at one or more points in the process. For example, the CCP may be frozen prior to the stimulation thereof that generates progenitor cells. Alternatively, the CCP is stimulated in order to generate desired progenitor cells, and these progenitor cells are frozen. In either of these cases, the frozen cells may be stored and/or transported, for subsequent thawing and use. "Transport," in the context of the specification and the claims, means transport to a remote site, e.g., a site greater than 10 km or 100 km away from a site where the CCP is first created.

It is noted that certain applications are suitable for large-scale commercialization, including freezing and transport, such as (a) generation of stores of CCPs, (b) generation of stores of PCPs, (such as hematopoietic stem cells able to mature into CMCs), and (c) stem cell banks where individuals may store a CCP or differentiated progenitor cells, for possible later use. Other applications (such as acute post-stroke autologous administration of neuronal stem cells) may not benefit, or may not benefit as greatly, from the time delays provided by freezing of cells, although the technique may be useful for some purposes.

For some applications, the CCP is cultured for a period lasting between about 1 and about 20 days (e.g., between about 1 and 5 days) in a culture medium comprising less than about 5% serum. Alternatively, the CCP is cultured for a period lasting between about 1 and about 20 days (e.g., between about 1 and about 5 days) in a culture medium comprising greater than about 10% serum. In an embodiment, one of these periods follows the other of these periods.

For some applications, the CCP is cultured, during a low-serum time period, in a culture medium comprising less than about 10% serum, and, during a high-serum time period, in a culture medium comprising greater than or equal to about 10% serum. In an embodiment, culturing the CCP during the low-serum time period comprises culturing the CCP for a duration of between about 1 and about 20 days (e.g., between about 1 and about 5 days). Alternatively or additionally, culturing the CCP during the high-serum time period comprises culturing the CCP for a duration of between about 1 and about 120 days (e.g., between about 1 and about 30 days). Typically, culturing the CCP during the low-serum time period is performed prior to culturing the CCP during the high-serum time period. Alternatively, culturing the CCP during the low-serum time period is performed following culturing the CCP during the high-serum time period.

For some applications, during a hypoxic time period lasting at least about 2 hours, the CCP is cultured under hypoxic conditions, and, during a non-hypoxic time period lasting at least about 1 day, the CCP is cultured under non-hypoxic conditions. Culturing the CCP under hypoxic conditions may be performed prior to or following culturing the CCP under non-hypoxic conditions. Typically, but not necessarily, the hypoxic and non-hypoxic time-periods are within a culturing time period lasting less than about 120 days (e.g., less than about 30 days), and culturing the CCP under hypoxic conditions comprises culturing the CCP under hypoxic conditions during the first about two days of the culturing time period. Alternatively or additionally, culturing the CCP under hypoxic conditions comprises culturing the CCP under hypoxic conditions during the last about two days of the culturing time period. Further alternatively or additionally, culturing the CCP under hypoxic conditions comprises culturing the CCP under hypoxic conditions for at least about 2 hours between a first two days and a last two days of the culturing time period.

For some applications, the CCP is cultured in a culture medium comprising at least one of the following: erythropoietin, a statin, and an antidiabetic agent (e.g., a thiazolidinedione such as rosiglitazone). Alternatively or additionally, the CCP is cultured in the presence of one or more proliferation-differentiation-enhancing agents, such as, anti-CD34, anti-Tie-2, anti-CD133, anti-CD117, LIF, EPO, IGF, b-FGF, M-CSF, GM-CSF, TGF alpha, TGF beta, VEGF, BHA, BDNF, NGF, NT3, NT4/5, GDNF, 5-100, CNTF, EGF, NGF3, CFN, ADMIF, estrogen, prolactin, an adrenocorticoid hormone, ACTH, glutamate, serotonin, acetylcholine, NO, retinoic acid (RA) or any other vitamin D derivative, heparin, insulin, forskolin, cortisone, cortisol, dexamethasone, progesterone, or any other molecule from the steroid family, a statin, or an anti-diabetic drug (e.g., a thiazolidinedione such as rosiglitazone), MCDB-201, MCT-165, glatiramer acetate, a glatiramer acetate-like molecule, IFN alpha, IFN beta or any other immunoregulatory agent, sodium selenite, linoleic acid, ascorbic acid, transferrin, 5-azacytidine, PDGF, VEGF, cardiotrophin, and thrombin.

In an embodiment, techniques described herein are practiced in combination with (a) techniques described in one or more of the references cited herein, (b) techniques described in U.S. Provisional Patent Application 60/576,266, filed Jun. 1, 2004, (c) techniques described in U.S. Provisional Patent Application 60/588,520, filed Jul. 15, 2004, (d) techniques described in U.S. Provisional Patent Application 60/668,739, filed Apr. 5, 2005, (e) techniques described in U.S. Provisional Patent Application 60/636,391, filed Dec. 14, 2004, (f) techniques described in PCT Patent Application PCT/IL2005/001345, filed Dec. 14, 2005, which published as WO 06/064501, and/or PCT Patent Application PCT/IL2005/001348, filed Dec. 14, 2005, which published as WO 06/064504. Each of these patent applications is assigned to the assignee of the present patent application and is incorporated herein by reference, and the scope of the present invention includes embodiments described therein.

In an embodiment, a method is provided comprising culturing the CCP in a first container during a first portion of a culturing period; removing all or at least some cells of the CCP from the first container at the end of the first portion of the period; and culturing, in a second container during a second portion of the period, the cells removed from the first container. For example, removing at least some of the CCP cells may comprise selecting for removal cells that adhere to a surface of the first container.

When the cells from a progenitor/precursor cell population (PCP) derived from a CCP are designated for implantation into a human, they should be generally free from any bacterial or viral contamination. Additionally, in the case of a PCP of angiogenic cell precursors (ACPs), one or more of the following phenotypical, genotypical and physiological conditions should typically be met:

(I) Cells should be morphologically characterized as (a) larger in size than 20 uM and/or (b) elongated, spindle-shaped or irregular-shaped and/or (c) granulated or dark nucleated and/or (d) with flagella-like structures or pseudopodia and/or (e) fibroblast-like or polygonal in shape.

(II) Final cell suspension should typically contain at least 1 million cells expressing one or more of the following markers: CD31Bright, CD34, CD117, CD133, Tie-2, CD34+ CD133+, KDR, CD34+KDR+, CD144, von Willebrand Factor, SH2 (CD105), SH3, fibronectin, collagen (types I, III and/or IV), ICAM (type 1 or 2), VCAM1, Vimentin, BMP-R IA, BMP-RII, CD44, integrin b1, aSM-actin, and MUC18, CXCR4

(III) Cells should be able to uptake Ac-LDL.

(IV) Cells expressing CD31Bright should also demonstrate the ability to uptake Ac-LDL (e.g., at least about 10% or about 25% of cells that are CD31Bright also are able to uptake Ac-LDL).

(V) Cells should generally secrete one or more of the following molecules: IL-8, Angiogenin, VEGF, MMP2, and MMP9.

(VI) Cells should generally form tube-like structures when cultured on a semi-solid matrix containing growth factors.

(VII) Cells should generally migrate chemotactically towards different chemoattractants, such as SDF-1 and VEGF.

(VIII) Cells should generally form typical colonies and/or clusters when cultured in medium supplemented with growth factors such as VEGF and GM-SCF.

It is noted that the cells in CCPs generated from various tissues typically can be characterized as having greater than 75% viability.

It is noted that CCPs generated from blood, bone marrow, and umbilical cord blood, typically have greater than 70% of their cells being CD45+.

In some embodiments of the present invention, a novel composition of matter is provided, comprising (a) a cell population, or (b) a mixture comprising a cell population and molecules produced by the cell population, wherein (a) or (b) are produced by a method described herein (for example, in one of the methods set forth in the following paragraphs preceding the Brief Description section of the present patent application, or in one of the methods described in the Detailed Description section of the present patent application).

There is therefore provided, in accordance with an embodiment of the invention, a composition of matter, including a population of cultured cells that includes a sub-population of cells that both stain as CD31Bright and demonstrate uptake of Ac-LDL+.

In an embodiment, the sub-population includes at least 10%, 25%, or 50% of the cells in the population.

In an embodiment, at least 1.5% of the cells of the population include at least one morphological feature selected from the group consisting of: a cell size larger than 20 um, an elongated cell, a spindle-shaped cell, an irregularly-shaped cell, a granulated cell, a cell including an enlarged dark nucleus, a multinuclear cell, a cell including flagella-like structures, a cell including pseudopodia, and a cell having a polygonal shape.

In an embodiment, at least 1.5% of the cells of the population include at least one feature selected from the group consisting of: CD34, CD117, CD133, Tie-2, CD34+CD133+, KDR, CD34+KDR+, CD144, von Willebrand Factor, SH2 (CD105), SH3, fibronectin, collagen type I, collagen type III, collagen type IV, ICAM type 1, ICAM type 2, VCAM1, vimentin, BMP-R IA, BMP-RII, CD44, integrin b1, aSM-actin, MUC18, and CXCR4.

In an embodiment, at least 1.5% of the cells of the population secrete at least one molecule selected from the group consisting of: IL-8, angiogenin, VEGF, MMP2, and MMP9.

In an embodiment, at least 1.5% of the cells of the population include at least one feature selected from the group consisting of: a tube-like structure, a tendency to form a colony, a tendency to form a cluster, and a tendency to migrate towards a chemoattractant.

There is further provided, in accordance with an embodiment of the invention, a method including in vitro stimulating an initiating cell population (ICP) of at least 5 million cells that have a density of less than 1.072 g/ml, at least 1% of which are CD34+CD45−/Dim, and at least 25% of which are CD31Bright, to differentiate into a progenitor/precursor cell population (PCP).

There is still further provided, in accordance with an embodiment of the invention, a method including in vitro stimulating an initiating cell population (ICP) of at least ten thousand cells that have a density of less than 1.072 g/ml and at least 25% of which are CD31Bright to differentiate into a progenitor/precursor cell population (PCP).

There is yet further provided, in accordance with an embodiment of the invention, a method including separating lower density cells from higher density cells, the lower density cells defining an initiating cell population (ICP) at least 40% of which are CD31Bright, and in vitro stimulating the ICP to differentiate into a progenitor/precursor cell population (PCP).

In an embodiment, stimulating the ICP includes culturing the ICP for a period lasting between 1 and 5 days in a culture medium including less than or equal to 10% serum.

In an embodiment, stimulating the ICP includes culturing the ICP for a period lasting between 1 and 5 days in a culture medium including less than or equal to 5% serum.

In an embodiment, stimulating the ICP includes culturing the ICP for a period lasting between 1 and 5 days in a culture medium including 5-10% serum.

In an embodiment, stimulating the ICP includes culturing the ICP for a period lasting between 1 and 5 days in a culture medium including less than or equal to 5% serum.

In an embodiment, stimulating the ICP includes culturing the ICP for a period lasting between 1 and 5 days in a culture medium including at least 10% serum.

In an embodiment, stimulating the ICP includes culturing the ICP in a culture medium including a factor selected from the group consisting of: anti-Tie-2, anti-CD133, and anti-CD117.

In an embodiment, stimulating the ICP includes culturing the ICP in a culture medium including a factor selected from the group consisting of: anti-Tie-2, anti-CD133, and anti-CD117, anti-IL-8, anti IL-8 receptor, IL-8-antagonist, VEGF, anti-VEGF, and anti-VEGF receptor.

In an embodiment, stimulating the ICP includes culturing the ICP in a culture medium including IL-8.

In an embodiment, stimulating the ICP includes culturing the ICP in the presence of a factor selected from the group consisting of: anti IL-8 receptor, IL-8-antagonist, VEGF, anti-VEGF, and anti-VEGF receptor.

In an embodiment, stimulating the ICP includes culturing the ICP in the presence of IL-8.

In an embodiment, characterizing the PCP includes characterizing the PCP in response to an identification in the PCP of CXCR8.

In an embodiment, characterizing the PCP includes identifying that at least 1.5% of cells of the PCP include CXCR8.

In an embodiment, characterizing the PCP includes culturing a portion of the PCP on a semi-solid extracellular matrix (ECM), and identifying in the cultured portion a feature selected from the group consisting of: a tube-like structure, a colony, a cluster, and a tendency to migrate towards a chemoattractant.

In an embodiment, characterizing the PCP includes culturing at least a portion of the PCP on a membrane, and identifying a tendency of the at least a portion of the PCP to migrate toward IL-8.

In an embodiment, the ICP includes at least 5 million cells, and stimulating the ICP includes stimulating the ICP that includes the at least 5 million cells.

In an embodiment, at least 1.5% of the cells of the ICP are CD34+CD45−/Dim, and stimulating the ICP includes stimulating the ICP of which at least 1.5% of the cells are CD34+CD45−/Dim.

In an embodiment, at least 2% of the cells of the ICP are CD34+CD45−/Dim, and stimulating the ICP includes stimulating the ICP of which at least 2% of the cells are CD34+CD45−/Dim.

In an embodiment, at least 30% of the cells of the ICP are CD31Bright, and stimulating the ICP includes stimulating the ICP of which at least 30% of the cells are CD31Bright.

In an embodiment, the ICP includes at least 5 million cells that have a density of less than 1.062 g/ml, at least 1% of which are CD34+CD45−/Dim, and stimulating the ICP includes stimulating the ICP that has the at least 5 million cells that have a density of less than 1.062 g/ml.

In an embodiment, at least 50% of cells in the ICP are CD31Bright, and stimulating the ICP includes stimulating the ICP of which at least 50% of cells therein are CD31Bright.

In an embodiment, the method includes preparing the PCP as a product for administration to a patient. Alternatively or additionally, the method includes preparing the PCP as a research tool.

In an embodiment, stimulating the ICP includes only stimulating the ICP if the ICP is derived from a mammalian donor.

In an embodiment, the method includes applying cells extracted from a mammalian donor to one or more gradients suitable for selecting cells having a density less than 1.072 g/ml, and deriving the ICP from the cells applied to the gradient.

In an embodiment, the ICP is characterized by at least 2.5% of the ICP being CD34+CD45−/Dim, and stimulating the ICP includes stimulating the ICP having the at least 2.5% of the ICP that are CD34+CD45−/Dim.

In an embodiment, the ICP is characterized by at least 40% of the ICP being CD31Bright, and stimulating the ICP includes stimulating the ICP having the at least 40% of the ICP that are CD31Bright.

In an embodiment, stimulating the ICP includes stimulating the ICP to differentiate into a pre-designated, desired class of progenitor cells.

In an embodiment, the method includes deriving the ICP from at least one source selected from the group consisting of: embryonic tissue, fetal tissue, umbilical cord blood, umbilical cord tissue, neonatal tissue, adult tissue, bone marrow, mobilized blood, peripheral blood, peripheral blood mononuclear cells, skin cells, and plant tissue.

In an embodiment, the method includes deriving the ICP from at least one source selected from the group consisting of: fresh tissue and frozen tissue.

In an embodiment, the method includes identifying an intended recipient of the PCP, and deriving the ICP from at least one source selected from the group consisting of: tissue autologous to tissue of the intended recipient, tissue syngeneic to tissue of the intended recipient, tissue allogeneic to tissue of the intended recipient, and tissue xenogeneic to tissue of the intended recipient.

In an embodiment, stimulating the ICP includes culturing the ICP for a period lasting between 1 and 5 days in a culture medium including less than 5% serum.

In an embodiment, stimulating the ICP includes culturing the ICP for a period lasting between 1 and 5 days in a culture medium including at least 10% serum.

In an embodiment, stimulating the ICP includes culturing the ICP in a culture medium including a factor selected from the group consisting of: erythropoietin, a statin, and an antidiabetic agent.

In an embodiment, stimulating the ICP includes culturing the ICP in a culture medium including a factor selected from the group consisting of: estrogen, prolactin, progestin, an adrenocorticoid hormone, ACTH, and cortisone.

In an embodiment, stimulating the ICP includes culturing the ICP in a culture medium including a factor selected from the group consisting of: anti-Tie-2, anti-CD133, and anti-CD117.

In an embodiment, stimulating the ICP includes culturing the ICP in the presence of a factor selected from the group consisting of: erythropoietin, a statin, an antidiabetic agent, a thiazolidinedione, rosiglitazone, a proliferation-differentiation-enhancing agent, anti-CD34, anti-Tie-2, anti-CD133, anti-CD117, LIF, EPO, IGF, b-FGF, M-CSF, GM-CSF, TGF alpha, TGF beta, VEGF, BHA, BDNF, GDNF, NGF, NT3, NT4/5, S-100, CNTF, EGF, NGF3, CFN, ADMIF, estrogen, prolactin, an adrenocorticoid hormone, ACTH, MCT-165, glatiramer acetate, a glatiramer acetate-like molecule, IFN alpha, IFN beta, glutamate, serotonin, acetylcholine, NO, retinoic acid (RA), heparin, insulin, cortisone, and forskolin.

In an embodiment, the method includes preparing the ICP, and facilitating a diagnosis responsive to a characteristic of the preparation of the ICP.

In an embodiment, the method includes freezing the ICP prior to stimulating the ICP.

In an embodiment, the method includes freezing the PCP.

In an embodiment, the method includes transporting the ICP to a site at least 10 km from a site where the ICP is first created, and stimulating the ICP at the remote site.

In an embodiment, the method includes transporting the PCP to a site at least 10 km from a site where the PCP is first created.

In an embodiment, the method includes identifying the PCP as being suitable for therapeutic implantation in response to an assessment that the PCP includes at least 1 million PCP cells.

In an embodiment, the method includes identifying the PCP as being suitable for therapeutic implantation in response to an assessment that at least 1.5% of cells of the PCP demonstrate a feature selected from the group consisting of: a desired morphology, a desired cellular marker, a desired cellular component, a desired enzyme, a desired receptor, a desired genotypic feature, and a desired physiological feature.

In an embodiment, the method includes identifying the PCP as being suitable for therapeutic implantation in response to an assessment that the PCP includes at least 1 million angiogenic cell precursors (ACPs).

In an embodiment, the method includes identifying the PCP as being suitable for therapeutic implantation in response to an assessment that the PCP includes at least 1 million cardiomyocyte progenitors.

In an embodiment, the method includes identifying the PCP as being suitable for therapeutic implantation in response to an assessment that the PCP includes at least 1 million neural cell progenitors.

In an embodiment, the method includes transfecting into the PCP a gene identified as suitable for gene therapy.

In an embodiment, the method includes transfecting a gene into the PCP, and subsequently assessing a level of expression of the gene.

In an embodiment, the method includes transfecting a gene into the ICP, and subsequently assessing a level of expression of the gene.

In an embodiment, stimulating the ICP includes culturing the ICP during a period of between 2 and 120 days.

In an embodiment, stimulating the ICP includes culturing the ICP during a period of between 3 and 60 days.

In an embodiment, stimulating the ICP includes culturing the ICP in a culture medium including less than 10% serum, for a duration of between 1 and 120 days.

In an embodiment, stimulating the ICP includes culturing the ICP in a culture medium including at least 10% serum, for a duration of between 1 and 120 days.

In an embodiment, the method includes characterizing the PCP as including angiogenic cell precursors (ACPs), in response to an evaluation of at least a feature selected from the group consisting of: a phenotypical feature of cells in the PCP, a genotypical feature of cells in the PCP, and a physiological feature of cells in the PCP.

In an embodiment, characterizing the PCP includes characterizing the PCP in response to an evaluation of at least two of the features.

In an embodiment, characterizing the PCP includes characterizing the PCP in response to an evaluation of each of the features.

In an embodiment:

the phenotypical feature includes a morphological feature selected from the group consisting of: a cell size larger than 20 μm, an elongated cell, a spindle-shaped cell, an irregularly-shaped cell, a granulated cell, a cell including an enlarged dark nucleus, a multinuclear cell, a cell including flagella-like structures, a cell including pseudopodia, and a cell having a polygonal shape; and characterizing the PCP includes characterizing the PCP in response to an evaluation of the selected morphological feature.

In an embodiment, characterizing the PCP includes identifying that at least 1.5% of cells of the PCP have the selected feature.

In an embodiment, characterizing the PCP includes characterizing the PCP in response to an identification in the PCP of a feature selected from the group consisting of: CD31, CD31Bright, CD34, CD117, CD133, Tie-2, CD34+CD133+, KDR, CD34+KDR+, CD144, von Willebrand Factor, SH2 (CD105), SH3, fibronectin, collagen type I, collagen type III, collagen type IV, ICAM type 1, ICAM type 2, VCAM1, vimentin, BMP-R IA, BMP-RII, CD44, integrin b1, aSM-actin, MUC18, and CXCR4.

In an embodiment, characterizing the PCP includes identifying that at least 1.5% of cells of the PCP have the selected feature.

In an embodiment, characterizing the PCP includes characterizing the PCP in response to an assessment of uptake by the PCP of Ac-LDL.

In an embodiment, characterizing the PCP includes identifying that at least 1.5% of cells of the PCP demonstrate uptake of Ac-LDL.

In an embodiment, the PCP includes CD31Bright PCP cells, and characterizing the PCP includes identifying that at least 10% of the CD31Bright PCP cells demonstrate uptake of Ac-LDL.

In an embodiment, characterizing the PCP includes assessing secretion by the PCP of a molecule selected from the group consisting of: IL-8, angiogenin, VEGF, MMP2, and MMP9.

In an embodiment, characterizing the PCP includes identifying that at least 1.5% of cells of the PCP secrete the selected molecule.

In an embodiment, characterizing the PCP includes culturing a portion of the PCP on a semi-solid extracellular matrix (ECM), and identifying in the cultured portion a feature selected from the group consisting of: a tube-like structure, a colony, a cluster, and a tendency to migrate towards a chemoattractant.

In an embodiment, characterizing the PCP includes identifying that at least 1.5% of cells in the cultured portion have a property selected from the group consisting of: formation of a tube-like structure, an ability to form a colony, a cluster, and a tendency to migrate towards a chemoattractant.

In an embodiment, the method includes identifying the PCP as being suitable for therapeutic implantation in response to an assessment that the PCP includes at least 1 million ACPs.

In an embodiment, the method includes characterizing the PCP as including a cardiomyocyte (CMC) PCP in response to an evaluation of a feature selected from the group consisting of: a phenotypic feature of cells in the PCP, a genotypic feature on the cells in the PCP, and a physiological feature of cells in the PCP.

In an embodiment, characterizing the PCP includes characterizing the PCP in response to an evaluation of at least two of the features.

In an embodiment, characterizing the PCP includes characterizing the PCP in response to an evaluation of each of the features.

In an embodiment, the phenotypic feature includes a morphological feature selected from the group consisting of: a cell size larger than 20 um, an elongated cell, an irregularly-shaped cell, a granulated cell, a cell including an enlarged dark nucleus, a multinuclear cell, a cell with dark cytoplasm, and cells arranged in parallel to each other; and characterizing the PCP includes characterizing the PCP in response to an evaluation of the selected morphological feature.

In an embodiment, characterizing the PCP includes characterizing the PCP in response to an identification in the PCP of a feature selected from the group consisting of: CD31, CD117, sarcomeric alpha-actin, beta-actin, alpha-actinin, desmin, cardiac troponin T, Connexin-43, alpha/beta-MHC, sarcomeric alpha-tropomyosin, Troponin I, GATA-4, Nkx2.5/Csx, MLC-2, and MEF-2.

In an embodiment, characterizing the PCP includes characterizing the PCP in response to an identification of the PCP as expressing a gene for a factor selected from the group consisting of: sarcomeric alpha-actin, beta-actin, alpha-actinin, desmin, cardiac troponin T, Connexin-43, alpha/beta-MHC, sarcomeric alpha-tropomyosin, Troponin I, GATA-4, Nkx2.5/Csx, MLC-2 and MEF-2.

In an embodiment, the method includes identifying the PCP as being suitable for therapeutic implantation in response to an assessment that the PCP includes at least 1 million CMC progenitors.

In an embodiment, characterizing the PCP includes identifying that at least 1.5% of cells of the PCP have a characteristic selected from the group consisting of: a CMC-progenitor morphological characteristic, expression of a CMC-associated cellular marker, expression of a CMC-progenitor gene product, and expression of a CMC-progenitor physiological feature.

In an embodiment, characterizing the PCP includes characterizing the PCP in response to an identification in the PCP of an action in response to activation of the PCP, the action selected from the group consisting of: increasing intracellular Ca2+ level, generating membranal electrophysiological action potentials, and mechanical cellular contraction in vitro.

In an embodiment, activating the PCP to produce the selected action, using a technique selected from the group consisting of: electrical activation of the PCP, and chemical activation of the PCP.

In an embodiment, the method includes:
assessing a phenotypic aspect of the PCP and a genotypic aspect of the PCP and a physiological aspect of the PCP; and
designating the PCP as being suitable for implantation in a patient in response to each of the assessments.

In an embodiment, assessing the phenotypic aspect of the PCP includes assessing an aspect of the PCP selected from the group consisting of: morphology of the PCP, a cellular marker of cells of the PCP, an enzyme of the PCP, a coenzyme of the PCP, and presence of a designated cellular receptor on cells of the PCP.

In an embodiment, assessing the genotypic aspect of the PCP includes assessing an aspect of the PCP selected from the group consisting of: production of a gene by cells of the PCP, expression of a gene by cells of the PCP, and generation of a gene product by cells of the PCP.

In an embodiment, assessing the physiological aspect of the PCP includes assessing an aspect of the PCP selected from the group consisting of: secretion of soluble molecules by cells of the PCP, generation of signals by cells of the PCP, response by cells of the PCP to signals, and an enzymatic reaction performed by cells of the PCP.

In an embodiment, the method includes facilitating a diagnosis responsive to stimulating the ICP to differentiate into the PCP.

In an embodiment, facilitating the diagnosis includes assessing an extent to which the stimulation of the ICP produces a particular characteristic of the PCP.

In an embodiment, the method includes transfecting a gene into the ICP prior to stimulating the ICP.

In an embodiment, transfecting the gene includes transfecting into the ICP a gene identified as suitable for gene therapy.

In an embodiment, the method includes preparing, as a product for administration to a patient, the PCP generated by differentiation of the ICP into which the gene has been transfected.

In an embodiment, stimulating the ICP includes incubating the ICP in a container having a surface including a growth-enhancing factor.

In an embodiment, the growth-enhancing factor is selected from the group consisting of: collagen, plasma, fibronectin, a growth factor, tissue-derived extra cellular matrix, and an antibody to a stem cell surface receptor.

In an embodiment, stimulating the ICP includes incubating the ICP in a container with a surface including a growth-enhancing molecule other than collagen or fibronectin.

In an embodiment, incubating the ICP includes incubating the ICP in a container having a surface that includes, in addition to the growth-enhancing molecule, at least one of: collagen and fibronectin.

In an embodiment, the method includes mixing the growth-enhancing molecule with the at least one of: collagen and fibronectin.

In an embodiment, the method includes applying to the surface a layer that includes the growth-enhancing molecule and a separate layer that includes the at least one of: collagen and fibronectin.

In an embodiment, stimulating the ICP includes:
during a low-serum time period, culturing the ICP in a culture medium including less than 10% serum; and
during a high-serum time period, culturing the ICP in a culture medium including greater than or equal to 10% serum.

In an embodiment, culturing the ICP during the low-serum time period includes culturing the ICP for a duration of between 1 and 60 days.

In an embodiment, culturing the ICP during the low-serum time period includes culturing the ICP for a duration of between 1 and 5 days.

In an embodiment, culturing the ICP during the high-serum time period includes culturing the ICP for a duration of between 1 and 120 days.

In an embodiment, culturing the ICP during the high-serum time period includes culturing the ICP for a duration of between 1 and 60 days.

In an embodiment, culturing the ICP during the low-serum time period is performed prior to culturing the ICP during the high-serum time period.

In an embodiment, culturing the ICP during the low-serum time period is performed following culturing the ICP during the high-serum time period.

In an embodiment, the method includes:
during a hypoxic time period lasting at least 2 hours, culturing the ICP under hypoxic conditions; and
during a non-hypoxic time period lasting at least 1 day, culturing the ICP under non-hypoxic conditions.

In an embodiment, the hypoxic and non-hypoxic time-periods are within a culturing time period lasting less than 30 days, and culturing the ICP under hypoxic conditions includes culturing the cells under hypoxic conditions during a first two days of the culturing time period.

In an embodiment, the hypoxic and non-hypoxic time-periods are within a culturing time period lasting less than 30 days, and culturing the ICP under hypoxic conditions includes culturing the ICP under hypoxic conditions during a last two days of the culturing time period.

In an embodiment, the hypoxic and non-hypoxic time-periods are within a culturing time period lasting less than 30 days, and culturing the ICP under hypoxic conditions includes culturing the ICP under hypoxic conditions for at least 2 hours between a first two days and a last two days of the culturing time period.

In an embodiment, culturing the ICP under hypoxic conditions is performed prior to culturing the ICP under non-hypoxic conditions.

In an embodiment, culturing the ICP under hypoxic conditions is performed following culturing the ICP under non-hypoxic conditions.

In an embodiment, stimulating the ICP includes:
culturing the ICP in a first container during a first portion of a culturing period;
removing at least some cells of the ICP from the first container at the end of the first portion of the period; and
culturing, in a second container during a second portion of the period, the cells removed from the first container.

In an embodiment, the method includes subsequently to the step of culturing in the second container:

culturing the ICP in a primary container during a first portion of an additional culturing period;

removing at least some cells of the ICP from the primary container at the end of the first portion of the additional period; and culturing, in a secondary container during a second portion of the additional period, the cells removed from the primary container.

In an embodiment, stimulating the ICP includes:

culturing the ICP in a first container during a first portion of a culturing period;

removing cells of the ICP from the first container at the end of the first portion of the period; and culturing, in a second container during a second portion of the period, the cells removed from the first container.

In an embodiment, removing at least some cells of the ICP includes selecting for removal cells that adhere to a surface of the first container.

In an embodiment, removing at least some cells of the ICP includes selecting for removal cells that do not adhere to a surface of the first container.

In an embodiment, the first container includes on a surface thereof a growth-enhancing molecule, and culturing the ICP in the first container includes culturing the ICP in the first container that includes the growth-enhancing molecule.

In an embodiment, the growth-enhancing molecule is selected from the group consisting of: collagen, plasma, fibronectin, a growth factor, tissue-derived extra cellular matrix and an antibody to a stem cell surface receptor.

In an embodiment, the second container includes on a surface thereof a growth-enhancing molecule, and culturing the ICP in the second container includes culturing the ICP in the second container that includes the growth-enhancing molecule.

In an embodiment, the growth-enhancing molecule is selected from the group consisting of: collagen, fibronectin, a growth factor, and an antibody to a stem cell surface receptor.

In an embodiment, stimulating includes culturing the ICP with at least one factor derived from a sample tissue.

In an embodiment, the method includes preparing a conditioned medium for culturing the ICP therein, the conditioned medium including the factor, the factor being derived from the tissue, the tissue being selected from the group consisting of: peripheral nerve tissue, central nervous system (CNS) tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

In an embodiment, stimulating includes co-culturing the ICP with a sample tissue.

In an embodiment, co-culturing includes preparing the sample tissue by a method selected from the group consisting of: slicing the sample tissue, and homogenizing the sample issue.

In an embodiment, co-culturing includes:

utilizing the sample tissue to produce a conditioned medium; and co-culturing the ICP with the sample tissue in the conditioned medium.

In an embodiment, co-culturing includes separating the sample tissue from the ICP by a semi-permeable membrane.

In an embodiment, designating the sample tissue to include a tissue selected from the group consisting of: peripheral nerve tissue, central nervous system (CNS) tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

In an embodiment, the method includes systemically administering the PCP to a patient.

In an embodiment, the method includes locally administering the PCP to a site of the patient including injured tissue.

In an embodiment, locally administering the PCP includes implanting at the site a device including the PCP.

In an embodiment, the device includes at least one item selected from the group consisting of: a metal, a plastic, a glass, and a biodegradable element, and implanting the device includes implanting the device including the selected item.

In an embodiment, the method includes using the device to enable increased survival of PCP in injured tissue In an embodiment, the method includes configuring the device for slow release of cells of the PCP into the injured tissue.

In an embodiment, the method includes secreting, from the PCP, therapeutic molecules to the tissue.

In an embodiment, the method includes secreting, from the device, soluble molecules that support the PCP.

There is also provided, in accordance with an embodiment of the invention, apparatus for implantation in a patient, including a medical device including a PCP produced according to any of the procedures described herein for producing a PCP.

In an embodiment, the medical device includes a chamber having the PCP disposed therein, and a membrane, through which molecules generated by the PCP are able to pass.

There is further provided, in accordance with an embodiment of the invention, a method including in vitro stimulating an initiating cell population (ICP) of at least 5 million cells that have a density of less than 1.072 g/ml, and at least 1% of which are CD34+CD45−/Dim, to differentiate into a progenitor/precursor cell population (PCP).

There is also provided, in accordance with an embodiment of the invention, a method including in vitro stimulating an initiating cell population (ICP) of at least ten thousand cells that have a density of less than 1.072 g/ml to differentiate into a progenitor/precursor cell population (PCP).

There is further provided, in accordance with an embodiment of the invention, a method including separating lower density cells from higher density cells, the lower density cells defining an initiating cell population (ICP), and in vitro stimulating the ICP to differentiate into a progenitor/precursor cell population (PCP).

In an embodiment, the ICP includes at least 5 million cells, and wherein stimulating the ICP includes stimulating the ICP that includes the at least 5 million cells.

In an embodiment, at least 1.5% of the cells of the ICP are CD34+CD45−/Dim, and wherein stimulating the ICP includes stimulating the ICP of which at least 1.5% of the cells are CD34+CD45−/Dim.

In an embodiment, at least 2% of the cells of the ICP are CD34+CD45−/Dim, and wherein stimulating the ICP includes stimulating the ICP of which at least 2% of the cells are CD34+CD45−/Dim.

In an embodiment, at least 30% of the cells of the ICP are CD31Bright, and wherein stimulating the ICP includes stimulating the ICP of which at least 30% of the cells are CD34+CD45−/Dim.

In an embodiment, the ICP includes at least 5 million cells that have a density of less than 1.062 g/ml, at least 1% of which are CD34+CD45−/Dim, and wherein stimulating the ICP includes stimulating the ICP that has the at least 5 million cells that have a density of less than 1.062 g/ml.

In an embodiment, at least 50% of cells in the ICP are CD31Bright, and wherein stimulating the ICP includes stimulating the ICP of which at least 50% of cells therein are CD31Bright.

In an embodiment, the method includes preparing the PCP as a product for administration to a patient.

In an embodiment, the method includes preparing the PCP as a research tool.

In an embodiment, stimulating the ICP includes only stimulating the ICP if the ICP is derived from a mammalian donor.

In an embodiment, the method includes applying cells extracted from a mammalian donor to one or more gradients suitable for selecting cells having a density less than 1.072 g/ml, and deriving the ICP from the cells applied to the gradient.

In an embodiment, the ICP is characterized by at least 2.5% of the ICP being CD34+CD45−/Dim, and wherein stimulating the ICP includes stimulating the ICP having the at least 2.5% of the ICP that are CD34+CD45−/Dim.

In an embodiment, the ICP is characterized by at least 50% of the ICP being CD31Bright, and wherein stimulating the ICP includes stimulating the ICP having the at least 50% of the ICP that are CD31Bright.

In an embodiment, the ICP is characterized by at least 40% of the ICP being CD31Bright, and wherein stimulating the ICP includes stimulating the ICP having the at least 40% of the ICP that are CD31Bright.

In an embodiment, stimulating the ICP includes stimulating the ICP to differentiate into a pre-designated, desired class of progenitor cells.

In an embodiment, the method includes deriving the ICP from at least one source selected from the group consisting of: embryonic tissue, fetal tissue, umbilical cord blood, umbilical cord tissue, neonatal tissue, adult tissue, bone marrow, mobilized blood, peripheral blood, peripheral blood mononuclear cells, skin cells, and plant tissue.

In an embodiment, the method includes deriving the ICP from at least one source selected from the group consisting of: fresh tissue and frozen tissue.

In an embodiment, the method includes identifying an intended recipient of the PCP, and deriving the ICP from at least one source selected from the group consisting of: tissue autologous to tissue of the intended recipient, tissue syngeneic to tissue of the intended recipient, tissue allogeneic to tissue of the intended recipient, and tissue xenogeneic to tissue of the intended recipient.

In an embodiment, stimulating the ICP includes culturing the ICP for a period lasting between 1 and 5 days in a culture medium including less than 5% serum.

In an embodiment, stimulating the ICP includes culturing the ICP for a period lasting between 1 and 5 days in a culture medium including at least 10% serum.

In an embodiment, stimulating the ICP includes culturing the ICP in a culture medium including a factor selected from the group consisting of: erythropoietin, a statin, and an antidiabetic agent.

In an embodiment, stimulating the ICP includes culturing the ICP in a culture medium including a factor selected from the group consisting of: estrogen, prolactin, progestin, an adrenocorticoid hormone, ACTH, and cortisone.

In an embodiment, stimulating the ICP includes culturing the ICP in a culture medium including a factor selected from the group consisting of: anti-Tie-2, anti-CD133, and anti-CD117.

In an embodiment, stimulating the ICP includes culturing the ICP in the presence of a factor selected from the group consisting of: erythropoietin, a statin, an antidiabetic agent, a thiazolidinedione, rosiglitazone, a proliferation-differentiation-enhancing agent, anti-CD34, anti-Tie-2, anti-CD133, anti-CD117, LIF, EPO, IGF, b-FGF, M-CSF, GM-CSF, TGF alpha, TGF beta, VEGF, BHA, BDNF, GDNF, NGF, NT3, NT4/5, S-100, CNTF, EGF, NGF3, CFN, ADMIF, estrogen, prolactin, an adrenocorticoid hormone, ACTH, MCT-165, glatiramer acetate, a glatiramer acetate-like molecule, IFN alpha, IFN beta or any other immunoregulatory agent, glutamate, serotonin, acetylcholine, NO, retinoic acid (RA) or any other vitamin D derivative, heparin, insulin, and forskolin, cortisone.

In an embodiment, the method includes preparing the ICP, and facilitating a diagnosis responsive to a characteristic of the preparation of the ICP.

In an embodiment, the method includes freezing the ICP prior to stimulating the ICP.

In an embodiment, the method includes freezing the PCP.

In an embodiment, the method includes transporting the ICP to a site at least 10 km from a site where the ICP is first created, and stimulating the ICP at the remote site.

In an embodiment, the method includes transporting the PCP to a site at least 10 km from a site where the PCP is first created.

In an embodiment, the method includes identifying the PCP as being suitable for therapeutic implantation in response to an assessment that the PCP includes at least 1 million PCP cells.

In an embodiment, the method includes identifying the PCP as being suitable for therapeutic implantation in response to an assessment that at least 1.5% of cells of the PCP demonstrate a feature selected from the group consisting of: a desired morphology, a desired cellular marker, a desired cellular component, a desired enzyme, a desired receptor, a desired genotypic feature, and a desired physiological feature.

In an embodiment, the method includes identifying the PCP as being suitable for therapeutic implantation in response to an assessment that the PCP includes at least 1 million angiogenic cell precursors (ACPs).

In an embodiment, the method includes identifying the PCP as being suitable for therapeutic implantation in response to an assessment that the PCP includes at least 1 million cardiomyocyte progenitors.

In an embodiment, the method includes identifying the PCP as being suitable for therapeutic implantation in response to an assessment that the PCP includes at least 1 million neural cell progenitors.

In an embodiment, the method includes transfecting into the PCP a gene identified as suitable for gene therapy.

In an embodiment, the method includes transfecting a gene into the PCP, and subsequently assessing a level of expression of the gene.

In an embodiment, the method includes transfecting a gene into the ICP, and subsequently assessing a level of expression of the gene.

In an embodiment, stimulating the ICP includes culturing the ICP during a period of between 2 and 120 days.

In an embodiment, stimulating the ICP includes culturing the ICP during a period of between 3 and 60 days.

In an embodiment, stimulating the ICP includes culturing the ICP in a culture medium including less than 10% serum, for a duration of between 1 and 120 days.

In an embodiment, stimulating the ICP includes culturing the ICP in a culture medium including at least 10% serum, for a duration of between 1 and 120 days.

In an embodiment, the method includes characterizing the PCP as including angiogenic cell precursors (ACPs), in response to an evaluation of at least a feature selected from the group consisting of: a phenotypical feature of cells in the PCP, a genotypical feature of cells in the PCP, and a physiological feature of cells in the PCP.

In an embodiment, characterizing the PCP includes characterizing the PCP in response to an evaluation of at least two of the features.

In an embodiment, characterizing the PCP includes characterizing the PCP in response to an evaluation of each of the features.

In an embodiment:
the phenotypical feature includes a morphological feature selected from the group consisting of: a cell size larger than 20 m, an elongated cell, a spindle-shaped cell, an irregularly-shaped cell, a granulated cell, a cell including an enlarged dark nucleus, a multinuclear cell, a cell including flagella-like structures, a cell including pseudopodia, and a cell having a polygonal shape; and
characterizing the PCP includes characterizing the PCP in response to an evaluation of the selected morphological feature.

In an embodiment, characterizing the PCP includes identifying that at least 1.5% of cells of the PCP have the selected feature.

In an embodiment, characterizing the PCP includes characterizing the PCP in response to an identification in the PCP of a feature selected from the group consisting of: CD31Bright, CD34, CD117, CD133, Tie-2, CD34+CD133+, KDR, CD34+KDR+, CD144, von Willebrand Factor, SH2 (CD105), SH3, fibronectin, collagen type I, collagen type III, collagen type IV, ICAM type 1, ICAM type 2, VCAM1, vimentin, BMP-R IA, BMP-RII, CD44, integrin b1, aSM-actin, MUC18, and CXCR4.

In an embodiment, characterizing the PCP includes identifying that at least 1.5% of cells of the PCP have the selected feature.

In an embodiment, characterizing the PCP includes characterizing the PCP in response to an assessment of uptake by the PCP of Ac-LDL.

In an embodiment, characterizing the PCP includes identifying that at least 1.5% of cells of the PCP demonstrate uptake of Ac-LDL.

In an embodiment, characterizing the PCP includes identifying that at least 1.5% of cells that are CD31Bright demonstrate uptake of Ac-LDL.

In an embodiment, characterizing the PCP includes assessing secretion by the PCP of a molecule selected from the group consisting of: IL-8, angiogenin, VEGF, MMP2, and MMP9.

In an embodiment, characterizing the PCP includes identifying that at least 1.5% of cells of the PCP secrete the selected molecule.

In an embodiment, characterizing the PCP includes culturing a portion of the PCP on a semi-solid extracellular matrix (ECM), and identifying in the cultured portion a feature selected from the group consisting of: a tube-like structure, a colony, a cluster, and a tendency to migrate towards a chemoattractant.

In an embodiment, characterizing the PCP includes identifying that at least 1.5% of cells in the cultured portion have a property selected from the group consisting of: formation of a tube-like structure, an ability to form a colony, a cluster, and a tendency to migrate towards a chemoattractant.

In an embodiment, the method includes including identifying the PCP as being suitable for therapeutic implantation in response to an assessment that the PCP includes at least 1 million ACPs.

In an embodiment, the method includes characterizing the PCP as including a cardiomyocyte (CMC) PCP in response to an evaluation of a feature selected from the group consisting of: a phenotypic feature of cells in the PCP, a genotypic feature on the cells in the PCP, and a physiological feature of cells in the PCP.

In an embodiment, characterizing the PCP includes characterizing the PCP in response to an evaluation of at least two of the features.

In an embodiment, the method includes characterizing the PCP includes characterizing the PCP in response to an evaluation of each of the features.

In an embodiment, the phenotypic feature includes a morphological feature selected from the group consisting of: a cell size larger than 20 m, an elongated cell, an irregularly-shaped cell, a granulated cell, a cell including an enlarged dark nucleus, a multinuclear cell, a cell with dark cytoplasm, and cells arranged in parallel to each other; and
wherein characterizing the PCP includes characterizing the PCP in response to an evaluation of the selected morphological feature.

In an embodiment, characterizing the PCP includes characterizing the PCP in response to an identification in the PCP of a feature selected from the group consisting of: CD31, CD117, sarcomeric alpha-actin, beta-actin, alpha-actinin, desmin, cardiac troponin T, Connexin-43, alpha/beta-MHC, sarcomeric alpha-tropomyosin, Troponin I, GATA-4, Nkx2.5/Csx, MLC-2, and MEF-2.

In an embodiment, characterizing the PCP includes characterizing the PCP in response to an identification of the PCP as expressing a gene for a factor selected from the group consisting of: sarcomeric alpha-actin, beta-actin, alpha-actinin, desmin, cardiac troponin T, Connexin-43, alpha/beta-MHC, sarcomeric, alpha-tropomyosin, Troponin I, GATA-4, Nkx2.5/Csx, MLC-2 and MEF-2.

In an embodiment, the method includes identifying the PCP as being suitable for therapeutic implantation in response to an assessment that the PCP includes at least 1 million CMC progenitors.

In an embodiment, characterizing the PCP includes identifying that at least 1.5% of cells of the PCP have a characteristic selected from the group consisting of: a CMC-progenitor morphological characteristic, expression of a CMC-associated cellular marker, expression of a CMC-progenitor gene product, and expression of a CMC-progenitor physiological feature.

In an embodiment, characterizing the PCP includes characterizing the PCP in response to an identification in the PCP of an action in response to activation of the PCP, the action selected from the group consisting of: increasing intracellular $Ca^{2+}$ level, generating membranal electrophysiological action potentials, and mechanical cellular contraction in vitro.

In an embodiment, the method includes activating the PCP to produce the selected action, using a technique selected from the group consisting of: electrical activation of the PCP, and chemical activation of the PCP.

In an embodiment, the method includes:

assessing a phenotypic aspect of the PCP and a genotypic aspect of the PCP and a physiological aspect of the PCP; and designating the PCP as being suitable for implantation in a patient in response to each of the assessments.

In an embodiment, assessing the phenotypic aspect of the PCP includes assessing an aspect of the PCP selected from the group consisting of: morphology of the PCP, a cellular marker of cells of the PCP, an enzyme of the PCP, a coenzyme of the PCP, and presence of a designated cellular receptor on cells of the PCP.

In an embodiment, assessing the genotypic aspect of the PCP includes assessing an aspect of the PCP selected from the group consisting of: production of a gene by cells of the PCP, expression of a gene by cells of the PCP, and generation of a gene product by cells of the PCP.

In an embodiment, assessing the physiological aspect of the PCP includes assessing an aspect of the PCP selected from the group consisting of: secretion of soluble molecules by cells of the PCP, generation of signals by cells of the PCP, response by cells of the PCP to signals, and an enzymatic reaction performed by cells of the PCP.

In an embodiment, the method includes facilitating a diagnosis responsive to stimulating the ICP to differentiate into the PCP.

In an embodiment, facilitating the diagnosis includes assessing an extent to which the stimulation of the ICP produces a particular characteristic of the PCP.

In an embodiment, the method includes transfecting a gene into the ICP prior to stimulating the ICP.

In an embodiment, transfecting the gene includes transfecting into the ICP a gene identified as suitable for gene therapy.

In an embodiment, the method includes preparing, as a product for administration to a patient, the PCP generated by differentiation of the ICP into which the gene has been transfected.

In an embodiment, the method includes stimulating the ICP includes incubating the ICP in a container having a surface including a growth-enhancing factor.

In an embodiment, the method includes the growth-enhancing factor is selected from the group consisting of: collagen, plasma, fibronectin, a growth factor, tissue-derived extra cellular matrix, and an antibody to a stem cell surface receptor.

In an embodiment, stimulating the ICP includes incubating the ICP in a container with a surface including a growth-enhancing molecule other than collagen or fibronectin.

In an embodiment, incubating the ICP includes incubating the ICP in a container having a surface that includes, in addition to the growth-enhancing molecule, at least one of: collagen and fibronectin.

In an embodiment, the method includes mixing the growth-enhancing molecule with the at least one of: collagen and fibronectin.

In an embodiment, the method includes applying to the surface a layer that includes the growth-enhancing molecule and a separate layer that includes the at least one of: collagen and fibronectin.

In an embodiment, stimulating the ICP includes:

during a low-serum time period, culturing the ICP in a culture medium including less than 10% serum; and during a high-serum time period, culturing the ICP in a culture medium including greater than or equal to 10% serum.

In an embodiment, culturing the ICP during the low-serum time period includes culturing the ICP for a duration of between 1 and 60 days.

In an embodiment, culturing the ICP during the low-serum time period includes culturing the ICP for a duration of between 1 and 5 days.

In an embodiment, culturing the ICP during the high-serum time period includes culturing the ICP for a duration of between 1 and 120 days.

In an embodiment, culturing the ICP during the high-serum time period includes culturing the ICP for a duration of between 1 and 60 days.

In an embodiment, culturing the ICP during the low-serum time period is performed prior to culturing the ICP during the high-serum time period.

In an embodiment, culturing the ICP during the low-serum time period is performed following culturing the ICP during the high-serum time period.

In an embodiment, the method includes:

during a hypoxic time period lasting at least 2 hours, culturing the ICP under hypoxic conditions; and during a non-hypoxic time period lasting at least 1 day, culturing the ICP under non-hypoxic conditions.

In an embodiment, the hypoxic and non-hypoxic time-periods are within a culturing time period lasting less than 30 days, and wherein culturing the ICP under hypoxic conditions includes culturing the cells under hypoxic conditions during a first two days of the culturing time period.

In an embodiment, the hypoxic and non-hypoxic time-periods are within a culturing time period lasting less than 30 days, and wherein culturing the ICP under hypoxic conditions includes culturing the ICP under hypoxic conditions during a last two days of the culturing time period.

In an embodiment, the hypoxic and non-hypoxic time-periods are within a culturing time period lasting less than 30 days, and wherein culturing the ICP under hypoxic conditions includes culturing the ICP under hypoxic conditions for at least 2 hours between a first two days and a last two days of the culturing time period.

In an embodiment, culturing the ICP under hypoxic conditions is performed prior to culturing the ICP under non-hypoxic conditions.

In an embodiment, culturing the ICP under hypoxic conditions is performed following culturing the ICP under non-hypoxic conditions.

In an embodiment, stimulating the ICP includes:

culturing the ICP in a first container during a first portion of a culturing period;

removing at least some cells of the ICP from the first container at the end of the first portion of the period; and culturing, in a second container during a second portion of the period, the cells removed from the first container.

In an embodiment, the method includes, subsequently to the step of culturing in the second container:

culturing the ICP in a primary container during a first portion of an additional culturing period;

removing at least some cells of the ICP from the primary container at the end of the first portion of the additional period; and culturing, in a secondary container during a second portion of the additional period, the cells removed from the primary container.

In an embodiment, stimulating the ICP includes:

culturing the ICP in a first container during a first portion of a culturing period;

removing cells of the ICP from the first container at the end of the first portion of the period; and culturing, in a second container during a second portion of the period, the cells removed from the first container.

In an embodiment, removing at least some cells of the ICP includes selecting for removal cells that adhere to a surface of the first container.

In an embodiment, removing at least some cells of the ICP includes selecting for removal cells that do not adhere to a surface of the first container.

In an embodiment, the first container includes on a surface thereof a growth-enhancing molecule, and wherein culturing the ICP in the first container includes culturing the ICP in the first container that includes the growth-enhancing molecule.

In an embodiment, the growth-enhancing molecule is selected from the group consisting of: collagen, plasma, fibronectin, a growth factor, tissue-derived extra cellular matrix and an antibody to a stem cell surface receptor.

In an embodiment, the second container includes on a surface thereof a growth-enhancing molecule, and wherein culturing the ICP in the second container includes culturing the ICP in the second container that includes the growth-enhancing molecule.

In an embodiment, the growth-enhancing molecule is selected from the group consisting of: collagen, fibronectin, a growth factor, and an antibody to a stem cell surface receptor.

In an embodiment, stimulating includes culturing the ICP with at least one factor derived from a sample tissue.

In an embodiment, the method includes preparing a conditioned medium for culturing the ICP therein, the conditioned medium including the factor, the factor being derived from the tissue, the tissue being selected from the group consisting of: peripheral nerve tissue, central nervous system (CNS) tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

In an embodiment, stimulating includes co-culturing the ICP with a sample tissue.

In an embodiment, co-culturing includes preparing the sample tissue by a method selected from the group consisting of: slicing the sample tissue, and homogenizing the sample issue.

In an embodiment, co-culturing includes:

utilizing the sample tissue to produce a conditioned medium; and co-culturing the ICP with the sample tissue in the conditioned medium.

In an embodiment, co-culturing includes separating the sample tissue from the ICP by a semi-permeable membrane.

In an embodiment, the method includes designating the sample tissue to include a tissue selected from the group consisting of: peripheral nerve tissue, central nervous system (CNS) tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

There is further provided, in accordance with an embodiment of the invention, a method for treating a patient, including:

identifying a patient having a sexual dysfunction; and administering angiogenic cell precursors to the patient, in order to treat the dysfunction.

There is also provided, in accordance with an embodiment of the present invention, a method including in vitro stimulating a core cell population (CCP) of at least 5 million cells that have a density of less than 1.072 g/ml, and at least 1% or at least 2% of which are CD34+CD45−/Dim, to differentiate into a progenitor/precursor cell population (PCP).

For some applications, the CCP includes at least 5 million cells that have a density of less than 1.062 g/ml, at least 2% of which are CD34+CD45−/Dim, and stimulating the CCP includes stimulating the CCP that has the at least 5 million cells that have a density of less than 1.062 g/ml.

For some applications, the method includes preparing the PCP as a product for administration to a patient. Alternatively, the method includes preparing the PCP as a research tool or a diagnostic tool.

For some applications, stimulating the CCP includes only stimulating the CCP if the CCP is derived from a mammalian donor. For some applications, the method includes applying cells extracted from a mammalian donor to one or more gradients suitable for selecting cells having a density less than 1.072 g/ml, and deriving the CCP from the cells applied to the gradient.

For some applications, the CCP is characterized by at least 2.5% of the CCP being CD34+CD45−/Dim, and stimulating the CCP includes stimulating the CCP having the at least 2.5% of the CCP that are CD34+CD45−/Dim. For some applications, the CCP is characterized by at least 50% of the CCP being CD31Bright, and stimulating the CCP includes stimulating the CCP having the at least 50% of the CCP that are CDC31Bright+. For some applications, the CCP is characterized by at least 40% of the CCP being CD31Bright, and stimulating the CCP includes stimulating the CCP having the at least 40% of the CCP that are CD31Bright.

For some applications, stimulating the CCP includes stimulating the CCP to differentiate into a pre-designated, desired class of progenitor cells.

For some applications, stimulating the CCP includes culturing the CCP during a period of between 3 and 30, 60, or 120 days.

For some applications, the method includes deriving the CCP from at least one source selected from the group consisting of: embryonic tissue, fetal tissue, umbilical cord blood, umbilical cord tissue, neonatal tissue, adult tissue, bone marrow, mobilized blood, peripheral blood, peripheral blood mononuclear cells, skin cells, and plant tissue. Alternatively, the method includes deriving the CCP from at least one source selected from the group consisting of: fresh tissue and frozen tissue. For some applications, the method includes identifying an intended recipient of the PCP, and deriving the CCP from at least one source selected from the group consisting of: tissue autologous to tissue of the intended recipient, tissue syngeneic to tissue of the intended recipient, tissue allogeneic to tissue of the intended recipient, and tissue xenogeneic to tissue of the intended recipient.

For some applications, stimulating the CCP includes incubating the CCP in a container having a surface including an antibody.

For some applications, stimulating the CCP includes incubating the CCP in a container having a surface including a plasma.

For some applications, stimulating the CCP includes culturing the CCP for a period lasting between 1 and 5, 10, or 20 days in a culture medium including less than 5% serum. For some applications, stimulating the CCP includes culturing the CCP for a period lasting between 1 and 5, 10, or 20 days in a culture medium including at least 10% serum.

For some applications, stimulating the CCP includes culturing the CCP in the presence of at least one of the following: erythropoietin, a statin, an antidiabetic agent, a thiazolidinedione, rosiglitazone, a proliferation-differentiation-enhancing agent, anti-CD34, anti-Tie-2, anti-CD133, anti-CD117, LIF, EPO, IGF, b-FGF, M-CSF, GM-CSF, TGF alpha, TGF beta, VEGF, BHA, BDNF, NGF, NT3, NT4/5, GDNF, S-100, CNTF, EGF, NGF3, CFN, ADMIF, prolactin, an adrenocorticoid hormone, ACTH, glutamate, serotonin, acetylcholine, NO, retinoic acid (RA) or any other vitamin D derivative, heparin, insulin, forskolin, cortisone, cortisol, dexamethasone, estrogen, a steroid, MCDB-201, MCT-165, glatiramer acetate, a glatiramer acetate-like molecule, IFN alpha, IFN beta or any other immunoregulatory agent, sodium selenite, linoleic acid, ascorbic acid, transferrin, 5-azacytidine, PDGF, VEGF, cardiotrophin, and thrombin.

For some applications, the method includes preparing the CCP, and facilitating a diagnosis responsive to a characteristic of the preparation of the CCP.

For some applications, the method includes freezing the CCP prior to stimulating the CCP. For some applications, the method includes freezing the PCP.

For some applications, the method includes transporting the CCP to a site at least 10 km from a site where the CCP is first created, and stimulating the CCP at the remote site. For some applications, the method includes transporting the PCP to a site at least 10 km from a site where the PCP is first created.

In an embodiment, the method includes facilitating a diagnosis responsive to stimulating the CCP to differentiate into the PCP. For some applications, facilitating the diagnosis includes assessing an extent to which the stimulation of the CCP produces a particular characteristic of the PCP.

In an embodiment, the method includes transfecting a gene into the CCP prior to stimulating the CCP. For some applications, the method includes preparing, as a product for administration to a patient, the PCP generated by differentiation of the CCP into which the gene has been transfected.

In an embodiment, the method includes transfecting a gene into the PCP prior to administration of the PCP to a patient.

In an embodiment, stimulating the CCP includes incubating the CCP in a container with a surface including a growth-enhancing molecule other than collagen or fibronectin. For some applications, incubating the CCP cells includes incubating the CCP in a container having a surface that includes, in addition to the growth-enhancing molecule, at least one of: collagen, plasma and fibronectin. For some applications, the method includes mixing the growth-enhancing molecule with the at least one of: collagen, plasma and fibronectin. For some applications, the method includes applying to the surface a layer that includes the growth-enhancing molecule and a separate layer that includes the at least one of: collagen, plasma and fibronectin.

In an embodiment, stimulating the CCP includes:
during a low-serum time period, culturing the CCP in a culture medium including less than 10% serum; and
during a high-serum time period, culturing the CCP in a culture medium including greater than or equal to 10% serum.

For some applications, culturing the CCP during the low-serum time period includes culturing the CCP for a duration of between 1 and 5 or 20 days. For some applications, culturing the CCP during the high-serum time period includes culturing the CCP for a duration of between 1 and 30, 60, or 120 days. For some applications, culturing the CCP during the low-serum time period is performed prior to culturing the CCP during the high-serum time period. For some applications, culturing the CCP during the low-serum time period is performed following culturing the CCP during the high-serum time period.

In an embodiment, the method includes:
during a hypoxic time period lasting at least 2 hours, culturing the CCP under hypoxic conditions; and
during a non-hypoxic time period lasting at least 1 day, culturing the CCP under non-hypoxic conditions.

For some applications, the hypoxic and non-hypoxic time-periods are within a culturing time period lasting less than 120 days (e.g., less than 30 days), and culturing the CCP under hypoxic conditions includes culturing the cells under hypoxic conditions during a first two days of the culturing time period. For some applications, the hypoxic and non-hypoxic time-periods are within a culturing time period lasting less than 120 days (e.g., less than 30 days), and culturing the CCP under hypoxic conditions includes culturing the CCP under hypoxic conditions during a last two days of the culturing time period. For some applications, the hypoxic and non-hypoxic time-periods are within a culturing time period lasting less than 120 days (e.g., less than 30 days), and culturing the CCP under hypoxic conditions includes culturing the CCP under hypoxic conditions for at least 2 hours between a first two days and a last two days of the culturing time period.

For some applications, culturing the CCP under hypoxic conditions is performed prior to culturing the CCP under non-hypoxic conditions. Alternatively, culturing the CCP under hypoxic conditions is performed following culturing the CCP under non-hypoxic conditions.

In an embodiment, stimulating the CCP includes:
culturing the CCP in a first container during a first portion of a culturing period;
removing all or at least some cells of the CCP from the first container at the end of the first portion of the period; and
culturing, in a second container during a second portion of the period, the cells removed from the first container.

For some applications, removing at least some cells of the CCP includes selecting for removal cells that adhere to a surface of the first container. For some applications, removing at least some cells of the CCP includes selecting for removal cells that do not adhere to a surface of the first container.

For some applications, the first container includes on a surface thereof a growth-enhancing molecule, and culturing the CCP in the first container includes culturing the CCP in the first container that includes the growth-enhancing molecule.

For some applications, the growth-enhancing molecule is selected from the group consisting of: collagen, plasma, fibronectin, a growth factor, tissue-derived extra cellular matrix and an antibody to a stem cell surface receptor.

For some applications, the second container includes on a surface thereof a growth-enhancing molecule, and culturing the CCP in the second container includes culturing the CCP in the second container that includes the growth-enhancing molecule.

For some applications, the growth-enhancing molecule is selected from the group consisting of: collagen, plasma, fibronectin, a growth factor, tissue-derived extra cellular matrix and an antibody to a stem cell surface receptor.

In an embodiment, stimulating includes culturing the CCP with at least one factor derived from a target tissue. For some applications, the method includes preparing a conditioned medium for culturing the CCP therein, the conditioned medium including the factor, the factor being derived from a tissue selected from the group consisting of: peripheral nerve tissue, central nervous system (CNS) tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

In an embodiment, stimulating includes co-culturing the CCP with a tissue. For some applications, co-culturing includes preparing a target tissue by a method selected from the group consisting of: slicing the target tissue, and homogenizing the target issue. For some applications, co-culturing includes utilizing the target tissue to produce a conditioned medium, and co-culturing the CCP with the target tissue in the conditioned medium. For some applications, co-culturing includes separating the target tissue from the CCP by a semi-permeable membrane.

For some applications, the method includes designating a tissue for co-culture purposes to include a tissue selected from the group consisting of: peripheral nerve tissue, central nervous system (CNS) tissue, retinal tissue, pigment epithelial tissue, photoreceptor tissue, fetal retinal tissue, embryonic retinal tissue, mature retinal tissue, blood vessel tissue, cardiac tissue, pancreatic endocrine tissue, pancreatic exocrine tissue, smooth muscle tissue, lymphatic tissue, hepatic tissue, lung tissue, skin tissue, exocrine glandular tissue, mammary gland tissue, endocrine glandular tissue, thyroid gland tissue, pituitary gland tissue, and plant tissue.

There is also provided, in accordance with an embodiment of the present invention, a method including in vitro stimulating an elemental cell population (ECP) of at least 5 million cells that have a density of less than 1.072 g/ml, at least 1.5% of which are CD34+CD45−/Dim, and at least 30% of which are CD31Bright, to differentiate into a progenitor/precursor cell population (PCP).

For some applications, the present invention includes treating a patient with a PCP administrated systemically.

For some applications, the present invention includes treating a patient with a PCP administrated locally to injured tissue.

There is also provided, in accordance with an embodiment of the present invention, a method for treating a patient including administering a PCP using an implantable medical device, which, in an embodiment, includes metal, plastic, glass, or another material, and which for some applications is biodegradable. As appropriate for a given application, the medical device may include a stent, microparticles, or microcapsules.

There is also provided, in accordance with an embodiment of the present invention, a method comprising implanting, at a site including injured tissue, a medical device including a PCP, to enable increased survival at the site of the PCP.

There is also provided, in accordance with an embodiment of the present invention, a method including a medical device that provides slow release of a PCP into injured tissue.

There is also provided, in accordance with an embodiment of the present invention, a method including coupling a PCP to a medical device, wherein the PCP is adapted to be a source of therapeutic soluble molecules to a subject in whom the medical device is implanted. For some applications, apparatus comprises a chamber having disposed therein a population of stem cells (e.g., a PCP produced using techniques described herein), the chamber being surrounded by a semi-permeable membrane. Therapeutic molecules leave the chamber through the membrane, and treat the patient. As appropriate, techniques and apparatus described in the above-referenced US Patent Application Publication 2005/0209556 to Tresco and article by Rehman may be practiced in combination with this embodiment, mutatis mutandis.

There is also provided, in accordance with an embodiment of the present invention, a method including attaching a PCP to a medical device, wherein the medical device is a source of soluble molecules that support the PCP.

There is additionally provided, in accordance with an embodiment of the present invention, a composition of matter, including a population of cultured cells that includes a sub-population of cells that both stain as CD31Bright and demonstrate uptake of Ac-LDL+.

In an embodiment, the sub-population secretes IL-8.

In an embodiment, the sub-population secretes at least 50 pg IL-8 per 106 cells/ml over a period of at least 24 hours.

In an embodiment, the sub-population secretes at least 150 pg IL-8 per 106 cells/ml over a period of at least 24 hours.

In an embodiment, the sub-population secretes at least 1000 pg per 106 cells/ml over a period of at least 24 hours.

In an embodiment, at least 1.5% of the cells of the population secrete a molecule selected from the group consisting of: IL-8, angiogenin, VEGF, MMP2, and MMP9.

In an embodiment, at least 1.5% of the cells of the population have a tendency to migrate toward a chemoattractant selected from the group consisting of: bFGF, VEGF, SCF, G-CSF, GM-CSF, SDF-1, and IL-8.

There is further provided, in accordance with an embodiment of the present invention, a composition of matter, including a population of cultured cells that includes a sub-population of cells that stain as CD31Bright, demonstrate uptake of Ac-LDL+ and secrete interleukin-8.

In an embodiment, the sub-population includes at least 10% of the cells in the population.

In an embodiment, the sub-population includes at least 25% of the cells in the population.

In an embodiment, the sub-population includes at least 50% of the cells in the population.

In an embodiment, the sub-population secretes at least 50 pg IL-8 per 106 cells/ml over a period of at least 24 hours.

In an embodiment, the sub-population secretes at least 150 pg IL-8 per 106 cells/ml over a period of at least 24 hours.

In an embodiment, the sub-population secretes at least 1000 pg IL-8 per 106 cells/ml over a period of at least 24 hours.

In an embodiment, at least 1.5% of the cells of the population include a morphological feature selected from the group consisting of: a cell size larger than 20 um, an elongated cell, a spindle-shaped cell, an irregularly-shaped cell, a granulated cell, a cell including an enlarged dark nucleus, a multinuclear cell, a cell including flagella-like structures, a cell including pseudopodia, and a cell having a polygonal shape.

In an embodiment, at least 1.5% of the cells of the population include a feature selected from the group consisting of: CD34, CD117, CD133, Tie-2, CD34+CD133+, KDR, CD34+KDR+, CD144, von Willebrand Factor, SH2 (CD105), SH3, fibronectin, collagen type I, collagen type III, collagen type IV, ICAM type 1, ICAM type 2, VCAM1, vimentin, BMP-R IA, BMP-RII, CD44, integrin b1, aSM-actin, MUC18, CXCR4 and CXCR8.

In an embodiment, at least 1.5% of the cells of the population secrete a molecule selected from the group consisting of: angiogenin, VEGF, MMP2, and MMP9.

In an embodiment, at least 1.5% of the cells of the population include a feature selected from the group consisting of: a tube-like structure, a tendency to form a colony, a tendency to form a cluster, and a tendency to migrate towards chemoattractants selected from the group consisting of: bFGF, VEGF, SCF, G-CSF, GM-CSF, SDF-1, and IL-8.

In an embodiment, characterizing the PCP includes culturing at least a portion of the PCP on a surface, and identifying a tendency of the at least a portion of the PCP to migrate toward IL-8.

The present invention will be more fully understood from the following detailed description of embodiments thereof, taken together with the drawings, in which:

BRIEF DESCRIPTION OF THE DRAWINGS

FIG. 8 is a graph of migration of PBMC cells in response to hIL-8, in accordance with an embodiment of the present invention;

FIGS. 9A and 9B are graphs showing experimental results of improved ejection fraction and reduced necrosis in response to injection of ACP cells in accordance with an embodiment of the present invention;

DETAILED DESCRIPTION OF EMBODIMENTS

Example 1

A test was carried out in accordance with an embodiment of the present invention, and results are shown in Table 1 below. Peripheral blood was extracted from ten human volunteers for use in ten respective experiments. In each experiment, cells were fractioned from the blood using a Ficoll™ gradient in order to generate a population of peripheral blood mononuclear (PBMC) cells as source cells ("S. cells"). Subsequently, a CCP was generated in accordance with protocols described herein for Percoll™ based enrichment. Results in Table 1 show enrichment of the percentages of CD34+ CD45−/Dim cells in the CCP compared to the source cells. Enrichment is defined as the percentage of cells having a given characteristic in the CCP, divided by the percentage of cells having that characteristic in the source cells.

TABLE 1

| Exp No | % Viability | | % CD45 | | % CD34+ CD45−/Dim | | Enrichment factor |
|---|---|---|---|---|---|---|---|
| | S. cells | CCP | S. cells | CCP | S. cells | CCP | |
| 1 | 97.56 | 97.86 | 94.00 | 93.46 | 1.4 | 4.07 | 2.9 |
| 2 | 98.49 | 97.61 | 92.09 | 87.10 | 0.77 | 3.48 | 4.5 |
| 3 | 94.28 | 100 | 94.72 | 96.44 | 0.72 | 2.31 | 3.2 |
| 4 | 98.82 | 98.18 | 93.11 | 92.77 | 0.24 | 2.69 | 11.2 |
| 5 | 98.10 | 98.53 | 63.15 | 84.30 | 1.78 | 2.77 | 1.6 |
| 6 | 98.54 | 98.33 | 91.58 | 76.16 | 0.69 | 2.37 | 3.4 |
| 7 | 98.18 | 97.78 | 95.58 | 94.46 | 0.88 | 3.7 | 4.2 |
| 8 | 99.49 | 97.93 | 96.11 | 92.39 | 0.83 | 6.14 | 7.4 |
| 9 | 99.09 | 97.64 | 96.75 | 96.55 | 0.39 | 2.24 | 5.7 |
| 10 | 97.53 | 99.37 | 84.46 | 98.44 | 0.52 | 1.67 | 3.2 |
| AVG | 98.01 | 98.32 | 90.58 | 91.41 | 0.82 | 3.14 | 4.7 |

Example 2

Figure 1:
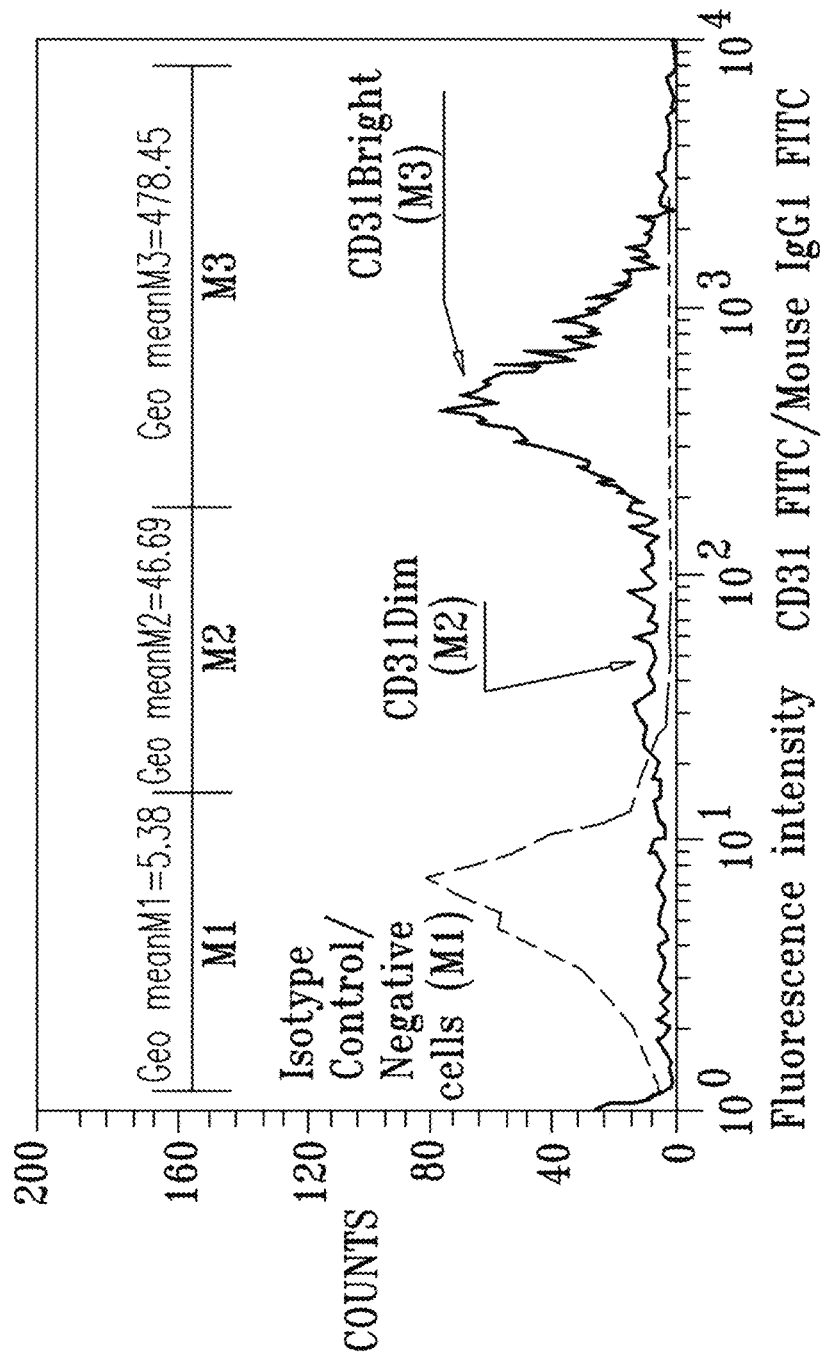
FIG. 1 is a graph showing results obtained from CCP cells in one representative experiment, in accordance with an embodiment of the present invention.

In a separate set of experiments, in accordance with an embodiment of the present invention, results were obtained as shown in FIG. 1 and Table 2 below. Peripheral blood was extracted from ten human volunteers for use in ten experiments. A CCP was generated in accordance with protocols described herein (see Example 1). Results in FIG. 1 and in Table 2 show the fluorescent intensity of CD31Bright cells in the CCP. CD31 brightness (Dim or Bright) is defined as the ratio between intensity resulting from staining using anti-CD31 FITC-conjugated monoclonal antibodies and intensity resulting from staining using isotype control FITC-conjugated antibodies.

FIG. 1 is a graph showing results obtained from CCP cells in one representative experiment, in accordance with an embodiment of the present invention. CCP cells stained using isotype control FITC-conjugated antibodies are represented by the dashed line and CCP cells stained using FITC-conjugated anti-CD31 antibodies are represented by the black line. Three different intensity areas were marked:

(a) M1—low intensity corresponding to non-specific staining of isotype control or cells that do not express CD31, located at geometric mean intensity of 5.38;

(b) M2—dim intensity corresponding to cells expressing CD31 at a geometric mean intensity of 46.69; and (c) M3—bright intensity corresponding to cells expressing CD31 at a geometric mean intensity of 478.45.

Table 2 is a numerical summary of intensities M1, M2 and M3 and their respective ratios resulting from ten independent experiments.

TABLE 2

| | CD31 Intensity Geo Mean | | | | | |
|---|---|---|---|---|---|---|
| EXP No. | Isotype Control M1 | dim M2 | bright M3 | Intensity Ratio | | |
| | | | | M2/M1 | M3/M1 | M3/M2 |
| 1 | 5.25 | 42.90 | 299.92 | 8 | 57 | 7 |
| 2 | 5.38 | 46.69 | 478.45 | 9 | 89 | 10 |
| 3 | 5.52 | 30.37 | 340.24 | 6 | 62 | 11 |
| 4 | 4.9 | 28.41 | 266.46 | 6 | 54 | 9 |
| 5 | 4.57 | 33.19 | 456.80 | 7 | 100 | 14 |
| 6 | 5.31 | 34.94 | 384.76 | 7 | 72 | 11 |
| 7 | 2.91 | 25.45 | 318.20 | 9 | 109 | 13 |
| 8 | 2.19 | 27.43 | 361.86 | 13 | 165 | 13 |
| 9 | 3.86 | 33.57 | 310.46 | 9 | 80 | 9 |
| 10 | 5.3 | 42.68 | 400.03 | 8 | 75 | 9 |
| AVG | 4.52 | 34.56 | 361.72 | 8.00 | 86.50 | 10.69 |
| SE | 0.37 | 2.30 | 21.74 | 0.63 | 10.42 | 0.66 |

CD31Bright cells' (M3) mean intensity is 86.5 (SE = 10.42) times greater than the negative control intensity (M1) and 10.69 (SE = 0.66) times more than CD31Dim cells (M2) (which themselves have an intensity 8.00 (SE = 0.63) times more than M1). Thus, results indicate that the CCP was enriched to provide CD31+ cells.

Example 3

In a separate set of experiments, in accordance with an embodiment of the present invention, results were obtained as shown in Table 3 below. Peripheral blood was extracted from nine human volunteers for use in nine experiments. A CCP was generated in accordance with protocols described hereinabove with reference to Example 1.

TABLE 3

| | % CD31Bright | | |
|---|---|---|---|
| Exp No. | S. Cells | CCP | Enrichment Factor |
| 1 | 10.1 | 60.4 | 6.0 |
| 2 | 25.4 | 80.85 | 3.2 |
| 3 | 19.1 | 76.85 | 4.0 |
| 4 | 25.1 | 77.3 | 3.1 |
| 5 | 16.1 | 75.8 | 4.7 |
| 6 | 12.7 | 75.0 | 5.9 |
| 7 | 17.5 | 53.3 | 3.1 |
| 8 | 21.9 | 80.96 | 3.7 |
| 9 | 18.6 | 64.58 | 3.5 |
| AVG | 18.5 | 71.67 | 4.13 |

Results in Table 3 indicate percentage enrichment of CD31Bright cells in the CCP as compared to the source cells.

Example 4

In a separate set of experiments, a human-PBMC-derived CCP was cultured in order to generate an ACP-rich PCP; the CCP was grown on fibronectin or plasma-coated T75 flasks in the presence of medium containing autologous serum (>=10%), 2 ng/ml VEGF, and 5 IU/ml Heparin.

Figure 2:
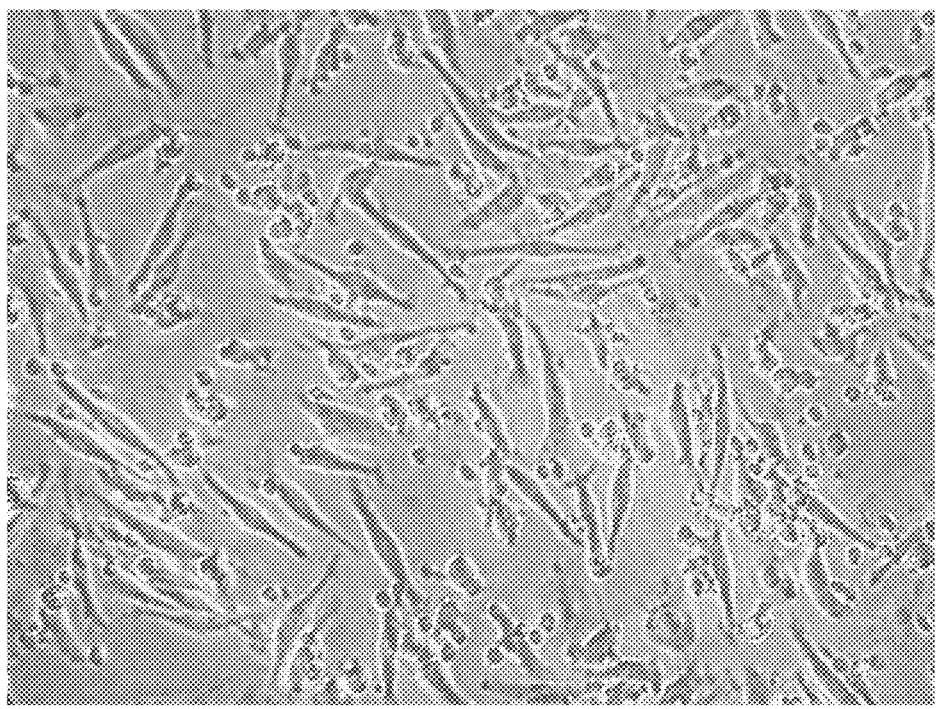
FIG. 2 is a photograph showing morphology of angiogenic cell precursor cells, produced in accordance with an embodiment of the present invention.

FIG. 2 is a photograph showing the morphology of a typical angiogenic cell precursor (ACP) population, produced in the experiments of Example 3, in accordance with an embodiment of the present invention. Typically, elongated and spindle-shaped cells are observed in cultures of ACPs. This image was obtained from ×200 magnification of cultured ACPs.

Example 5

In a separate set of experiments, a human-PBMC-derived CCP was cultured in order to generate an ACP-rich PCP, as described hereinabove with respect to Example 4. The CCP was grown on fibronectin or plasma-coated T75 flasks in the presence of medium containing autologous serum (>=10%), 2 ng/ml VEGF, and 5 IU/ml Heparin.

Figure 3:
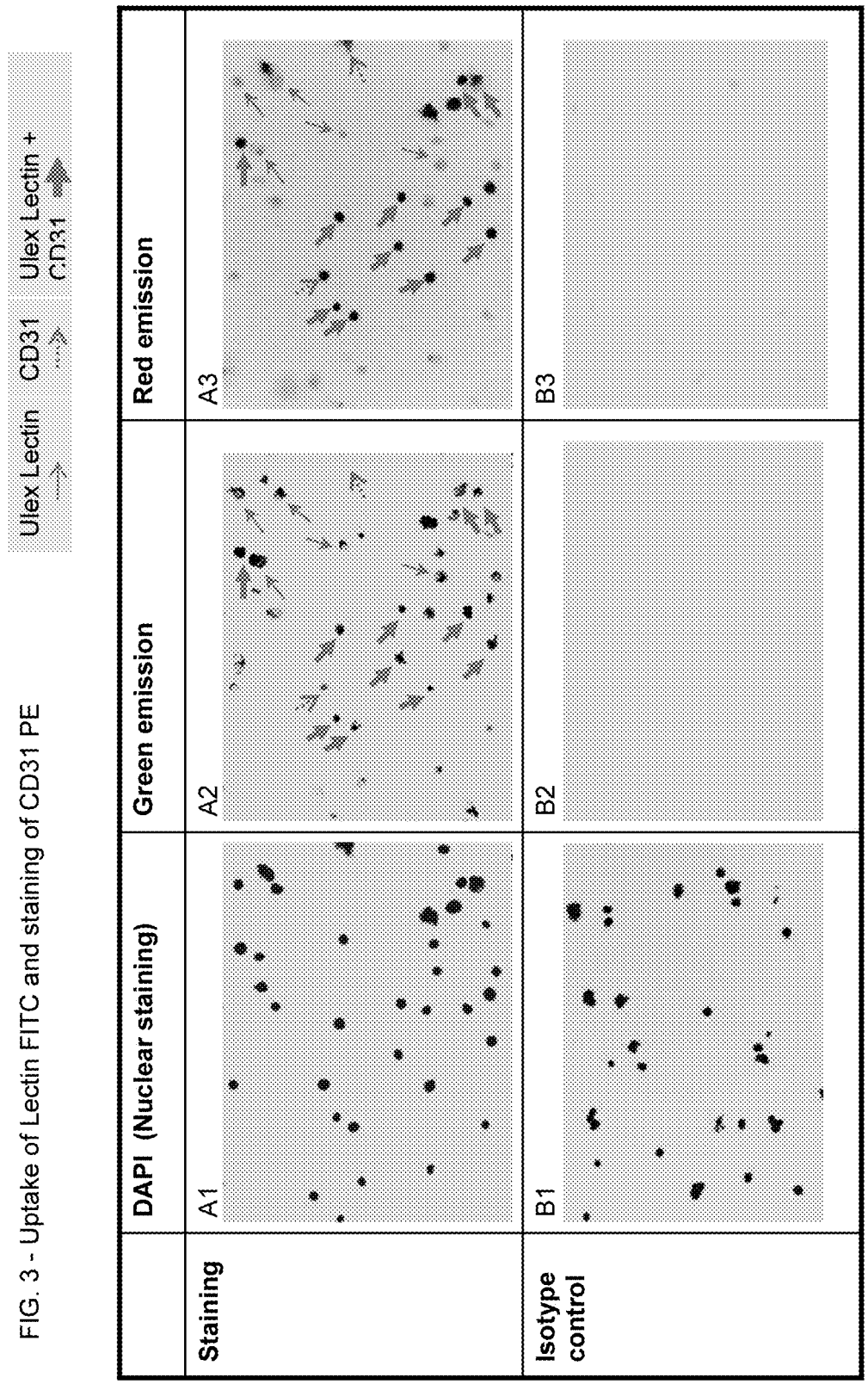
FIG. 3 is a photograph characterizing uptake of Ulex-Lectin and staining with CD31 stain of an ACP-rich PCP, produced in accordance with an embodiment of the present invention.

FIG. 3 contains photographs of a typical angiogenic cell precursor (ACP) population, produced in the experiments of Example 2, in accordance with an embodiment of the present invention. Harvested cells were loaded on a glass slide and fixed prior to their specific staining. Stained cells were mounted using a fluorescent mounting solution containing the nuclear stain DAPI. FIGS. A1-A3 are a series of photographs from cells stained with FITC-conjugated Ulex-Lectin, cells stained with PE-conjugated anti-CD31, or cells that stained with both Ulex-Lectin and anti-CD31, in accordance with respective embodiments of the present invention. A1 is a photograph of cells stained with the nuclear marker DAPI. A2 is a photograph showing green emission resulting from staining of the same cells with FITC-conjugated Ulex-lectin. A3 is a photograph showing red emission resulting from staining of the same cells with PE-conjugated anti-CD31 antibodies. FIGS. B1-B3 are a series of photographs from cells stained with isotype control antibodies, in accordance with respective embodiments of the present invention. B1 is a photograph of cells stained with the nuclear marker DAP1, B2 is a photograph showing green emission resulting from staining of the same cells with FITC-conjugated mouse IgG antibodies, and B3 is a photograph showing red emission resulting from staining of the same cells with PE-conjugated mouse IgG Antibodies.

Typically, ACP cells fluoresce both red and green indicating adhesion of both Ulex-Lectin and anti-CD31 thereto. Images were obtained from ×200 magnification.

Example 6

In a separate set of experiments, a human-PBMC-derived CCP was cultured in order to generate an ACP-rich PCP, as described hereinabove with reference to Example 4. The CCP was grown on fibronectin or plasma-coated T75 flasks in the presence of medium containing autologous serum (>=10%), 2 ng/ml VEGF, and 5 IU/ml Heparin.

Figure 4:
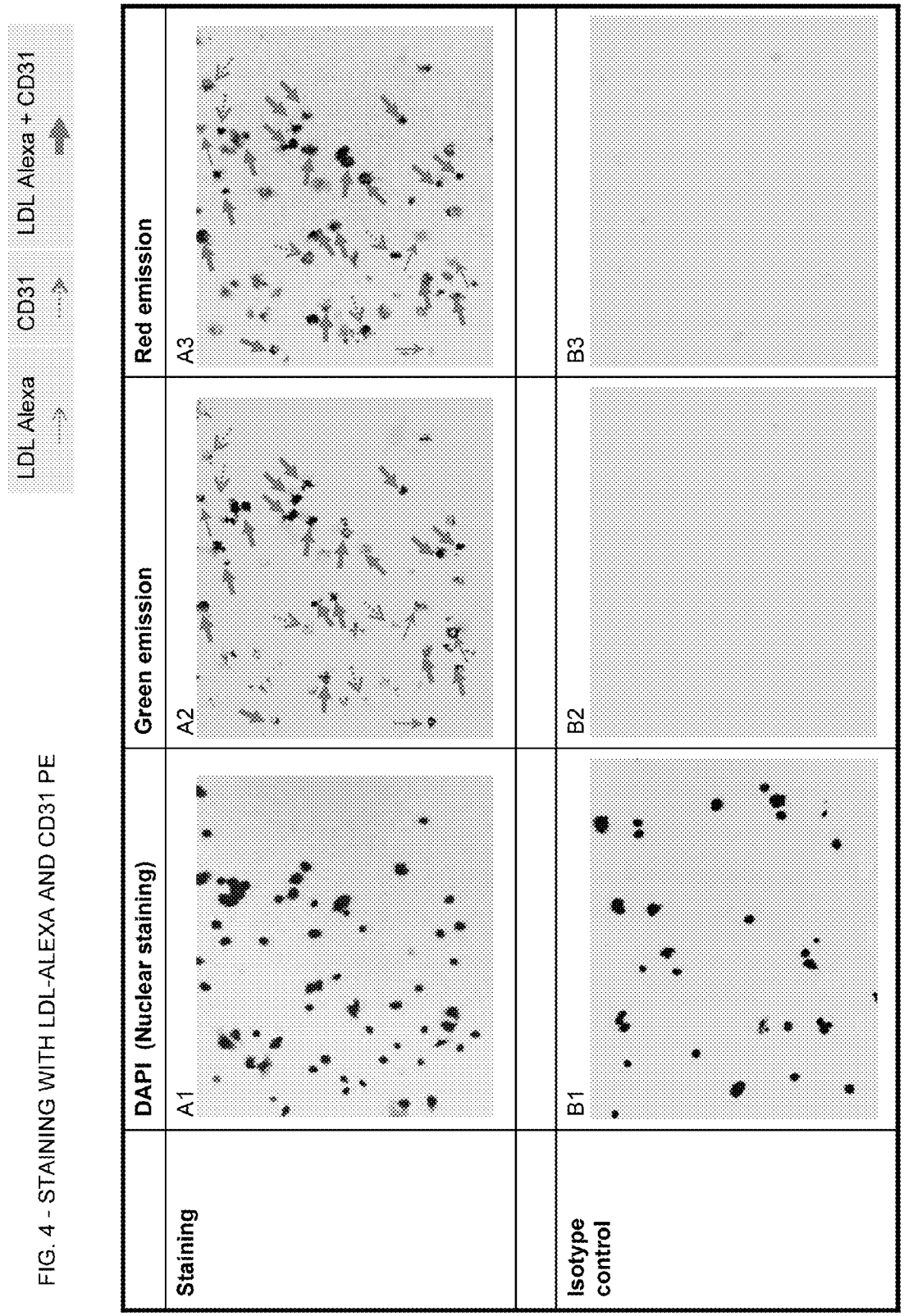
FIG. 4 is a photograph characterizing uptake of Ac-LDL and staining with CD31 stain of an ACP-rich PCP, produced in accordance with an embodiment of the present invention.

FIG. 4 contains photographs of a typical angiogenic cell precursor (ACP) population, produced in the experiments of Example 4, in accordance with an embodiment of the present invention. Harvested cells were loaded on a glass slide and fixed prior to their specific staining. Stained cells were mounted with a fluorescent mounting solution containing the nuclear stain DAPI. FIGS. A2-A3 are a series of photographs demonstrating uptake of Ac-LDL, cells stained with anti-CD31, or cells that show both uptake of Ac-LDL and staining with anti-CD31, in accordance with respective embodiments of the present invention. A1 is a photograph of cells stained with the nuclear marker DAPI, A2 is a photograph showing green emission resulting from uptake of FITC labeled-Ac-LDL by the same cells, and A3 is a photograph showing red emission resulting from staining of the same cells with PE-conjugated anti-CD31 antibodies. FIGS. B1-B3 are a series of photographs from cells stained with isotype control antibodies, in accordance with an embodiment of the present invention. B1 is a photograph of cells stained with the nuclear marker DAP1, B2 is a photograph showing green emission resulting from staining of the same cells with FITC-conjugated mouse IgG antibodies, and A3 is a photograph showing red emission resulting from staining of the same cells with PE-conjugated mouse IgG Antibodies.

Typically, ACP cells fluoresce both green and red indicating that ACPs uptake Ac-LDL as well as comprise CD31. Images were obtained from ×200 magnification.

Example 7

In the same set of experiments, the human-PBMC-derived CCP was cultured in order to generate an ACP-rich PCP as described hereinabove with respect to Example 4. Flow-cytometry percentage staining results from nine independent experiments are summarized in Table 4, and show the average staining results obtained on day 5 of culturing.

TABLE 4

|  | Number experiments (n) | Average on day 5 | Standard Error |
|---|---|---|---|
| % CD34 | 9 | 53.1 | 6.9 |
| % KDR | 9 | 2.3 | 1.1 |
| % Tie-2 | 9 | 6.6 | 1.6 |
| % Ac-LDL × CD31Bright | 9 | 60.7 | 4.7 |

Results using such a protocol typically yield a PCP having an average of 60.7% of cells that both demonstrate uptake of Ac-LDL and stain for CD31Bright.

Example 8

In a separate set of experiments, a human-PBMC-derived CCP was cultured in order to generate an ACP-rich PCP, as described hereinabove with respect to Example 4. Harvested ACP-rich PCP cells were washed from culture medium and incubated for 24 hours in a serum-free medium. Average secretion levels (pg/ml) of IL-8, VEGF, and angiogenin as obtained from four independent experiments are summarized in Table 5.

TABLE 5

| Group | IL-8 pg/ml | VEGF pg/ml | Angiogenin pg/ml |
|---|---|---|---|
| Control Medium | ≤20 | ≤20 | ≤20 |
| ACP derived medium | 10107 | 165 | 615 |

Example 9

In the same set of experiments, a human-PBMC-derived CCP was cultured in order to generate an ACP-rich PCP, as described hereinabove with reference to Example 4. Angiogenic pattern and vascular tube formation of ACP-rich PCP cells were examined microscopically following plating of the cells on an extracellular matrix gel (ECM). Typically, semi-closed and closed polygons of capillaries and complex mesh-like capillary structures were observed and scored according to a scale published by Kayisli et al. (52) as grade 4-5, indicating the angiogenic-inducing properties of the ACP-rich PCP.

Figure 5:
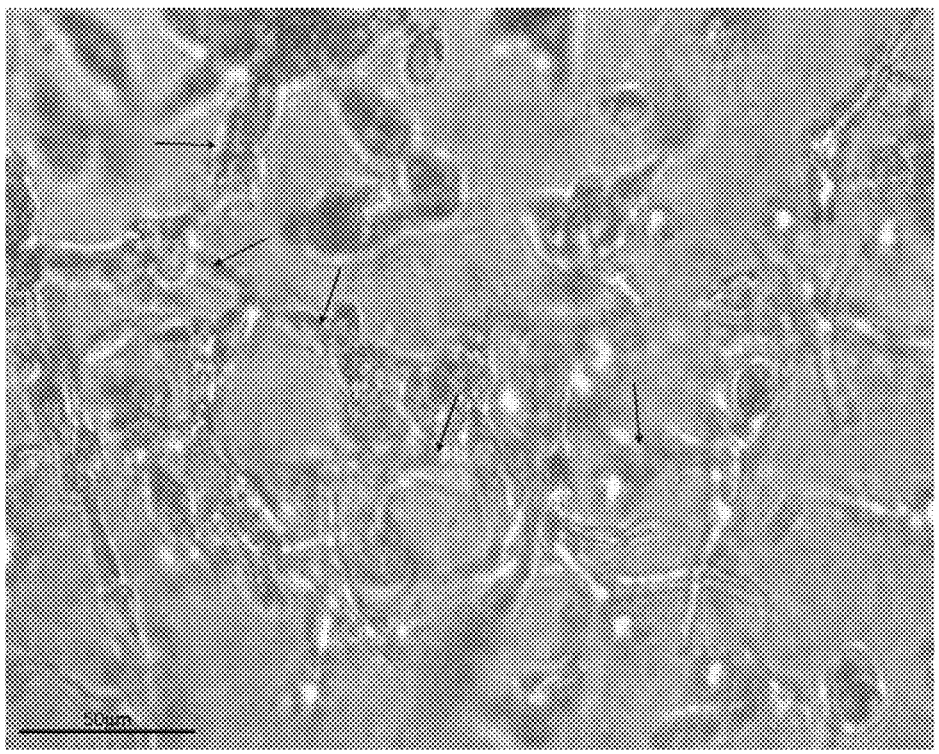
FIG. 5 is a photograph showing tube formation in an ACP-rich PCP, produced in accordance with an embodiment of the present invention.

FIG. 5 is a photograph showing tube formation in an ACPs, produced in the experiments of Example 6, in accordance with an embodiment of the present invention. Typical mesh-like capillary structures generated from a harvested ACPs are present in the culture and are suitable for administration to a human.

Example 10

In a separate set of experiments, a human-PBMC-derived CCP was cultured in order to generate an ACP-rich PCP; the CCP was grown on fibronectin or plasma-coated T75 flasks in the presence of medium containing autologous serum (>=10%), 2-10 ng/ml VEGF, and 5 IU/ml Heparin. At the end of the culturing period, ACP cells were harvested and labeled with 0.8 ug/ml Ac-LDL-DiO for 15 min at 37 C. and placed in inserts which were placed in wells. One million labeled ACPs were placed on microporous membrane inserts with a pore size of 8 micrometer. 200 ul medium was placed at the bottom of each of the wells. Negative control (M199), positive control (e.g., 20 ng/ml VEGF, 20 ng/ml bFGF, and 20 ng/ml SCF) and 0.08-60 ng/ml human recombinant Interleukin-8 (hIL-8) diluted in M199 medium were plated in respective wells and the ACP cells were allowed to migrate toward each respective medium. Following 1 hour incubation in the presence of the negative control medium, the positive control medium, and the IL-8 containing media, labeled migrating cells from 10-15 random microscopic fields were evaluated using fluorescent microscope and automated counting software (NIH ImageJ). Calculation of cell number per 1 mm^2 was based on area of counting field (×20) which equals 0.178 mm^2, and each mm^2 contains 5.62 fields. Assessment of ACP migratory potential indicated that ACPs migrate toward chemokines such as VEGF, bFGF, SCF, and hIL-8 in a manner dependent on respective concentrations thereof, e.g., hIL-8 concentration of typically higher than 6.7 ng/ml induces substantial migration of ACPs, and hIL-8 concentrations of about 7-20 ng/ml typically induce substantial migration of ACPs.

Figure 6A:
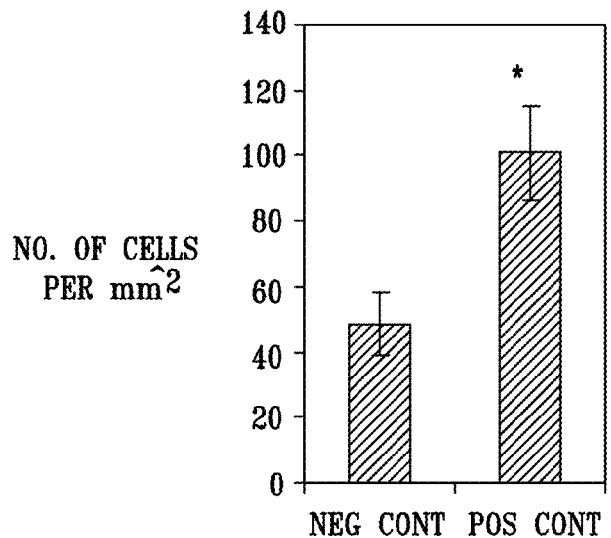
FIGS. 6A and 6B are graphs showing migration of Ac-LDL-DiO pre-labeled ACPs in response to hIL-8, in accordance with an embodiment of the present invention.
Figure 6B:
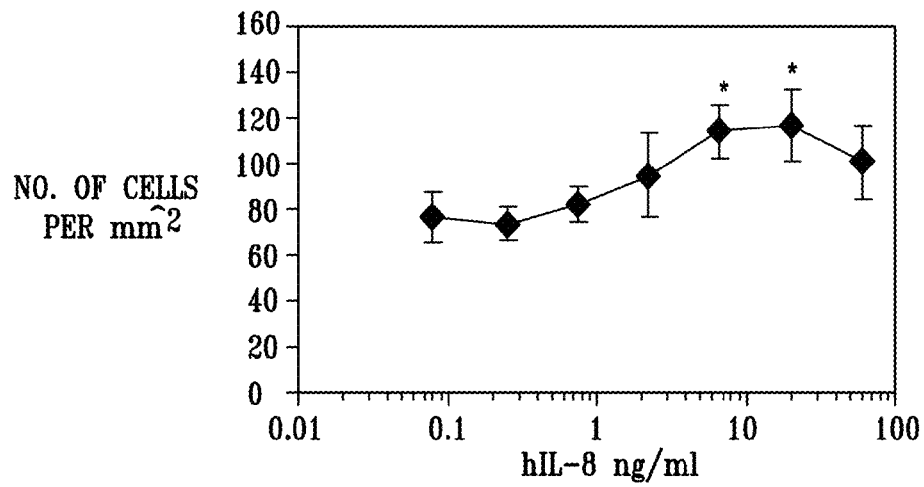

FIGS. 6A and 6B are graphs showing results obtained in five experiments of Example 10, in accordance with an embodiment of the present invention. FIG. 6A shows migration toward negative and positive control media of Ac-LDL-DiO pre-labeled ACPs. FIG. 6B shows a dosage-dependence curve reflecting migration of Ac-LDL-DiO pre-labeled ACPs in response to increasing concentrations of hIL-8. ACPs derived from the human-PBMC-derived CCP show statistically significant migration toward the positive control samples. Moreover, ACP migration corresponding to increasing hIL-8 doses was observed. Dose-dependent ACP migration peaked at 6.7-20 ng/ml of hIL-8.

Example 11

In a separate set of experiments, the human-PBMC-derived CCP was cultured in order to generate an ACP-rich PCP, as described hereinabove with reference to Examples 4 or 10. In some embodiments, generation of the ACP-rich PCP is attributed to migration of ACP cells to a specific chemokine, in combination with the differentiation of CCP cells. Migratory potential of ACP-rich PCP was measured as described hereinabove with respect to Example 10. In this example, a conditioned medium (CM) was generated using the patients' cells which secrete chemokines into the medium. The patients' cells were then extracted from the medium, leaving a chemokine-rich medium for subsequent plating of ACP therein. The potential for ACP migration in response to chemokines was then assessed when the ACPs were incubated for 1 hour with conditioned medium.

Following 1 hour incubation in the presence of negative control (M199); 20 ng/ml hIL-8; or CM (at concentrations of 2-20 ng/ml), migration of labeled cells from 10-15 random microscopic fields was evaluated using a fluorescent microscope and automated counting software (NIH ImageJ). Calculation of cell number per 1 mm^2 is based on area of counting field (×20)=0.148 mm^2 and thus each square millimeter contains 6.7 fields. It was determined that ACPs migrate toward chemokines secreted during the production of the ACP-rich PCP.

For some applications, the generated ACP-rich PCP batches were used to treat cardiovascular patients. All patients treated with these batches showed more than 10% improvement in left-ventricular-ejection fraction both 3 and 6 months following treatment. It is hypothesized that this improvement was enabled at least in part by the migration of ACPs to the vicinity.

Figure 7:
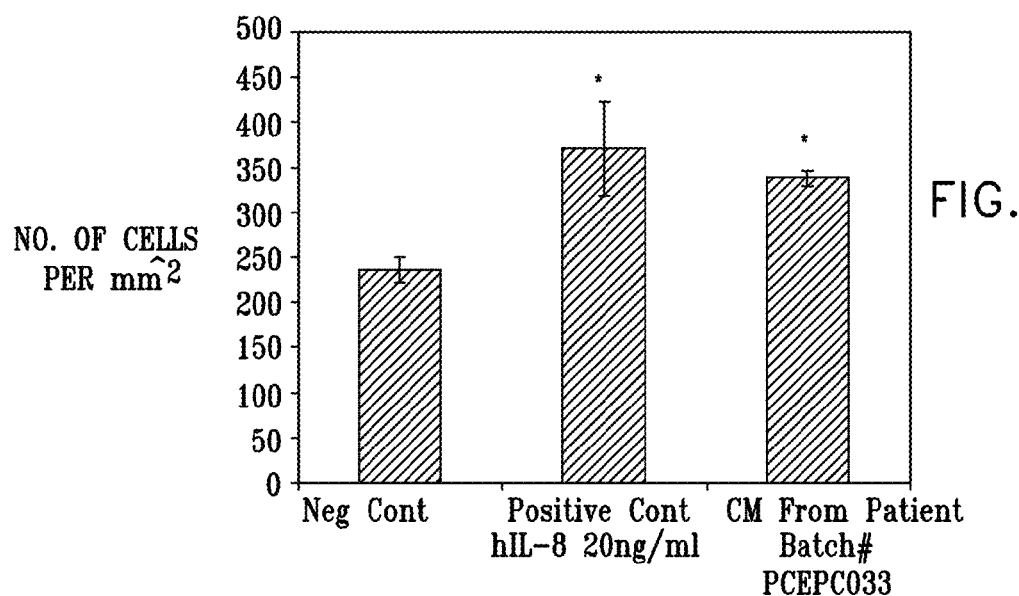
FIG. 7 is a graph showing migration of Ac-LDL-DiO pre-labeled ACPs in response to a cultured medium, in accordance with an embodiment of the present invention.

FIG. 7 is a graph showing results obtained in four experiments of Example 11, in accordance with an embodiment of the present invention. The ACPs derived from the human-PBMC-derived CCP show statistically significant migration toward the conditioned medium containing secreted chemokines; this medium was generated in the process of the production of ACP-rich PCP.

Example 12

In a separate set of experiments, migratory potential of human-PBMC toward hIL-8 was measured. In vitro assessment of PBMC migratory capability in response to hIL-8 was used to determine the potential of IL-8 to mobilize blood derived stem/progenitor cells from peripheral blood to locations in which high concentrations of IL-8 are expressed in vivo. Peripheral blood was extracted from six human volunteers for use in six respective experiments. In each experiment, a Ficoll™ gradient was used to generate a population of PBMCs. One million PBMCs were placed on 3 um pore size microporous membrane inserts which were placed in wells. 200 ul medium was placed at the bottom of each of the wells. Negative control (M199) and positive control (20 ng/ml hIL-8) diluted in M199 medium were plated in respective wells and the PBMCs cells were allowed to migrate toward each respective medium. Following 1 hour incubation in the presence of the negative control medium and the positive control medium, migration of cells from 10-15 random microscopic fields was evaluated using a fluorescent microscope and automated counting software (NIH ImageJ). Calculation of cell number per 1 mm$^2$ is based on area of counting field ($\times$20) which equals 0.148 mm$^2$, and each square millimeter contains 6.7 fields. It was determined that hIL-8 induced mobilization of only a small fraction of the PBMCs, probably the stem/progenitor cells.

FIG. 8 is a graph of migration of PBMCs in response to hIL-8, in accordance with an embodiment of the present invention. The results were obtained from six experiments (Example 12), and show that stem/progenitor cells derived from human-PBMCs migrate toward hIL-8.

Example 13

Reference is now made to FIGS. 9A and 9B which are graphs showing results obtained in the experiments following injection into rats of ACP-rich PCPs derived from a human-PBMC-derived CCP (as described hereinabove with respect to Example 4) following acute myocardial infarction, in accordance with an embodiment of the present invention.

The human-PBMC-derived CCP was cultured in order to generate an ACP-rich PCP as described in Example 4. ACP-rich PCP therapeutic potential was then assessed in a rat model of acute myocardial infarction which was induced in 15 male nude rats (200-225 g) by ligation of the left anterior descending (LAD) artery. Six days after myocardial infarction, 10 rats were injected with 1.5$\times$10$^6$ ACP-enriched cells (ACP, n=10), while 5 rats were injected with the culture medium (Control, n=5), via the aortic arch. Cardiac function (ejection fraction) and the ratio of necrotic scar area to left ventricular free wall area were measured 28 days following the ACP-rich PCP and the culture medium administrations. It is to be noted that the percentage of ejection fraction of the ACP-administered rats, as represented by FIG. 9A, increased substantially in comparison to the decreased percentage ejection fraction of the control rats. Additionally, a percentage reduction of necrotic tissue was observed in the ACP-administered rats in comparison to the percentage of necrotic tissue observed in the control rats. Paraffin fixed tissue sections obtained from the 10 ACP-administered rats were stained in order to trace engrafted human cells and cardiomyocyte (CMC) markers in the border area of the scar tissue.

Figure 9C:
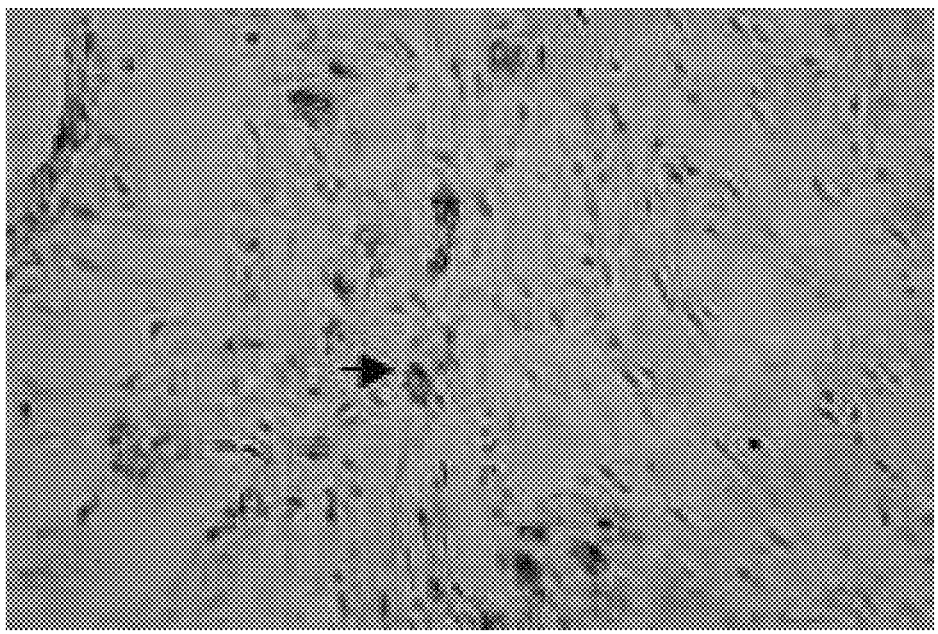
FIGS. 9C, 9D, and 9E are photographs showing sections taken from a rat's heart after injection of ACPs derived from a human-PBMC-derived CCP, produced in accordance with an embodiment of the present invention.
Figure 9D:
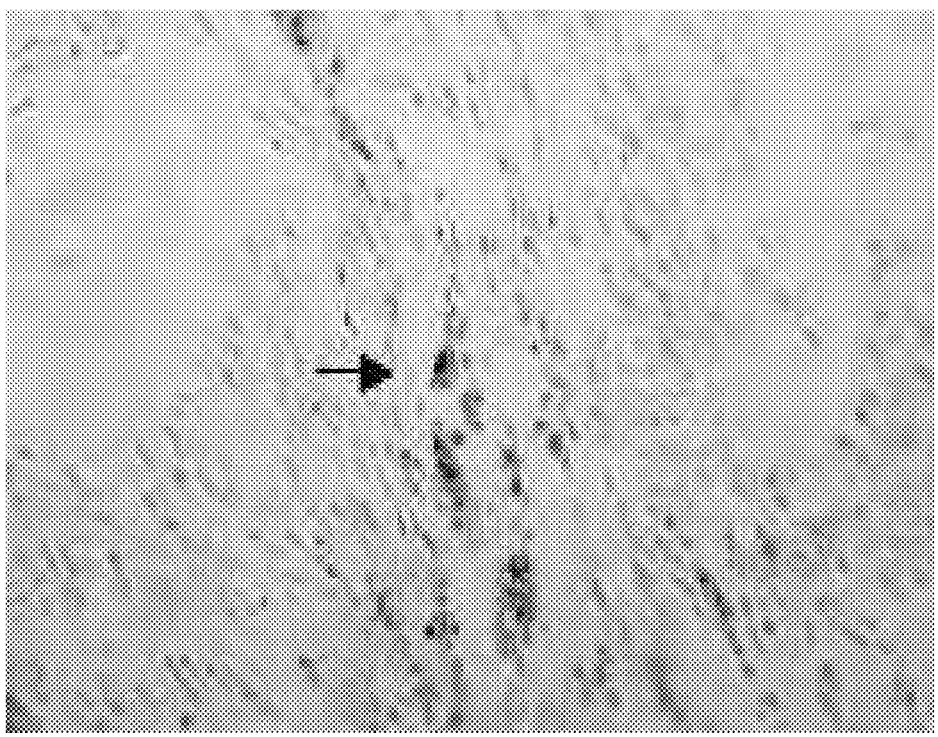
Figure 9E:
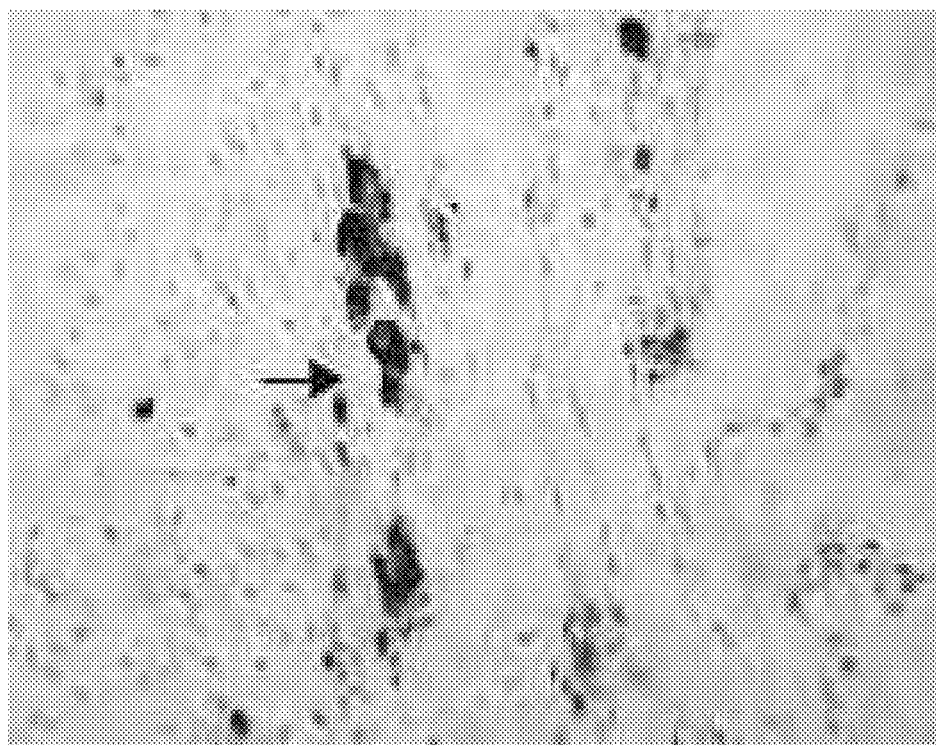

FIGS. 9C, 9D and 9E are photographs showing typical sections taken from a heart of one of the 10 rats 28 days after the injection of the ACPs derived from a human-PBMC-derived CCP in the experiments of the present example (Example 13) in accordance with an embodiment of the present invention. FIG. 9C shows staining of the rat's heart cells with anti-human mitochondria. FIG. 9D shows the cells stained for CMC markers (myosin heavy chain (MHC)), FIG. 9E shows the rat heart cells stained for cardiac Troponin I. (Reference is again made to FIG. 9C-E. The stained cells are marked by arrows). These results depicted in FIGS. 9C-D demonstrate that the human ACPs, derived in accordance with an embodiment of the present invention from the hPBMC-derived CCP, homed to damaged cardiac tissues, engrafted, and is hypothesized to have transdifferentiated into cells expressing cardiomyocyte markers.

It is to be noted that ACPs typically improve systemic endothelial functioning, as expressed by improved ejection fraction and reduced necrosis. Particular examples of improvement due to administration of ACPs, derived in accordance with an embodiment of the present invention, include improved cardiovascular functioning and improved sexual functioning. The scope of the present invention includes identifying a patient having cardiovascular dysfunction or sexual dysfunction, and administering ACPs to the patient in order to treat the dysfunction.

Example 14

In a production procedure, individual autologous human-PBMC-derived CCPs were cultured in order to generate an ACP-rich PCP, as described hereinabove. The CCPs were grown on autologous plasma-coated T75 flasks in the presence of medium containing autologous serum (>=10%), 2-10 ng/ml VEGF, and 5 IU/ml Heparin. Harvested cells, approved by Quality Control for clinical use, were administrated to patients. The therapeutic potential of ACP-rich PCP is summarized in results of administration thereof to 14 patients suffering from end-stage heart failure. Left ventricular ejection fraction (EF) and disease severity score (Score) were assessed prior to and 1-8 months after the ACP cell administration. Improvement of these parameters was calculated relative to each patient's baseline evaluation according to the following equation:

% Improvement=(Test result after treatment−Baseline test result)/Baseline test result.

Results show statistically significant improvement (p<0.0001; tested using two-tailed, paired t test analysis) in both parameters following treatment by administering ACP-rich PCP.

Table 6 shows the number of treated patients, averages and individual results relating to EF and disease severity score, as well as the calculated percent improvement thereof.

TABLE 6

| Batch No. | % EF Baseline | % EF* At 1-8 Months | EF % Improvement | SCORE Baseline | SCORE* At 1-8 Months | SCORE % Improvement |
|---|---|---|---|---|---|---|
| N | 14 | 14 | 14 | 14.0 | 14.0 | 14.0 |
| Average | 24.1 | 34.8 | 49.8 | 2.9 | 1.6 | 45.6 |
| Range | 14.9-36.0 | 20.0-50.0 | 11.1-133 | 2.0-4.0 | 1.0-3.0 | 29.0-67.0 |
| SE | 2.1 | 2.8 | 10.9 | 0.1 | 0.1 | 4.1 |
| PCEPC066 | 30.0 | 40.0 | 33.3 | 2.00 | 1.00 | 50.00 |
| PCEPC081 | 23.0 | 50.0 | 117.4 | 3.00 | 1.00 | 66.67 |
| PCEPC083 | 27.5 | 32.5 | 18.2 | 3.00 | 2.00 | 33.33 |
| PCEPC091 | 14.9 | 20.0 | 34.2 | 3.00 | 2.00 | 33.33 |
| PCEPC092 | 35.0 | 41.0 | 17.1 | 3.00 | 2.00 | 33.33 |
| PCEPC094 | 36.0 | 40.0 | 11.1 | 3.00 | 2.00 | 33.33 |
| PCEPC097 | 15.0 | 27.5 | 83.3 | 3.00 | 1.00 | 66.67 |
| PCEPC099 | 15.0 | 35.0 | 133.3 | 3.50 | 2.00 | 42.86 |
| PCEPC103 | 18.3 | 20.9 | 14.2 | 3.00 | 2.00 | 33.33 |
| PCEPC106 | 15.0 | 20.0 | 33.3 | 3.00 | 1.00 | 66.67 |
| PCEPC110 | 25.0 | 50.0 | 100.0 | 3.00 | 2.00 | 33.33 |
| PCEPC114 | 22.0 | 30.0 | 36.4 | 2.00 | 1.00 | 50.00 |
| PCEPC121 | 25.0 | 32.0 | 28.0 | 3.50 | 2.50 | 28.57 |
| PCEPC137 | 35.0 | 48.0 | 37.1 | 3.00 | 1.00 | 66.67 |

*Significant improvement $p < 0.0001$

Example 15

In a separate set of experiments, a human-PBMC-derived CCP was cultured in order to generate a cardiomyocyte (CMC)-rich PCP; the CCP was grown on fibronectin or plasma-coated T75 flasks in accordance with protocols described herein (see medium preparation).

Figure 10:
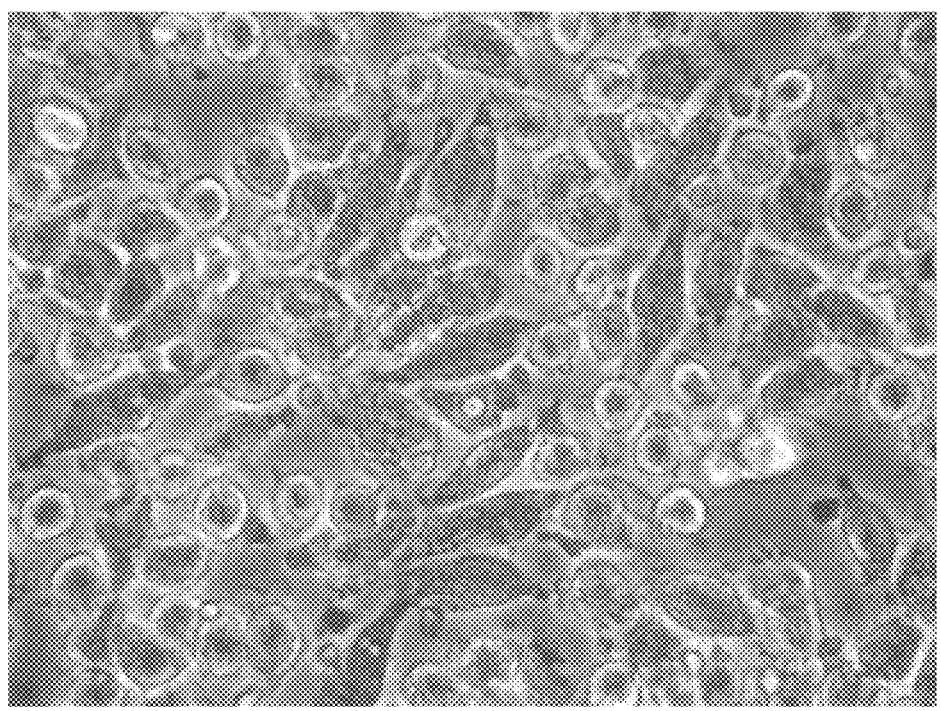
FIG. 10 is a photograph showing the morphology of cardiomyocytes derived from the CCP and produced in accordance with an embodiment of the present invention.

FIG. 10 is a photograph of a typical CMC-rich PCP from the experiments of the current example (Example 15), derived in accordance with an embodiment of the present invention. Typically, these cells appear elongated with dark cytoplasm, which may indicate high protein content. This image was obtained from ×200 magnification of cultured CMC-rich PCP cells.

Figure 11A:
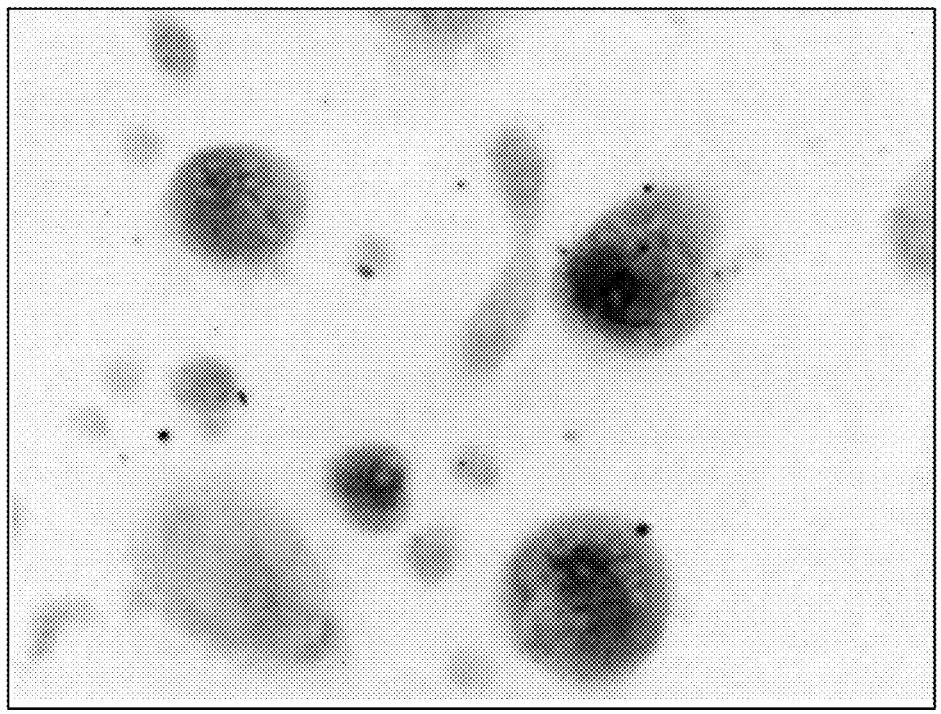
FIGS. 11A, 11B, and 11C are photographs showing immunostaining of CCP-derived cardiomyocytes, in accordance with an embodiment of the present invention.
Figure 11B:
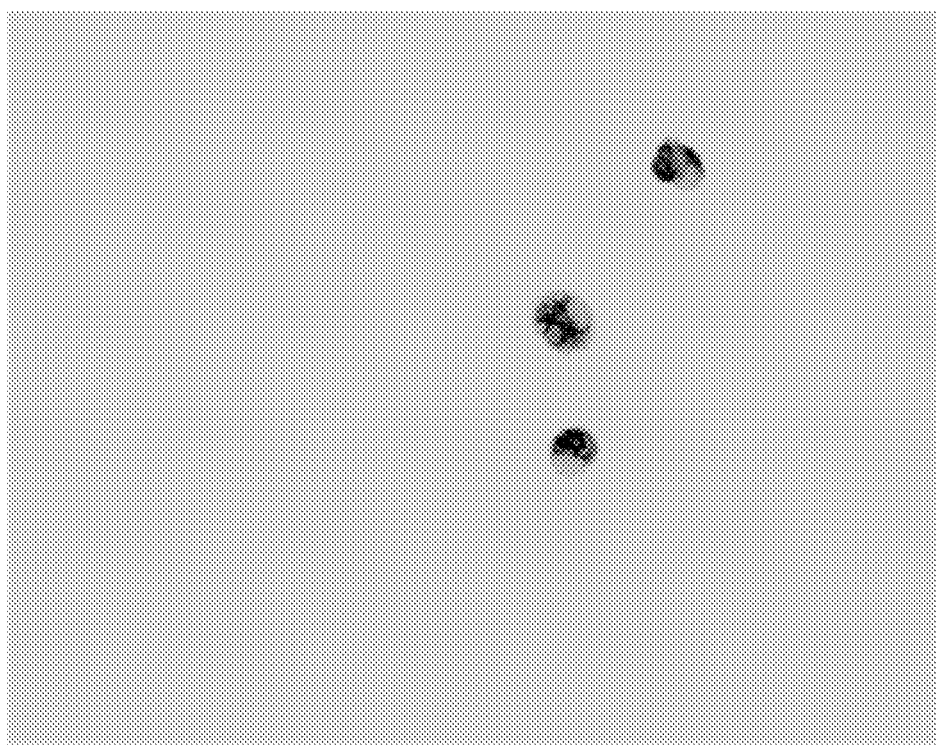
Figure 11C:
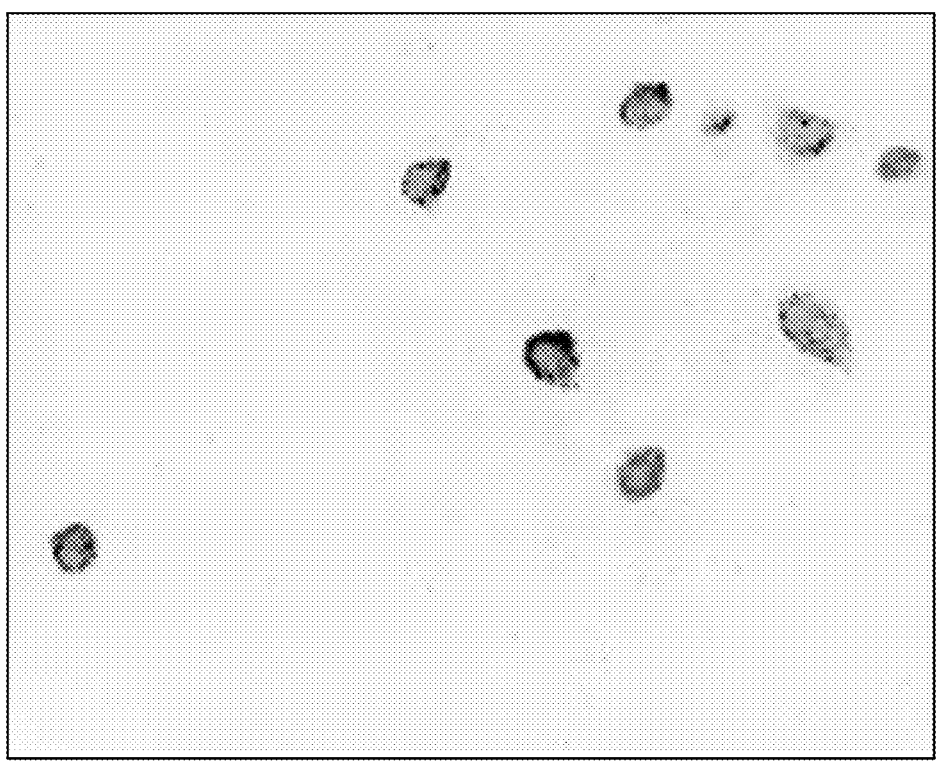

FIGS. 11A, 11B, and 11C are photographs showing immunostaining of CCP-derived cardiomyocytes in the experiments of the current example (Example 15), in accordance with an embodiment of the present invention. Slide-fixed CMC PCP cells were stained with:

FIG. 11A—anti-cardiac Troponin detected by anti-mouse Cy-3;

FIG. 11B—anti-alpha-actin detected by anti-mouse IgG-FITC; and

FIG. 11C—anti-connexin 43 detected by anti-mouse IgG-FITC.

Cells stained with non-specific mouse IgG were detected by anti-mouse IgG-FITC or by anti-mouse IgG-Cy3 and were used as negative controls.

FIGS. 11A-C show that CMC-rich PCP cells expressed the typical cardiomyocyte cellular markers: cardiac Troponin T (FIG. 11A), alpha-actin (FIG. 11B), as well as the functionally important GAP junction marker connexin-43 (FIG. 11C). The images were obtained from ×100 magnification of slide-fixed cells.

Example 16

In the same set of experiments that produced the results shown in FIGS. 10-11C, a human-PBMC-derived CCP was cultured in order to generate a CMC-rich PCP; the CCP was grown on fibronectin or plasma-coated T75 flasks in accordance with protocols described herein (see medium preparation).

Figure 12A:
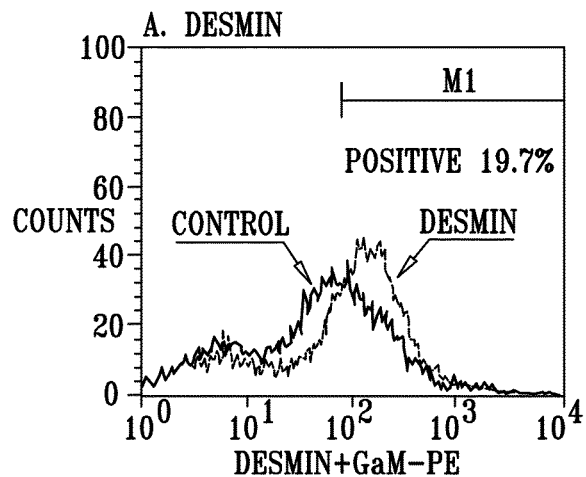
FIGS. 12A and 12B are graphs showing flow cytometry analysis results, obtained from immunostaining of a cardiomyocyte-rich PCP, in accordance with an embodiment of the present invention.
Figure 12B:
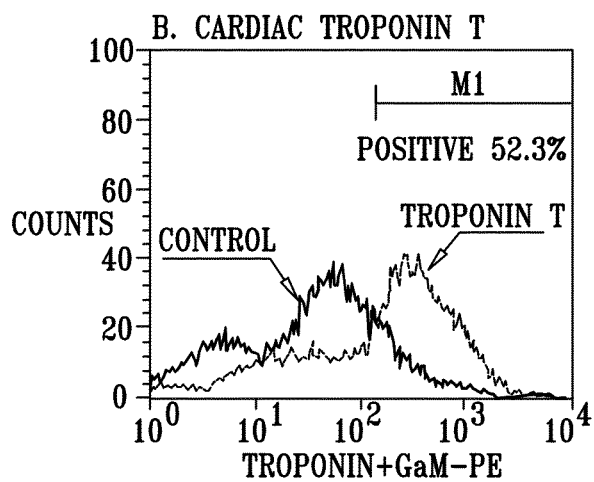

FIGS. 12A and 12B are graphs showing flow cytometry analysis results obtained from immunostaining of a CMC-rich PCP in the experiments of the current example (Example 16), in accordance with respective embodiments of the present invention. In FIGS. 12A-B, lines describing control, e.g., non-specific staining, are marked as "Control"; specific immunostaining with the cardiac cellular markers desmin and troponin T are marked as Desmin (FIG. 12A) and Troponin T (FIG. 12B), respectively. The M1 line represents the statistical marker area in which the cells are positively stained for the respective marker.

Example 17

In a separate set of experiments, a human-PBMC-derived CCP was cultured in order to generate a CMC-rich PCP, as described hereinabove. The CMC-rich PCP cells' therapeutic potential was assessed in a rat model of acute myocardial infarction. CMC-rich PCP cells were used for implantation into a rat model of induced acute myocardial infarction as described hereinabove with respect to Example 13 (with the exception that CMC-rich PCP cells were used for implantation into the rat model in the current example, whereas in Example 13, ACP-rich PCP cells were used for implantation). Six days after myocardial infarction, heart muscle of 9 rats were injected with $1.5 \times 10^6$ CMC PCP cells (CMC, n=9), while heart muscle of 5 rats were injected with culture medium (Control, n=5). Cardiac function (ejection fraction) was evaluated 14 days following the administration of the CMC-rich PCP cells or culture medium.

Figure 13:
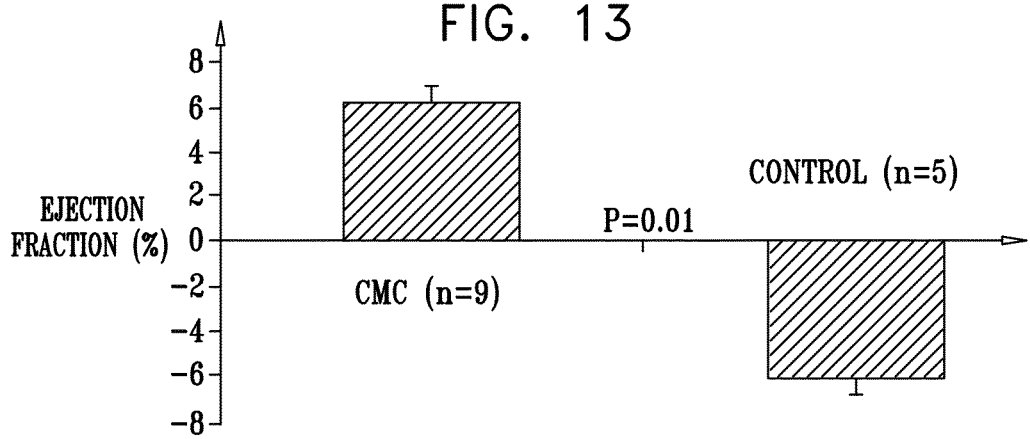
FIG. 13 is a graph showing experimental results of improved ejection fraction in a rat model of acute myocardial infarction following injection of the CCP-derived cardiomyocytes, in accordance with an embodiment of the present invention.

FIG. 13 is a graph showing experimental results obtained in the experiments of Example 13, in accordance with another embodiment of the present invention. It is to be noted that the percentage of ejection fraction of the CMC-administered rats increased substantially in comparison to the decreased percentage ejection fraction of the control rats.

A series of protocols are described hereinbelow which may be used, as appropriate, separately or in combination with Examples 1-17, in accordance with embodiments of the present invention. It is to be appreciated that numerical values are provided by way of illustration and not limitation. Typically, but not necessarily, protocols may be derived using values selected from a range of values that is within 20% of the value shown. Similarly, although certain steps are described herein with a high level of specificity, a person of ordinary skill in the art will appreciate that additional or other steps may be performed, mutatis mutandis.

In accordance with an embodiment of the present invention, generation of a single-cell suspension is carried out using the following protocols:

Protocol 1: Extraction of Peripheral Blood Mononuclear Cells (PBMC)

Receive blood bag and sterilize it with 70% alcohol.
Load blood cells onto a Ficoll™ gradient.
Spin the tubes for 20 minutes at 1050 g at room temperature (RT), with no brake.
Collect most of the plasma from the supernatant.
Collect the white blood cell fraction from every tube.
Transfer the collected cells to a new 50 ml tube, adjust volume to 30 ml per tube using PBS.
Spin tubes for 15 minutes at 580 g, RT, and discard supernatant.
Count cells in Trypan Blue.
Re-suspend in culture medium comprising, for example, X-vivo 15™.

Protocol 2: Extraction of Cells from Umbilical Cord

Isolate 10 cm umbilical cord.
Wash thoroughly with sterile PBS.
Identify the major vein of the cord, and clamp one end of the vein.
Wash twice with 30 ml sterile PBS.
Fill vein with 0.15% collagenase (about 5 ml of 0.15% collagenase solution).
Clamp the second end of the vein.
Incubate at 37 C. for 15 min.
Wash outer side of the cord with 70% ethanol.
Release the clamp from one end of the vein and collect the cell suspension.
Centrifuge for 10 min at 580 g, 21 C.
Re-suspend the cells in culture medium comprising, for example, X-vivo 15™, 10% autologous serum, 5 IU/ml heparin, and one or more growth factors.

Protocol 3: Extraction of Cells from Bone Marrow

Get bone marrow aspiration from surgical room.
Re-suspend in culture medium comprising, for example, X-vivo 15™, 10% autologous serum, 5 IU/ml heparin, and one or more growth factors.
Pass suspension through a 200 um mesh.

In accordance with an embodiment of the present invention, generation of a CCP is carried out using the following protocols:

Protocol 1: Generation of a Human CCP from PBMCs Using a Percoll™ Gradient

Prepare gradient by mixing a ratio of 5.55 Percoll™ (1.13 g/ml): 3.6 ddH2O:1 PBS×10.
For every 50 ml tube of Percoll: mix 20 ml of Percoll™ stock, 13 ml of ddH2O and 3.6 ml of PBS×10.
Mix vigorously, by vortexing, for at least 1 min.
Load 34 ml mix into each 50 ml tube.
Centrifuge tubes, in a fixed angle rotor, for 30 min at 17,000 g, 21 C., with no brake.
Gently layer 3.0 ml of cell suspension of 150 million-400 million PBMCs on top of the gradient.
Prepare a second tube with density marker beads: gently layer 3.0 ml of medium on top of the gradient.
Gently load density marker beads—10 ul from each bead type.
Centrifuge tubes, in a swinging bucket rotor, for 30 min at 1260 g at 13 C., with no brake.
Gently collect all bands located above the red beads, and transfer to tube with 10 ml medium.
Centrifuge cells for 15 min at 580 g at 21 C.
Discard supernatant and re-suspend pellet in medium.
Count cells in Trypan blue.
Centrifuge cells for 10 min at 390 g, 21 C.
Discard supernatant and re-suspend pellet in medium.
Take CCP cells for FACS staining.

Protocol 2: Generation of Human CCP from PBMCs Using an OptiPrep™ Gradient

Take up to 130 million cells for each enrichment tube.
Spin cells for 10 min at 394 g, 21 C.
Suspend cell pellet in 10 ml of donor serum.
Prepare a 1.068 g/ml OptiPrep™ gradient by mixing a ratio of 1 OptiPrep™: 4.1 PBS.
For every 50 ml enrichment tube:
Mix 10 ml of cell suspension with 4 ml OptiPrep™.
For preparation of a 1.068 g/ml OptiPrep™ gradient, mix 5 ml of OptiPrep™ and 20.5 ml of PBS.
Gently layer 20 ml of the 1.068 g/ml gradient on top of the cell suspension.
Gently layer 1.5 ml Hank's buffered saline (HBS) on top of the gradient layer.
Centrifuge for 30 min at 700 g at 4 C., with no brake.
Gently collect the layer of cells that floats to the top of the 1.068 g/ml OptiPrep™ gradient into a 50 ml tube pre-filled with PBS.
Centrifuge for 10 min at 394 g, 21 C.
Discard supernatant and re-suspend pellet in medium.
Count cells in Trypan Blue.

It is to be noted that culture containers are typically either un-coated or coated with one or a combination of ACP-enhancing materials such as collagen, fibronectin, CD34, CD133, Tie-2, or anti-CD117.

In accordance with an embodiment of the present invention, the coating of a tissue culture container is carried out using the following protocols:

Protocol 1: Coating T75 Flasks with 25 ug/ml Fibronectin

For 20 T75 flasks—Prepare up to seven days before, or on day of PBMC preparation.
Prepare 50 ml of 25 ug/ml fibronectin solution in PBS.
Fill every flask with 2-5 ml fibronectin 25 ug/ml.
Incubate at 37 C. for at least 30 min.
Collect fibronectin solution.
Wash flask twice in PBS.
Dry flasks
Keep dry flasks at room temperature.
Dried flasks can be saved for one week at room temperature (RT).

Protocol 2: Coating T75 Flasks with 25 ug/ml Fibronectin and 5 ng/ml BDNF

Coat flasks with Fibronectin 25 μg/ml, as described in Protocol 1.
Prepare 50 ml of 5 ng/ml BDNF solution in PBS.

After washing off Fibronectin, fill every flask with 2-5 ml BDNF 10 ng/ml.
Incubate at 37 C. for 1 hour.
Collect the solution.
Wash flask twice in 10 ml PBS.
Keep dry flasks at room temperature until use.

In accordance with an embodiment of the present invention, serum preparation is carried out using the following protocol: (Serum can be obtained directly or prepared from plasma).

Protocol: Preparation of Serum from Human Plasma

Take 100 ml of undiluted blood.
Spin at 1100 g (2500 rpm) for 10 min.
Transfer the upper layer (plasma) to a new 50 ml tube.
Add 1.0 ml 0.8M $CaCl_2$-$2H_2O$ for every 40 ml plasma.
Incubate for 0.5-3 hours at 37 C.
Spin coagulated plasma 5 min at 2500 g.
Collect the serum in a new tube, avoiding clotting.
Aliquot collected serum and save at −20 C. until use.

In accordance with an embodiment of the present invention, medium preparation is carried out using the following protocols:

Medium should contain 1-20% autologous serum and/or 1-20% conditioned medium.

Medium can contain one or more additives, such as LIF, EPO, IGF, b-FGF, M-CSF, GM-CSF, TGF alpha, TGF beta, VEGF, BHA, BDNF, NGF, EGF, NT3, NT4/5, GDNF, S-100, CNTF, NGF3, CFN, ADMIF, estrogen, progesterone, cortisone, cortisol, dexamethasone, or any other molecule from the steroid family, prolactin, an adrenocorticoid hormone, ACTH, glutamate, serotonin, acetylcholine, NO, retinoic acid (RA) or any other vitamin D derivative, Heparin, insulin, forskolin, Simvastatin, MCDB-201, MCT-165, glatiramer acetate, a glatiramer acetate-like molecule, IFN alpha, IFN beta or any other immunoregulatory agent sodium selenite, linoleic acid, ascorbic acid, transferrin, 5-azacytidine, PDGF, VEGF, cardiotrophin, and thrombin or Rosiglitazone in various concentrations, typically ranging from about 100 pg/ml to about 100 μg/ml (or molar equivalents).

Typically, medium should not be used more than 10 days from its preparation date.

Protocol 1: Medium for Enhancement of
CCP-Derived Angiogenic Cell Precursors (ACPs)

Serum-free medium (e.g., X-vivo 15™)
10% autologous serum
5 IU/ml Heparin
5 ng/ml VEGF
1 ng/ml EPO Protocol 2: Medium for Enhancement of
CCP-Derived Neuronal Progenitor Cells Serum-free medium (e.g., X-vivo 15™)
20 ng/ml bFGF
50 ng/ml NGF
200 uM BHA (this is added during the last 24 hours of culturing)
10 ng/ml IFN beta
10 ug/ml glatiramer acetate
10 uM forskolin
1 uM cortisone
1 ug/ml insulin Protocol 2.1: Medium for Enhancement of
CCP-Derived Neuronal Progenitor Cells Serum-free medium (e.g., X-vivo 15™)
20 ng/ml bFGF
50 ng/ml NGF
25 ng/ml BDNF
200 uM BHA (this is added during the last 24 hours of culturing)

Protocol 3: Medium for Enhancement of
CCP-Derived Retinal Cells

Serum-free medium (e.g., X-vivo 15™)
10% autologous serum
5 IU/ml Heparin
10 ng/ml EGF
20 ng/ml bFGF
10 ug/ml glatiramer acetate
50 ng/ml NGF3

Protocol 4a. Medium for Enhancement of
CCP-Derived Cardiomyocyte (CMC) Progenitor Cells Step I
Serum-free medium (e.g., X-vivo 15™)
10% autologous serum
20 ng/ml bFGF
20 ug/ml IFN beta
5 IU heparin.
Step II
Five to ten days after culture onset, add 3 uM 5-azacytidine for 24 hours.

Protocol 4b: Medium for Enhancement of
CCP-Derived CMC Progenitor Cells

Serum free medium DMEM-Low glucose
20% autologous serum
10% MCDB-201
2 ug/ml Insulin
2 ug/ml Transferin
10 ng/ml Sodium Selenite
50 mg/ml BSA
1 nM Dexamethasone
20 ug/ml Glatiramer acetate
0.47 ug/ml Linoleic acid
0.1 mM Ascorbic Acid
100 U/ml penicillin In accordance with an embodiment of the present invention, conditioned medium preparation is carried out using the following protocol:

Protocol 1: Preparation of 100 ml Enriched Medium
Containing 10% Autologous Conditioned Medium Thaw 10 ml conditioned medium in an incubator.
When thawed, add it to culture medium using pipette.
Extraction of Tissue Pieces for Co-Culture:
Dissection of Rat Blood Vessels (Other Non-Human or Human Tissues May Also be Used):
Anesthetize animal using anesthetic reagents (e.g., 60-70% CO2, isoflurane, benzocaine, etc.).
Lay animal on its back and fix it to an operating table.
Using sterile scissors, cut animal's skin and expose the inner dermis.

Using a second set of sterile scissors, cut the dermis, cut chest bones, and expose the heart and aorta.

Cut small pieces, 0.2-1 cm long, from the aorta and other blood vessels, and place them in a container pre-filled with 50 ml cold culture medium (e.g. RPMI, X-vivo 15™, or any other growth medium).

Using forceps and scissors, clean tissue sections, to remove outer layers such as muscle, fat, and connective tissue.

Using forceps and scalpel, cut each blood vessel along its length, and expose the inner layer of endothelial cells.

Using forceps and scalpel, cut small pieces of up to 0.1 cm2 from the tissue.

It is to be understood that whereas this technique is in accordance with one embodiment of the present invention, the scope of the present invention includes extracting a blood vessel from a human, as well. For example, an incision may be made over the saphenous vein, in order to facilitate dissection of a distal 1 cm portion of the vein. Tributary veins thereto are tied and transected. Distal and proximal ends of the 1 cm portion of the saphenous vein are tied, and the vein is harvested.

Use the dissected tissue for direct and/or indirect co-culturing with the CCP and/or to generate conditioned medium.

Generation of Conditioned Medium:

Lay dissected pieces in culture containers, for example in T75 flasks, or 50 ml tubes.

Optionally, fill with cell culture medium containing 0.1-3 ug/ml or 3-100 ug/ml apoptotic reagent (such as valinomycin, etoposide or Staurosporine), until all pieces are covered.

Refresh culture medium every 2 days.

Collect this medium (now conditioned medium) into 50 ml tubes.

Spin collected conditioned medium at 450 g for 10 min, at room temperature.

Collect supernatant in a new sterile container.

Details regarding preservation of the conditioned medium, in accordance with an embodiment of the present invention, are described hereinbelow.

In accordance with an embodiment of the present invention, culturing of a CCP to produce a PCP is carried out using the following protocols:

Protocol 1: Culturing of CCP Cell Suspension in T75 Flasks

Spin suspension for 15 minutes at 450 g, 21 C.
Discard the supernatant.
Gently, mix cell pellet and re-suspend the CCP cells.
Re-suspend pellet to 10 million CCP cells/ml.
Fill T75 flask with 15 ml enriched medium, and add 5 ml of 10 million CCP cells/ml to attain a final concentration of 50 million CCP cells/flask.
Incubate T75 flasks, plates and slides at 37 C., 5% CO2.

Protocol 2: Applied Hypoxia

For some applications, increased expansion and/or differentiation of the CCP may be obtained by exposure of the cell culture to oxygen starvation, e.g., 0.1-5% or 5-15% oxygen (hypoxia), for 2-12 or 12-48 hours. This is typically done one or more times, at different points during cell culturing.

Incubate T75 flasks in an oxygen-controlled incubator.
Set the oxygen pressure at 0.1%, and maintain it at this level for 24 hours.
Remove the flasks from the incubator and examine the culture.
Take a sample of CCP cells and test viability by Trypan blue exclusion method.
Set the oxygen pressure of the incubator at 20%.
Re-insert the flasks into the incubator and continue incubation for the rest of the period. This procedure can be repeated, for example, once a week during the culture period and/or within 24, 48, or 72 hours before termination of the culture.

Protocol 3: Reseeding of Adherent and/or Detached and/or Floating Cells

For some applications, increased expansion and differentiation of the CCP may be achieved by re-seeding collected cells on new pre-coated dishes in culture medium.

Collect all cultured CCP in tubes.
Spin tubes for 10 minutes at 450 g, 21 C.
Discard the supernatant.
Gently mix pellet and re-suspend cells in 10 ml fresh medium per T75 flask.
Seed suspended cells in new pre-coated T75 flasks.
Continue culturing the cells, and perform all other activities (e.g., medium refreshment, visual inspection, and/or flow cytometry), as appropriate, as described herein.
This procedure can be performed weekly during the culture period and/or within 24, 48, or 72 hours before termination of the culture.

In accordance with an embodiment of the present invention, co-culturing of CCP with tissue-derived conditioned medium is carried out using the following protocol:

Protocol 1: Culturing of CCP in the Presence of Conditioned Medium Derived from a Blood Vessel Culture Spin CCP cells for 15 minutes at 500 g, 21 C.
Discard the supernatant.
Gently mix cell pellet and re-suspend cells to 5-50 million/ml in autologous medium containing 1-20% autologous serum and/or 1-20% conditioned medium.
Seed flasks with 2-5 million CCP cells/ml.
Incubate flasks at 37 C., 5% CO2.
After first three days of culture, non-adherent cells can be removed from the culture.

In accordance with an embodiment of the present invention, refreshing of the media in ongoing growing CCP cultures is carried out using the following protocol:

Refreshing of the media in ongoing growing flasks should occur every 3-4 days.

Protocol 1: Refreshing of Medium in T-75 Flasks

Collect non-adherent cells in 50 ml tubes.
Fill every flask with 10 ml fresh culture medium enriched with conditioned medium.
Spin tubes for 10 minutes at 450 g, RT; discard the supernatant.
Gently mix cell pellet and re-suspend cells in 10 ml/flask fresh culture medium enriched with condition medium.
Return 5 ml of cell suspension to every flask.

In accordance with an embodiment of the present invention, indirect co-culture of CCP cells with tissue dissection is carried out using the following protocol:

Protocol 1: Indirect Co-Culture of Dissected Blood Vessel and CCP Cells in a Semi-Permeable Membrane Apparatus Lay dissected tissue pieces in the upper chamber of the apparatus on top of the semi-permeable membrane.

Implant CCP cells in lower chamber.
Lower chamber can be pre-coated with growth-enhancing molecules such as collagen, plasma, fibronectin, a growth factor, tissue-derived extra cellular matrix and an antibody.
Refresh culture medium in the upper chamber—aspirate conditioned medium into 50 ml tubes and add autologous culture medium.
Preserve collected conditioned medium at −20 C.
Remove upper chamber after four days of co-culture.
Refresh culture medium of the CCP cells with culture medium containing 1-20% autologous serum and/or 1-20% conditioned medium.
Continue growing and harvesting as described herein.
Co-Culture in Separate Chambers within a Culture Container In accordance with an embodiment of the present invention, co-culturing within a culture container is carried out using the following protocol:

Protocol 1: Direct Co-Culturing of Autologous Dissected Blood Vessel and CCP Cells Lay dissected tissue pieces in pre-coated flasks.
Implant CCP cells in pre coated second chamber.
Using forceps, take out tissue pieces after four days of co-culture.
Refresh culture medium of the CCP cells with culture medium containing 1-20% autologous serum and/or 1-20% condition medium.
Continue growing and harvesting as described herein.

In accordance with an embodiment of the present invention, harvesting of the cellular product is carried out using the following protocol:

Protocol 1: Collection of Resulting ACP Cultures

Collect cells in 50 ml tubes.
Carefully wash flask surface by pipetting with cold PBS to detach adherent cells.
Collect washed adherent cells to 50 ml tubes.
Add 5 ml of cold PBS.
Detach remaining adherent cells using gentle movements with cell scraper.
Collect the detached cells and add them to the tubes
Optionally, add 5 ml EDTA to each flask and incubate at 37 C. for 5 min.
Collect the detached cells and add them to the tubes Spin tubes for 5 min, at 450 g, room temperature.
Re-suspend the pellets in 2-5 ml PBS.
Count the cells in Trypan blue.

In accordance with an embodiment of the present invention, cellular product preservation is carried out using the following protocols:
Cellular product can be kept in preservation media or frozen in freezing buffer until use for transplantation into a patient.

Protocol 1: Cryopreservation of Cellular Product

Prepare freezing buffer containing 90% human autologous serum and 10% DMSO.
Suspend cellular product in freezing buffer and freeze in liquid nitrogen.

Protocol 2: Short-Period Preservation of Cellular Product

Prepare preservation medium including growth medium containing 1-20% autologous serum, with few or no other additives. Maintain preservation medium with cellular product at 2-12 C.

In accordance with an embodiment of the present invention, conditioned medium collection and preservation is carried out using the following protocol:
Conditioned medium can be kept until use for growth medium preparation.
Conditioned medium should be collected under sterile conditions.
Spin collected conditioned medium for 10 min at 450 g, 21 C.
Collect supernatant in a new sterile container.
Filter supernatant through a 22 um membrane.
Aliquot conditioned medium to 10 and/or 50 ml sterile tubes, pre-marked with donor details.
Keep at −20 C. until use.

In accordance with an embodiment of the present invention, FACS staining is carried out using the following protocol:

Protocol 1: Staining of ACP Enriched Population

FACS Staining Protocol:

| Tube No. | Staining | Aim of staining |
|---|---|---|
| 1. | Cells | Un-stained control |
| 2. | CD45 (IgG1)-FITC | Single staining for PMT and compensation settings |
| 3. | CD14-PE (IgG2a) | |
| 4. | CD45 (IgG1)-APC | |
| 5. | mIgG1-FITC<br>mIgG1-PE<br>mIgG1-APC | Isotype control |
| 6. | CD45-FITC (IgG1)<br>KDR-PE (IgG2a)<br>CD34-APC (IgG1) | |
| 7. | Ac-LDL-FITC<br>CD31-PE (IgG1) | |
| 8. | Ulex-Lectin-FITC<br>CD31-PE (IgG1) | |
| 9. | mIgG1-FITC<br>mIgG2a-PE<br>mIgG1-APC | Isotype control |
| 10. | CD45-FITC (IgG1)<br>CD133-PE (IgG2a)<br>CD34-APC (IgG1) | |

Protocol 2: Staining of CMC Progenitors

FACS Staining Protocol for Fixed Permeabilized Cells:

| Tube No. | Staining 1st step | Staining 2nd step | Aim of staining |
|---|---|---|---|
| 1 | Cells | | Un-stained control |
| 2 | CD45-FITC (IgG1) | | Single staining for PMT and compensation settings |
| 3 | CD14-PE (IgG2a) | | |
| 5 | mIgG1 | Anti mouse -PE | Isotype control |
| 6 | Desmin | Anti mouse -PE | |
| 7 | Troponin T | Anti mouse -PE | Isotype control |

In accordance with an embodiment of the present invention, immunohistochemistry staining (IHC) is carried out using the following protocols:

Protocol 1: IHC Staining Protocol for ACPs

| Slide No. | Staining 1st step | Aim of staining |
|---|---|---|
| 1. | mIgG1 | Isotype control |
| 2. | mIgG1-PE | Isotype control |
| 3. | CD34-APC | Specific Staining |
| 4. | CD144-FITC | Specific Staining |
| 5. | CD133-PE | Specific Staining |
| 6. | Ac-LDL-FITC CD31-PE | Specific Staining |
| 7. | Ulex-Lectin-FITC CD31-PE | Specific Staining |

Protocol 2: IHC Staining Protocol for CMC Progenitors

| Slide No. | Staining 1st step | Staining 2nd step | Aim of staining |
|---|---|---|---|
| 1. | — | mIgG1-FITC | Isotype control |
| 2. | mIgG1 | Anti mouse-Cy-3 | Isotype control |
| 3. | Connexin 43 | Anti mouse-FITC | Specific Staining |
| 4. | Alfa actin | Anti mouse-FITC | Specific Staining |
| 5. | Troponin | Anti mouse-PE | Specific Staining |

In accordance with an embodiment of the present invention, a tube formation assay is carried out using the following protocol:

Tube formation was tested using the ECM625(Chemicon) in vitro angiogenesis assay kit.

Angiogenic pattern and vascular tube formation was numerically scored as described by Kayisli U. A. et al. 2005 (52).

In accordance with an embodiment of the present invention, secretion of cytokines from harvested cells is assessed using the following protocols:

Culture 0.5–1×10^6 cells/ml over night in 24 well plates in serum-free medium (e.g., X-vivo 15)

Collect culture supernatant and spin at 1400 rpm for 5 minutes

Transfer supernatant to an eppendorf tube and freeze at −80 C. until ready to test cytokine secretion.

Protocol 1: ELISA for IL-8

A commercial DuoSet CXCr8/IL-8 (R&D Systems) was used for the detection of IL-8 secretion.

Protocol 2: Cytometric Bead Array

A commercial cytometric bead array (CBA) kit for human angiogenesis (BD 558014) was used for the detection of IL-8, VEGF, TNF and Angiogenin secretion.

It is to be noted that the scope of the present invention includes injecting IL-8 into a human patient in order to recruit ACP cells to a given destination within a given patient, in accordance with the needs of the patient.

For some applications, techniques described herein are practiced in combination with techniques described in one or more of the references cited in the Background section and Cross-References section of the present patent application. All references cited herein, including patents, patent applications, and articles, are incorporated herein by reference.

It is to be appreciated that by way of illustration and not limitation, techniques are described herein with respect to cells derived from an animal source. The scope of the present invention includes performing the techniques described herein using a CCP derived from non-animal cells (e.g., plant cells), mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of making a composition comprising:
obtaining an initiating cell population (ICP) of at least ten thousand cells that have a density of less than 1.072 g/ml and at least 25% of which are CD31Bright; and
in vitro stimulating the ICP by culturing the ICP in the presence of one or more factors selected from the group consisting of: autologous serum, vascular endothelial growth factor (VEGF), heparin, insulin-like growth factor (IGF), basic fibroblast growth factor (b-FGF), epidermal growth factor (EGF), and ascorbic acid, to differentiate into a progenitor/precursor cell population (PCP) comprising a subpopulation of cells that stain as CD31Bright, demonstrate uptake of Ac-LDL+ and secrete interleukin-8 (IL-8) and angiogenin, wherein the sub-population of cells comprises at least 10% of cells in the PCP, to provide for said composition.

2. The method according to claim 1, wherein at least 30% of the cells of the ICP are CD31Bright, and wherein stimulating the ICP comprises stimulating the ICP of which at least 30% of the cells are CD31Bright.

3. The method according to claim 1, wherein the ICP includes at least 5 million cells that have a density of less than 1.062 g/ml, at least 1% of which are CD34+CD45−/Dim, and wherein stimulating the ICP comprises stimulating the ICP that has the at least 5 million cells that have a density of less than 1.062 g/ml.

4. The method according to claim 1, comprising applying cells extracted from a mammalian donor to one or more gradients suitable for selecting cells having a density of less than 1.072 g/ml, and deriving the ICP from the cells applied to the gradient.

5. The method according to claim 1, comprising identifying the PCP as being suitable for therapeutic implantation in response to an assessment that the PCP includes at least 1 million PCP cells.

6. The method according to claim 1, comprising identifying the PCP as being suitable for therapeutic implantation in response to an assessment that the PCP includes at least 1 million angiogenic cell precursors (ACPs).

7. The method according to claim 1, wherein stimulating the ICP comprises culturing the ICP in a culture medium comprising at least 10% serum, for a duration of between 1 and 120 days.

8. The method according to claim 1, comprising characterizing the PCP as including angiogenic cell precursors (ACPs), in response to an evaluation of at least one feature selected from the group consisting of: a phenotypical feature of cells in the PCP, a genotypical feature of cells in the PCP, and a physiological feature of cells in the PCP.

9. The method according to claim 8,
wherein the phenotypical feature includes a morphological feature selected from the group consisting of: a cell size larger than 20 um, an elongated cell, a spindle-shaped cell, an irregularly-shaped cell, a granulated cell, a cell including an enlarged dark nucleus, a multinuclear cell, a cell including flagella-like structures, a cell including pseudopodia, and a cell having a polygonal shape; and
wherein characterizing the PCP comprises characterizing the PCP in response to an evaluation of the selected morphological feature.

10. The method according to claim 8, wherein characterizing the PCP comprises characterizing the PCP in response to an identification in the PCP of a feature selected from the group consisting of: CD31, CD31Bright, CD34, CD117, CD133, Tie-2, CD34+CD133+, KDR, CD34+KDR+, CD144, von Willebrand Factor, SH2 (CD105), SH3, fibronectin, collagen type I, collagen type III, collagen type IV, ICAM type 1, ICAM type 2, VCAM1, vimentin, BMP-R IA, BMP-RII, CD44, integrin b1, aSM-actin, MUC18, and CXCR4.

11. The method according to claim 8, wherein characterizing the PCP comprises assessing secretion by the PCP of a molecule selected from the group consisting of: IL-8, angiogenin, VEGF, MMP2, and MMP9.

12. The method according to claim 8, wherein characterizing the PCP comprises culturing at least a portion of the PCP on a membrane, and identifying a tendency of the at least a portion of the PCP to migrate toward a chemoattractant selected from the group consisting of: bFGF, VEGF, SCF, G-CSF, GM-CSF, IL-8, and SDF-1.

13. The method according to claim 1, wherein stimulating the ICP comprises incubating the ICP in a container having a surface comprising a growth-enhancing factor.

14. The method according to claim 13, wherein the growth-enhancing factor comprises a factor selected from the group consisting of: collagen, plasma, fibronectin, a growth factor, tissue-derived extra cellular matrix, and an antibody to a stem cell surface receptor.

15. The method according to claim 1, comprising:
during a hypoxic time period lasting at least 2 hours, culturing the ICP under hypoxic conditions; and
during a non-hypoxic time period lasting at least 1 day, culturing the ICP under non-hypoxic conditions.

16. The method according to claim 15, wherein the hypoxic and non-hypoxic time-periods are within a culturing time period lasting less than 30 days, and wherein culturing the ICP under hypoxic conditions comprises culturing the cells under hypoxic conditions during a first two days of the culturing time period.

17. The method according to claim 1, wherein stimulating comprises co-culturing the ICP with a sample tissue.

18. The method according to claim 17, wherein co-culturing comprises:
utilizing the sample tissue to produce a conditioned medium; and
co-culturing the ICP with the sample tissue in the conditioned medium.

\* \* \* \* \*